US007335357B2

(12) United States Patent
Klagsbrun et al.

(10) Patent No.: US 7,335,357 B2
(45) Date of Patent: Feb. 26, 2008

(54) ANTAGONISTS OF NEUROPILIN RECEPTOR FUNCTION AND USE THEREOF

(75) Inventors: Michael Klagsbrun, Newton, MA (US); Shay Soker, Brookline, MA (US); Hua-Quan Miao, Brookline, MA (US); Seiji Takashima, Osaka (JP)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 11/488,364

(22) Filed: Jul. 18, 2006

(65) Prior Publication Data

US 2006/0251650 A1 Nov. 9, 2006

Related U.S. Application Data

(63) Continuation of application No. 10/104,440, filed on Mar. 22, 2002, which is a continuation of application No. 09/580,803, filed on May 30, 2000, now abandoned, which is a continuation of application No. PCT/US98/26114, filed on Dec. 9, 1998.

(60) Provisional application No. 60/078,541, filed on Mar. 19, 1998, provisional application No. 60/069,155, filed on Dec. 9, 1997, provisional application No. 60/069,687, filed on Dec. 12, 1997.

(51) Int. Cl.
*A61K 39/395* (2006.01)

(52) U.S. Cl. .................................................. 424/130.1

(58) Field of Classification Search ..................... None
See application file for complete search history.

(56) References Cited

OTHER PUBLICATIONS

Gura (1997, Science 278:1041-1042).*
(MSNBC News Services, "Mixed results on new cancer drug", Nov. 9, 2000).*
Miller (Breast Cancer Treatment and Research, 2002, 75: S45-S50).*
J. K. Kim et al., *Nature*, 362(6423) 841-844, 1993.
M. Klagsbrun et al., *Current Biology*, 3(1):699-702, 1993.
Z. Poltorak et al., *J. Biol. Chem.*, 272(11) 7151-7158, 1997.
H. Chen et al., *Neuron*, 19:547-559, 1997.
A. L. Kolodkin et al., *Cell*, 90:753-762, 1997.
Basile, et al., *Cancer Research*, 64:5212-5224, 2004.
Neufeld, *Frontiers in Bioscience*, 10:751-760, 2005.
Muller, et al., *Current Opinion in Genetics and Development*, 6(4):469-474, (abstract only), 1996.
Freshney, *Culture of Animal Cells, A Manual of Basic Technique, Alan R. Liss, Inc.*, p. 4, New York, 1983.
Dermer, *Bio/Technology*, 12:320, 1994.
MSNBC News Services, "*Mixed results on new cancer drug*", Nov. 9, 2000.
Gura, *Science*, 278:1041-1042, 1997.
FDA News. "FDA Approves First Angiogenesis Inhibitor to Treat Colorectal Cancer" http://www.fda.gov/bbs/topics/NEWS/2004/NEW01027.html, P04-23 (Feb. 26, 2004).
Ferrara, et al. "Angiogenesis as a therapeutic target" *Nature* 438: 967-974 (2005).
He, et al. "Neuropilin Is a Receptor for the Axonal Chemorepellent Semaphorin III" *Cell* 90:739-751 (1997).
Kowanetz, et al. "Vascular Endothelial Growth Factor Signaling Pathways: Therapeutic Perspective" *Clinical Cancer Res.* 12(17): 5018-5022 (2006).
Li, et al. "Pancreatic Carcinoma Cells Express Neuropilins and Vascular Endothelial Growth Factor, but Not Vascular Endothelial Growth Factor Receptors" *Wiley InterScience* (2004).
Liang, et al. "Function Blocking Antibodies to Neuropilin-1 Generated from a Designed Human Synthetic Antibody Phage Library" *J. Mol. Biol.* (2006).
Pan, et al. "Blocking Neuropilin-1 Function Has an Additive Effect with Anti-VEGF to Inhibit Tumor Growth" *Cancer Cell* 11: 53-67 and Supplemental Data (2007).
Shojaei, et al. "Antiangiogenesis to treat cancer and intraocular neovascular disorders" *Laboratory Investigation* 87: 227-230 (2007).

* cited by examiner

*Primary Examiner*—Karen A. Canella
*Assistant Examiner*—Catherine Joyce
(74) *Attorney, Agent, or Firm*—Nixon Peabody LLP

(57) ABSTRACT

The present invention relates to antagonists of neuropilin receptor function and use thereof in the treatment of cancer, particularly metastatic cancer, and angiogenic diseases.

5 Claims, 30 Drawing Sheets

```
1   MERGLPLLCAVLALVLAPAGAFRNDKCGDTIKIESPGYLTSPGYPHSYHPSEKCEWLIQAPDPYQRIMIN 70
71  FNPHFDLEDRDCKYDYVEVFDGENENGHFRGKFCGKIAPPPVVSSGPFLFIKFVSDYETHGAGFSIRYEI 140
141 FKRGPECSQNYTTPSGVIKSPGFPEKYPNSLECTYIVFAPKMSEIILEFESFDLEPDSNPPGGMFCRYDR 210
211 LEIWDGFPDVGPHIGRYCGQKTPGRIRSSSGILSMVFYTDSAIAKEGFSANYSVLQSSVSEDFKCMEALG 280
281 MESGEIHSDQITASSQYSTNWSAERSRLNYPENGWTPGEDSYREWIQVDLGLLRFVTAVGTQGAISKETK 350
351 KKYYVKTYKIDVSSNGEDWITIKEGNKPVLFQGNTNPTDVVVAVFPKPLITRFVRIKPATWETGISMRFE 420
421 VYGCKITDYPCSGMLGMVSGLISDSQITSSNQGDRNWMPENIRLVTSRSGWALPPAPHSYINEWLQIDLG 490
491 EEKIVRGIIIQGGKHRENKVFMRKFKIGYSNNGSDWKMIMDDSKRKAKSFEGNNNYDTPELRTFPALSTR 560
561 FIRIYPERATHGGLGLRMELLGCEVEAPTAGPTTPNGNLVDECDDDQANCHSGTGDDFQLTGGTTVLATE 630
631 KPTVIDSTIQSEFPTYGFNCEFGWGSHKTFCHWEHDNHVQLKWSVLTSKTGPIQDHTGDGNFIYSQADEN 700
701 QKGKVARLVSPVVYSQNSAHCMTFWYHMSGSHVGTLRVKLRYQKPEEYDQLVWMAIGHQGDHWKEGRVLL 770
771 HKSLKLYQVIFEGEIGKGNLGGIAVDDISINNHISQEDCAKPADLDKKNPEIKIDETGSTPGYEGEGEGD 840
841 KNISRKPGNVLKTLDPILITIIAMSALGVLLGAVCGVVLYCACWHNGMSERNLSALENYNFELVDGVKLK 910
911 KDKLNTQSTYSEA 923
```

FIG. 3

COMPARATIVE DEDUCED AMINO ACID SEQUENCES OF HUMAN $VEGF_{165}$R/NP AND $VEGF_{165}$R/NP-1

| | | | |
|---|---|---|---|
| $VEGF_{165}$R/NP-2 | 1 | MDMF-PLTW-VFLALYFSRHQVRGQPOPPCGG-RLNSK--DA------GY | 50 |
| $VEGF_{165}$R/NP-1 | | MERGLPLLCAV-LAL------VLA-PA---GAFR-NDKCGDTIKIESPGY | |
| NP-2 | 51 | ITSPGYPQDY-PSHQNCEW-IVYAPEPNQKIVLNFNPEFEIEKHDCKYDF | 100 |
| NP-1 | | LTSPGYPHSYHPSEK-CEWLIQ-APDPYQRIMINFNPHFDLEDRDCXYDY | |
| NP-2 | 101 | IEIRDGDSESADLLGKHCGNIAPPTIISSGSMLYIKFTSDYARQGAGFSL | 150 |
| NP-1 | | VEVFDGENENGHFRGKFCGKIAPPPVVSSGPFLFIKFVSDYETHGAGFSI | |
| NP-2 | 151 | RYEIFKTGSEDCSKNFTSPNGTIESPGFPEKYPHN-LDCTFTIL-AKPKM | 200 |
| NP-1 | | RYEIFKRGPE-CSQNYTTPSGVIKSPGFPEKYP-NSLECTY-IVFA-PKM | |
| NP-2 | 201 | -EIILQFLIFDLEHD--PLQVGEGD-CKYDWLDIWDGIPHVGPLIGKYCG | 250 |
| NP-1 | | SEIILEFESFDLEPDSNPP--G-GMFCRYDRLEIWDGFPDVGPHIGRYCG | |
| NP-2 | 251 | TKTPSELRSSTGILSLTFHTDMAVAKDGFSARYYLVHQEPL-ENFQCNVP | 300 |
| NP-1 | | QKTPGRIRSSSGILSMVPYTDSAIAKEGFSANYS-VLQSSVSEDFKCMEA | |
| NP-2 | 301 | LGMESGAIANEQISASSTYSDGRWTPQQSRLHGDDNGWTPNLDSNKEYLQ | 350 |
| NP-1 | | LGMESGEIHSDQITASSQYSTN-WSAERSRLNYPENGWTPGEDSYREWIQ | |
| NP-2 | 351 | VDL---RFLTMLTAIATQGAISRETQNGYYVKSYKLEVSTNGEDWMVYRH | 400 |
| NP-1 | | VDLGLURFVT---AVGTQGAISKETKKKYYVKTYKIDVSSNGEDWITIKE | |
| NP-2 | 401 | GKNHK-V-FQAN-NDATEVVLN---KLHAPLLTRFVRIRPQTWHSGIALR | 450 |
| NP-1 | | G-N-KPVLFQGNTNP-TDVVVAVFPK---PLITRFVRIKPATWETGISMR | |
| NP-2 | 451 | LELFGCRVTDAPCSMKLGMLSGLIADSQISASSTQEYL-WSPSAARLVSS | 500 |
| NP-1 | | FEVYGCKITDYPCSGMLGMVSGLISDSQIT-SSNQGDRNWMPENIRLVTS | |

| FIG. 4A |
|---|
| FIG. 4B |

```
NP-2 501  RSGWF-PRIPQAQPGE---EWLQVDLGTPKTVKGVIIQGARGGDSITAVE 550
NP-1      RSGWALP--P-A-PHSYINEWLQIDLGEEKIVRGIIIQG--GKHRENKV-

NP-2 551  ARAFVRKFKVSYSLNGKDWEYIQDP--RTQQPKLFEGNMHYDTPDIRRFD 600
NP-1      ---FMRKFKIGYSNNGSDWKMIMDDSKRKA--KSFEGNNNYDTPELRTF-

NP-2 601  PIPAQYVRV---YPERWSPA--GI-GMRLEVLGCDWTDSKPTVE--TLGP 650
NP-1      P--ALSTRFIRIYPER---AFHGGLGLRMELLGCE-------VEAPTAGP

NP-2 651  TVKSEETTTPYPTEEEATECGE---NC-SFE-DDKDLQ-----L----P- 700
NP-1      T-----T--PNGNLVD--ECDDDQANCHSGTGDDFQLTGGTTVLATEKPT

NP-2 701  ---S---------GFNCNFD------FLEEPCGWMYD-BA--KW--LRTT 750
NP-1      VIDSTIQSEFPTYGFNCEFGWGSHKTF----CHWEHDNHVQLKNSVL-T-

NP-2 751  WASSSSPN-DRTFPDDRNFLRLQSDS-QREGQYARLISPPVHLPRSPVCM 800
NP-1      --SKTGPIQDHTG-DG-NFIYSQADENQK-GKVARLVSPVVYSQNSAHCM

NP-2 801  EFQYQATG---G--RGVAL--QVVREASQESKLLWV-IREDQGGEWKHGR 850
NP-1      TFWYHMSGSHVGTLR-VKLRYQKPEEYDQ---LVWMAIGH-QGDHWKEGR

NP-2 851  IILP-SYDMEYQ-IVFEGVIGKGRSGEIAIDOIRI----STDVPLENCME 900
NP-1      VLLHKSLKL-YQVI-FEGEIGKGNLGGIAVDDISINNHISQ----EDCAK

NP-2 901  PISAFAGENFKVDIPEIHERE-G----YEDEIDDEYEVDWSNSSSATSGS 950
NP-1      P--ADLDK--KN--PEIKIDETGSTPGYEGEG--EG--DK-NISRKP-GN

NP-2 951  GAPSTDKEKSWLYTLDPILITIIAMSSLGVLLGATCAGLLLYCTCSYSGL 1000
NP-1      VL----K------TLDPILITIIAMSALGVLLGAVC-GVVLYCACWHNGM

NP-2 1001 SSR--SCTTLENYNFELYDG--LKHKVKMNHQKCCSEA 1038
NP-1      SERNLSA--LENYNFELVDGVKLK-KDKLNTQSTYSEA
```

FIG. 4B

HUMN NEUROPILIN-2 AMINO ACID SEQUENCE:

MDMFPLTWVFLALYFSRHQVRGQPDPPCGGRLNSKDAGYITSPGYPQDYPSHQN
CEWIVYAPEPNQKIVLNFNPHFEIEKHDCKYDFIEIRDGDSESADLLGKHCGNIAPP
TIISSGSMLYIKFTSDYARQGAGFSLRYEIFKTGSEDCSKNFTSPNGTIESPGFPEK
YPHNLDCTFTILAKPKMEIILQFLIFDLEHDPLQVGEGDCKYDWLDIWDGIPHVGPL
IGKYCGTKTPSELRSSTGILSLTFHTDMAVAKDGFSARYYLVHQEPLENFQCNVP
LGMESGRIANEQISASSTYSDGRWTPQQSRLHGDDNGWTPNLDSNKEYLQVDLR
FLTMLTAIATQGAISRETQNGYYVKSYKLEVSTNGEDWMVYRHGKNHKVFQANN
DATEVVLNKLHAPLLTRFVRIRPQTWHSGIALRLELFGCRVTDAPCSNMLGMLS
GLIADSQISASSTQEYLWSPSAARLVSSRSGWFPRIPQAQPGEEWLQVDLGTPK
TVKGVIIGGARGGDSITAVEARAFVRKFKVSYSLNGKDWEYIQDPRTQQPKLFEG
NMHYDTPDIRRFDPIPAQYVRVYPERWSPAGIGMRLEVLGCDWTDSKPTVETLG
PTVKSEETTTPYPTEEEATECGENCSFEDDKDLQLPSGFNCNFDFLEEPCGWMYD
HAKWLRTTWASSSSPNDRTFPDDRNFLRLQSDSQREGQYARLISPPVHLPRSPV
CMEFQYQATGGRGVALQVVREASQESKLLWVIREDQGGEWKHGRIILPSYDMEYQ
IVFEGVIGKGRSGEIAIDDIRISTDVPLENCMEPISAFAGENFKVDIPEIHEREGYED
EIDDEYEVDWSNSSSATSGSGAPSTDKEKSWLYTLDPILITIIAMSSLGVLLGAT
GAGLLLYCTCSYSGLSSRSCTTLENYNFELYDGLKHKVKMNHQKCCSEA*

FIG. 12

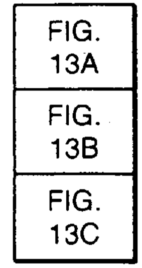

FIG. 13

```
gaattcggca cgaggggaaa ataaaagaga gaaaaacaca aagatttaaa caagaaacct     60
acgaacccag ctctggaaag agccaccttc tccaaaatgg atatgtttcc tctcacctgg    120
gttttcttag ccctctactt ttcaagacac caagtgagag gccaaccaga cccaccgtgc    180
ggaggtcgtt tgaattccaa agatgctggc tatatcacct ctcccggtta cccccaggac    240
tacccctccc accagaactg cgagtggatt gtttacgccc ccgaacccaa ccagaagatt    300
gtcctcaact tcaaccctca ctttgaaatc gagaagcacg actgcaagta tgactttatc    360
gagattcggg atggggacag tgaatccgca gacctcctgg gcaaacactg tgggaacatc    420
gccccgccca ccatcatctc ctcgggctcc atgctctaca tcaagttcac ctccgactac    480
gcccggcagg gggcaggctt ctctctgcgc tacgagatct tcaagacagg ctctgaagat    540
tgctcaaaaa acttcacaag ccccaacggg accatcgaat ctcctgggtt tcctgagaag    600
tatccacaca acttggactg cacctttacc atcctggcca aacccaagat ggagatcatc    660
ctgcagttcc tgatctttga cctggagcat gaccctttgc aggtgggaga gggggactgc    720
aagtacgatt ggctggacat ctgggatggc attccacatg ttggccccct gattggcaag    780
tactgtggga ccaaaacacc ctctgaactt cgttcatcga cggggatcct ctccctgacc    840
tttcacacgg acatggcggt ggccaaggat ggcttctctg cgcgttacta cctggtccac    900
caagagccac tagagaactt tcagtgcaat gttcctctgg gcatggagtc tggccggatt    960
gctaatgaac agatcagtgc ctcatctacc tactctgatg ggaggtggac ccctcaacaa   1020
agccggctcc atggtgatga caatggctgg acccccaact tggattccaa caaggagtat   1080
ctccaggtgg acctgcgctt tttaaccatg ctcacggcca tcgcaacaca gggagcgatt   1140
tccagggaaa cacagaatgg ctactacgtc aaatcctaca agctggaagt cagcactaat   1200
```

FIG. 13A

```
ggagaggact ggatggtgta ccggcatggc aaaaaccaca aggtatttca agccaacaac   1260
gatgcaactg aggtggttct gaacaagctc cacgctccac tgctgacaag gtttgttaga   1320
atccgccctc agacctggca ctcaggtatc gccctccggc tggagctctt cggctgccgg   1380
gtcacagatg ctccctgctc caacatgctg gggatgctct caggcctcat tgcagactcc   1440
cagatctccg cctcttccac ccaggaatac ctctggagcc ccagtgcagc ccgcctggtc   1500
agcagccgct cgggctggtt ccctcgaatc cctcaggccc agcccggtga ggagtggctt   1560
caggtagatc tgggaacacc caagacagtg aaaggtgtca tcatccaggg agcccgcgga   1620
ggagacagta tcactgctgt ggaagccaga gcatttgtgc gcaagttcaa agtctcctac   1680
agcctaaacg gcaaggactg ggaatacatt caggacccca ggacccagca gccaaagctg   1740
ttcgaaggga acatgcacta tgacacccct gacatccgaa ggtttgaccc cattccggca   1800
cagtatgtgc gggtataccc ggagaggtgg tcgccggcgg ggattgggat gcggctggag   1860
gtgctgggct gtgactggac agactccaag cccacggtag agacgctggg acccactgtg   1920
aagagcgaag agacaaccac cccctacccc accgaagagg aggccacaga gtgtggggag   1980
aactgcagct ttgaggatga caaagatttg cagctccctt cgggattcaa ttgcaacttc   2040
gatttcctcg aggagccctg tggttggatg tatgaccatg ccaagtggct ccggaccacc   2100
tgggccagca gctccagccc aaacgaccgg acgtttccag atgacaggaa tttcttgcgg   2160
ctgcagagtg acagccagag agagggccag tatgcccggc tcatcagccc ccctgtccac   2220
ctgccccgaa gcccggtgtg catggagttc cagtaccagg ccacgggcgg ccgcggggtg   2280
gcgctgcagg tggtgcggga agccagccag gagagcaagt tgctgtgggt catccgtgag   2340
gaccagggcg gcgagtggaa gcacgggcgg atcatcctgc ccagctacga catggagtac   2400
```

FIG. 13B

```
cagattgtgt tcgagggagt gatagggaaa ggacgttccg gagagattgc cattgatgac   2460
attcggataa gcactgatgt cccactggag aactgcatgg aacccatctc ggcttttgca   2520
ggtgagaatt ttaaagtgga catcccagaa atacatgaga gagaaggata tgaagatgaa   2580
attgatgatg aatacgaggt ggactggagc aattcttctt ctgcaacctc agggtctggc   2640
gccccctcga ccgacaaaga aaagagctgg ctgtacaccc tggatcccat cctcatcacc   2700
atcatcgcca tgagctcact gggcgtcctc ctgggggcca cctgtgcagg cctcctgctc   2760
tactgcacct gttcctactc gggcctgagc tcccgaagct gcaccacact ggagaactac   2820
aacttcgagc tctacgatgg ccttaagcac aaggtcaaga tgaaccacca aaagtgctgc   2880
tccgaggcat gacggattgc acctgaatcc tatctgacgt ttcattccag caagaggggc   2940
tggggaagat tacatttttt tttcctttgg aaactgaatg ccataatctc gatcaaaccg   3000
atccagaata ccgaaggtat ggacaggaca gaaaagcgag tcgcaggagg aagggagatg   3060
cagccgcaca ggggatgatt accctcctag gaccgcggtg gctaagtcat tgcaggaacg   3120
gggctgtgtt ctctgctggg acaaaacagg agctcatctc tttggggtca cagttctatt   3180
ttgtttgtga gtttgtatta ttattattat tattattatt atatttattt tctttggtct   3240
gtgagcaact caaagaggca gaagaggaga atgacttttc cagaatagaa gtggagcagt   3300
gatcattatt ctccgctttc tctttctaat caacacttga aaagcaaagt gtcttttcag   3360
cctttccatc tttacaaata.aaactcaaaa aagctgtcca gctt                    3404
```

FIG. 13C

```
        247         256         265         274         283         292
ATG GAG AGG GGG CTG CCG CTC CTC TGC GCC GTG CTC GCC CTC GTC CTC GCC CCG
--- --- --- --- --- --- --- --- --- --- --- --- --- --- --- --- --- ---
 M   E   R   G   L   P   L   L   C   A   V   I   A   L   V   L   A   P

        301         310         319         328         337         346
GCC GGC GCT TTT CGC AAC GAT AAA TGT GGC GAT ACT ATA AAA ATT GAA AGC CCC
--- --- --- --- --- --- --- --- --- --- --- --- --- --- --- --- --- ---
 A   G   A  |F   R->a1 N  D   K   C   G   D   T   I   K   I   E   S   P

        355         364         373         382         391         400
GGG TAC CTT ACA TCT CCT GGT TAT CCT CAT TCT TAT CAC CCA AGT GAA AAA TGC
--- --- --- --- --- --- --- --- --- --- --- --- --- --- --- --- --- ---
 G   Y   L   T   S   P   G   Y   P   H   S   Y   H   P   S   E   K   C

        409         418         427         436         445         454
GAA TGG CTG ATT CAG GCT CCG GAC CCA TAC CAG AGA ATT ATG ATC AAC TTC AAC
--- --- --- --- --- --- --- --- --- --- --- --- --- --- --- --- --- ---
 E   W   L   I   Q   A   P   D   P   Y   Q   R   I   M   I   N   F   N

        463         472         481         490         499         508
CCT CAC TTC GAT TTG GAG GAC AGA GAC TGC AAG TAT GAC TAC GTG GAA GTG TTC
--- --- --- --- --- --- --- --- --- --- --- --- --- --- --- --- --- ---
 P   H   H   D   L   E   D   R   D   C   K   Y   D   Y   V   E   V   F

        517         526         535         544         553         562
GAT GGA GAA AAT GAA AAT GGA CAT TTT AGG GGA AAG TTC TGT GGA AAG ATA GCC
--- --- --- --- --- --- --- --- --- --- --- --- --- --- --- --- --- ---
 D   G   E   N   E   N   G   H   P   R   G   K   F   C   C   K   I   A

        571         580         589         598         607         616
CCT CCT CCT GTT GTG TCT TCA GGG CCA TTT CTT TTT ATC AAA TTT GTC TCT GAC
--- --- --- --- --- --- --- --- --- --- --- --- --- --- --- --- --- ---
 P   P   P   V   V   S   S   G   P   F   L   F   I   K   F   V   S   D

        625         634         643         652         661         670
TAC GAA ACA CAT GGT GCA GGA TTT TCC ATA CGT TAT GAA ATT TTC AGG AGA GGT
--- --- --- --- --- --- --- --- --- --- --- --- --- --- --- --- --- ---
 Y   E   T   H   G   A   G   F   S   I   R   Y   E   I   F   K   R   G

        679         688         697         706         715         724
CCT GAA TGT TCC CAG AAC TAC ACA ACA CCT AGT GGA GTG ATA AAG TCC CCC GGA
--- --- --- --- --- --- --- --- --- --- --- --- --- --- --- --- --- ---
 P   E ||C   S   Q   N   Y   T   T   P   S   G   V   I   K   S   P   G
  a1<--||-->a2
```

FIG. 14A

| FIG. 14A |
| --- |
| FIG. 14B |
| FIG. 14C |
| FIG. 14E |
| FIG. 14F |

FIG. 14

```
        733         742         751         760         769         778
TTC CCT GAA AAA TAT CCC AAC AGC CTT GAA TGC ACT TAT ATT GTC TTT GCG CCA
--- --- --- --- --- --- --- --- --- --- --- --- --- --- --- --- --- ---
 F   P   E   K   Y   P   N   S   L   E   C   T   Y   I   V   F   A   P

        787         796         805         814         823         832
AAG ATG TCA GAG ATT ATC CTG GAA TTT GAA AGC TTT GAC CTG GAG CCT GAC TCA
--- --- --- --- --- --- --- --- --- --- --- --- --- --- --- --- --- ---
 K   M   S   E   I   I   L   E   F   E   S   T   D   L   E   P   D   S

        841         850         859         868         877         886
AAT CCT CCA GGG GGG ATG TTC TGT CGC TAC GAC CGG CTA GAA ATC TGG GAT GGA
--- --- --- --- --- --- --- --- --- --- --- --- --- --- --- --- --- ---
 N   P   P   G   G   M   F   C   R   Y   D   R   L   T   I   W   D   G

        895         904         913         922         931         940
TTC CCT GAT GTT GGC CCT CAC ATT GGG CGT TAC TGT GGA CAG AAA ACA CCA GGT
--- --- --- --- --- --- --- --- --- --- --- --- --- --- --- --- --- ---
 F   P   D   V   G   P   H   I   G   R   Y   C   G   Q   K   T   P   G

        949         958         957         976         985         994
CGA ATC CGA TCC TCA TCG GGC ATT CTC TCC ATG GTT TTT TAC ACC GAC AGC GCG
--- --- --- --- --- --- --- --- --- --- --- --- --- --- --- --- --- ---
 R   I   R   S   S   S   G   I   L   S   M   V   H   Y   T   D   S   A

       1003        1012        1021        1030        1039        1048
ATA GCA AAA GAA GGT TTC TCA GCA AAC TAC AGT GTC TTG CAG AGC AGT GTC TCA
--- --- --- --- --- --- --- --- --- --- --- --- --- --- --- --- --- ---
 I   A   K   E   G   F   S   A   N   Y   S   V   L   Q   S   S   V   S

       1057        1066        1075        1084        1093        1102
GAA GAT TTC AAA TGT ATG GAA GCT CTG GGC ATG GAA TCA GGA GAA ATT CAT TCT
--- --- --- --- --- --- --- --- --- --- --- --- --- --- --- --- --- ---
 E   D   F   K   C   M   C   A   L   G   M   E   S   G   E   I   H   S
      a2<-        ->b1
       1111        1120        1129        1138        1147        1156
GAC CAG ATC ACA GCT TCT TCC CAG TAT AGC ACC AAC TGG TCT GCA GAG CGC TCC
--- --- --- --- --- --- --- --- --- --- --- --- --- --- --- --- --- ---
 D   Q   I   T   A   S   S   Q   Y   S   T   N   W   S   A   E   R   S

       1165        1174        1183        1192        1201        1210
CGC CTG AAC TAC CCT GAG AAT GGG TGG ACT CCC GGA GAG GAT TCC TAC CGA GAG
--- --- --- --- --- --- --- --- --- --- --- --- --- --- --- --- --- ---
 R   L   N   Y   P   E   N   G   W   T   P   G   E   D   S   Y   R   E
```

FIG. 14B

```
         1219        1228        1237        1246        1255        1264
TGG ATA CAG GTA GAC TTG GGC CTT CTG CGC TTT GTC ACG GCT GTC GGG ACA CAG
--- --- --- --- --- --- --- --- --- --- --- --- --- --- --- --- --- ---
 W   I   Q   V   D   L   G   L   L   R   F   V   T   A   V   G   T   Q

         1273        1282        1291        1300        1309        1318
GGC GCC ATT TCA AAA GAA ACC AAG AAG AAA TAT TAT GTC AAG ACT TAC AAG ATC
--- --- --- --- --- --- --- --- --- --- --- --- --- --- --- --- --- ---
 G   A   I   S   K   E   T   K   K   K   Y   Y   V   K   T   Y   K   I

         1327        1336        1345        1354        1363        1372
GAC GTT AGC TCC AAC GGG GAA GAC TGG ATC ACC ATA AAA GAA GGA AAC AAA CCT
--- --- --- --- --- --- --- --- --- --- --- --- --- --- --- --- --- ---
 D   V   S   S   N   G   E   D   W   I   I   I   K   E   G   N   K   P

         1381        1390        1399        1408        1417        1426
GTT CTC TTT CAG GGA AAC ACC AAC CCC ACA GAT GTT GTG GTT GCA GTA TTC CCC
--- --- --- --- --- --- --- --- --- --- --- --- --- --- --- --- --- ---
 V   L   F   Q   G   N   T   N   P   T   D   V   V   V   A   V   F   P

         1435        1444        1453        1462        1471        1480
AAA CCA CTG ATA ACT CGA TTT GTC CGA ATC AAG CCT GCA ACT TGG GAA ACT GGC
--- --- --- --- --- --- --- --- --- --- --- --- --- --- --- --- --- ---
 K   P   L   I   T   R   F   V   R   I   K   P   A   T   W   E   T   G

         1489        1498        1507        1516        1525        1534
ATA TCT ATG AGA TTT GAA GTA TAC GGT TGC AAG ATA ACA GAT TAT CCT TGC TCT
--- --- --- --- --- --- --- --- --- --- --- --- --- --- --- ---||--- ---
 I   S   M   R   F   E   V   Y   G   C   K   I   T   D   Y b1<-P||C->b2 S

         1543        1552        1561        1570        1579        1588
GGA ATG TTG GGT ATG GTG TCT GGA CTT ATT TCT GAC TCC CAG ATC ACA TCA TCC
--- --- --- --- --- --- --- --- --- --- --- --- --- --- --- --- --- ---
 G   M   L   G   M   V   S   G   L   I   S   D   S   Q   I   T   S   S

         1597        1606        1615        1624        1633        1642
AAC CAA GGG GAC AGA AAC TGG ATG CCT GAA AAC ATC CGC CTG GTA ACC AGT CGC
--- --- --- --- --- --- --- --- --- --- --- --- --- --- --- --- --- ---
 N   Q   G   D   R   N   W   M   P   E   N   I   R   L   V   T   S   R

         1651        1660        1669        1678        1687        1696
TCT GGC TGG GCA CTT CCA CCC GCA CCT CAT TCC TAC ATC AAT GAG TGG CTC CAA
--- --- --- --- --- --- --- --- --- --- --- --- --- --- --- --- --- ---
 S   G   W   A   L   P   P   A   P   H   S   Y   I   N   C   W   L   Q
```

FIG. 14C

```
         1705          1714          1723          1732          1741          1750
ATA GAC CTG GGG GAC GAG AAG ATC GTG AGG GGG ATC ATC ATT CAG GGT GGG AAG
 I   D   L   G   E   E   K   I   V   R   G   I   I   I   Q   G   G   X

         1759          1768          1777          1786          1795          1804
CAC CGA GAG AAC AAG GTG TTC ATG AGG AAG TTC AAG ATC GGG TAC AGC AAC AAC
 R   R   E   N   K   V   F   H   R   K   F   K   I   G   Y   S   N   N

         1813          1822          1831          1840          1849          1858
GGC TCG GAC TGG AAG ATG ATC ATG GAT GAC AGC AAA CGC AAG GCG AAG TCT TTT
 G   S   D   W   K   M   I   M   D   D   S   K   R   K   A   K   S   F

         1867          1876          1885          1894          1903          1912
GAG GGC AAC AAC AAC TAT GAT ACA CCT GAG CTG CGG ACT TTT CCA GCT CTC TCC
 E   G   N   N   N   Y   D   T   P   E   L   R   T   F   P   A   L   S

         1921          1930          1939          1948          1957          1966
ACG CGA TTC ATC AGG ATC TAC CCC GAG AGA GCC ACT CAT GGC GGA CTG GGG CTC
 T   R   F   I   R   I   Y   P   F   R   A   T   H   G   G   L   G   L

         1975          1984          1993          2002          2011          2020
AGA ATG GAG CTG CTG GGC TGT GAA GTG GAA GCC CCT ACA GGT GGA CCG ACC ACT
 R   N   E   L   L   G   C   E   V   E   A | P   T   A   G   P   T   T
                                          b2<-

         2029          2038          2047          2056          2065          2074
CCC AAC GGG AAC TTG GTG GAT GAA TGT GAT GAC GAC CAG GCC AAC TGC CAC AGT
 P   N   G   N   L   V   D   E   C   D   D   D   Q  -A   N   C   H   S

         2083          2092          2101          2110          2119          2128
GGA ACA GGT GAT GAC TTC CAG CTC ACA GGT GGC ACC ACT GTG CTG GCC ACA GAA
 G   T   G   D   D   F   Q   L   T   G   G   T   T   V   L   A   T   E

         2137          2146          2155          2154          2173          2182
AAG CCC ACG GTC ATA GAC AGC ACC ATA CAA TCA GAG TTT CCA ACA TAT GGT TTT
 K   P   T   V   I   D   S   T   I   Q   S   E   F   P   T   Y | G   F
                                                                ->c
```

FIG. 14D

```
            2191            2200            2209            2218            2227            2236
AAC TGT GAA TTT GGC TGG GGC TCT CAC AGG ACC TTC TGC CAC TGG GAA CAT GAC
 N   C   t   F   G   W   G   S   H   K   T   F   C   H   W   E   H   D

            2245            2254            2263            2272            2281            2290
AAT CAC GTG CAG CTC AAG TGG AGT GTG TTG ACC AGC AAG ACG GGA CCC ATT CAG
 N   H   V   Q   L   K   W   S   V   L   T   S   K   T   G   P   I   Q

            2299            2308            2317            2326            2335            2344
GAT CAC ACA GGA GAT GGC AAC TTC ATC TAT TCC CAA GCT GAC GAA AAT CAG AAG
 D   H   T   G   D   G   N   F   I   Y   S   Q   A   D   E   N   Q   K

            2353            2362            2371            2380            2389            2398
GGC AAA GTG GCT CGC CTG GTG AGC CCT GTG GTT TAT TCC CAG AAC TCT GCC CAC
 G   K   V   A   R   L   V   S   P   V   V   Y   S   Q   N   S   A   H

            2407            2416            2425            2434            2443            2452
TGC ATG ACC TTC TGG TAT CAC ATG TCT GGG TCC CAC GTC GGC ACA CTC AGG GTC
 C   M   T   F   W   Y   H   M   S   G   S   H   V   G   T   L   R   V

            2461            2470            2479            2488            2497            2506
AAA CTG CGC TAC CAG AAG CCA GAG GAG TAC GAT GAG GTG GTC TGG ATG GCC ATT
 K   L   R   Y   Q   K   P   E   E   Y   D   Q   L   V   W   M   A   I

            2515            2524            2533            2542            2551            2560
GGA CAC CAA GGT GAC CAC TGG AAG GAA GGG CGT GTC TTG CTC CAC AAG TCT CTG
 G   H   Q   G   D   H   W   K   E   G   R   V   L   L   H   K   S   L

            2569            2578            2587            2596            2605            2614
AAA CTT TAT CAG GTG ATT TTC GAG GGC GAA ATC GGA AAA GGA AAC CTT GGT GGG
 K   L   Y   Q   Y   I   F   E   G   E   I   G   K   G   N   L   G   G

            2623            2632            2641            2650            2659            2668
ATT GCT GTG GAT GAC ATT AGT ATT AAC AAC CAC ATT TCA CAA GAA GAT TGT GCA
 I   A   Y   D   D   I   S   I   N   N   H   I   S   Q   E   D   C | A
                                                                 c<--
```

FIG. 14E

```
          2677                2686                2695                2704                2713                2722
AAA  CCA  GCA  GAC  CTG  GAT  AAA  AAG  AAC  CCA  GAA  ATT  AAA  ATT  GAT  GAA  ACA  GGG
---  ---  ---  ---  ---  ---  ---  ---  ---  ---  ---  ---  ---  ---  ---  ---  ---  ---
 K    P    A    D    L    D    K    K    N    P    E    I    K    I    D    E    T    G

          2731                2740                2749                2758                2767                2776
AGC  ACG  CCA  GGA  TAC  GAA  GGT  GAA  GGA  GAA  GGT  GAC  AAG  AAC  ATC  TCC  AGG  AAG
---  ---  ---  ---  ---  ---  ---  ---  ---  ---  ---  ---  ---  ---  ---  ---  ---  ---
 S    T    P    G    Y    E    G    E    G    E    G    D    K    N    I    S    R    K

          2785                2794                2803                2812                2821                2830
CCA  GGC  AAT  GTG  TTG  AAG  ACC  TTA  GAT  CCC  ATC  CTC  ATC  ACC  ATC  ATA  GCC  ATG
---  ---  ---  ---  ---  ---  ---  ---  ---  ---  ---  ---  ---  ---  ---  ---  ---  ---
 P    G    N    V    L    K    T    L    D    P    I->TM I  I    T    I    I    A    M

          2839                2848                2857                2866                2875                2884
AGT  GCC  CTG  GGG  GTC  CTC  CTG  GGG  GCT  GTC  TGT  GGG  GTC  GTG  CTG  TAC  TGT  GCC
---  ---  ---  ---  ---  ---  ---  ---  ---  ---  ---  ---  ---  ---  ---  ---  ---  ---
 S    A    L    G    V    L    L    G    A    V    C    G    V    V    L    Y    C    A

          2893                2902                2911                2920                2929                2938
TGT  TGG  CAT  AAT  GGG  ATG  TCA  GAA  AGA  AAC  TTG  TCT  GCC  CTG  GAG  AAC  TAT  AAC
---  ---  ---  ---  ---  ---  ---  ---  ---  ---  ---  ---  ---  ---  ---  ---  ---  ---
 C TM<-W || H->cyto N  G    M    S    E    R    N    L    S    A    L    E    N    Y    N

          2947                2956                2965                2974                2983                2997
TTT  GAA  CTT  GTG  GAT  GGT  GTG  AAG  TTG  AAA  AAA  GAC  AAA  CTG  AAT  ACA  CAG  AGT
---  ---  ---  ---  ---  ---  ---  ---  ---  ---  ---  ---  ---  ---  ---  ---  ---  ---
 F    E    L    V    D    G    V    K    L    K    K    D    K    L    N    T    Q    S

          3001                3010
ACT  TAT  TCG  GAG  GCA  TGA  3'  (SEQ ID NO: 1)
---  ---  ---  ---  ---  ---
 T    Y    S    E cyto<-A  *       (SEQ ID NO: 2)
```

FIG. 14F

ANTAGONISTS OF NEUROPILIN RECEPTOR FUNCTION AND USE THEREOF

CROSS-REFERENCE TO RELATED APPLICATIONS

This application is a continuation of U.S. Ser. No. 10/104,440, filed Mar. 22, 2002 which is a continuation of U.S. Ser. No. 09/580,803 filed on May 30, 2000 now abandoned, which is a continuation of International Application PCT/US98/26114 filed on Dec. 9, 1998 which designates the U.S. and claims priority benefits of U.S. Provisional Application Ser. Nos. 60/069,155 filed on Dec. 9, 1997, 60/069,687 filed on Dec. 12, 1997 and 60/078,541 filed on Mar. 19, 1998, all of which are incorporated herein by reference.

STATEMENT REGARDING FEDERALLY SPONSORED RESEARCH

The work described herein was supported, in part, by National Institute of Health grants CA37392 and CA45548. The U.S. Government has certain rights to the invention.

FIELD OF THE INVENTION

The present invention relates to antagonists of neuropilin receptor function and use thereof in the treatment of cancer, particularly metastatic cancer, and angiogenic diseases.

BACKGROUND OF THE INVENTION

Cancer, its development and treatment is a major health concern. The standard treatments available are few and directed to specific types of cancer, and provide no absolute guarantee of success. Most treatments rely on an approach that involves killing off rapidly growing cells in the hope that rapidly growing cancerous cells will succumb, either to the treatment, or at least be sufficiently reduced in numbers to allow the body's system to eliminate the remainder. However most of these treatments are non-specific to cancer cells and adversely effect non-malignant cells. Many cancers although having some phenotype relationship are quite diverse. Yet, what treatment works most effectively for one cancer may not be the best means for treating another cancer. Consequently, an appreciation of the severity of the condition must be made before beginning many therapies. In order to most effective, these treatments require not only an early detection of the malignancy, but an appreciation of the severity of the malignancy. Currently, it can be difficult to distinguish cells at a molecular level as it relates to effect on treatment. Thus, methods of being able to screen malignant cells and better understand their disease state are desirable.

While different forms of cancer have different properties, one factor which many cancers share is that they can metastasize. Until such time as metastasis occurs, a tumor, although it may be malignant, is confined to one area of the body. This may cause discomfort and or pain, or even lead to more serious problems including death, but if it can be located, it may be surgically removed and, if done with adequate care, be treatable. However, once metastasis sets in, cancerous cells have invaded the body and while surgical resection may remove the parent tumor, this does not address other tumors. Only chemotherapy, or some particular form of targeting therapy, then stands any chance of success.

The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., *Adv. Cancer Res.* 28, 149-250 (1978). Liotta, et al., *Cancer Treatment Res.* 40, 223-238 (1988). Nicolson, *Biochim. Biophy. Acta* 948, 175-224 (1988) and Zetter, *N. Eng. J. Med.* 322, 605-612 (1990)). Success in establishing metastatic deposits requires tumor cells to be able to accomplish these steps sequentially. Common to many steps of the metastatic process is a requirement for motility. The enhanced movement of malignant tumor cells is a major contributor to the progression of the disease toward metastasis. Increased cell motility has been associated with enhanced metastatic potential in animal as well as human tumors (Hosaka. et al., *Gann* 69, 273-276 (1978) and Haemmerlin, et al., *Int. J. Cancer* 27, 603-610 (1981)).

Identifying factors that are associated with onset of tumor metastasis is extremely important. In addition, to using such factors for diagnosis and prognosis, those factors are an important site for identifying new compounds that can be used for treatment and as a target for treatment identifying new modes of treatment such as inhibition of metastasis is highly desirable.

Tumor angiogenesis is essential for both primary tumor expansion and metastatic tumor spread, and angiogenesis itself requires ECM degradation (Blood et al., *Biochim. Biophys. Acta.* 1032:89-118 (1990)). Thus, malignancy is a systemic disease in which interactions between the neoplastic cells and their environment play a crucial role during evolution of the pathological process (Fidler, I. *J. Cancer Metastasis Rev.* 5:29-49 (1986)).

There is mounting evidence that VEGF may be a major regulator of angiogenesis (reviewed in Ferrara. et al., *Endocr. Rev.* 13, 18-32(1991): Klagsbrun, et al., *Curr. Biol.,* 3, 699-702 (1993); Ferrara, et al., *Biochem. Biophys. Res. Commun.,* 161, 851-858 (1989) ). VEGF was initially purified from the conditioned media of folliculostellate cells (Ferrara, et al., *Biochem. Biophys. Res. Commun.,* 161, 851-858 (1989)) and from a variety of tumor cell lines (Myoken, et al., *Proc. Natl. Acad. Sci.* USA, 88:5819-5823 (1991); Plouet, et al., *EMBO. J.,* 8:3801-3806 (1991)). VEGF was found to be identical to vascular permeability factor, a regulator of blood vessel permeability that was purified from the conditioned medium of U937 cells at the same time (Keck, et al., *Science.* 246:1309-1312 (1989)). VEGF is a specific mitogen for endothelial cells (EC) in vitro and a potent angiogenic factor in vivo. The expression of VEGF is up-regulated in tissue undergoing vascularization during embryogenesis and the female reproductive cycle (Brier, et al., *Development,* 114:521-532(1992); Shweiki, et al., *J. Clin. Invest.,* 91:2235-2243 (1993)). High levels of VEGF are expressed in various types of tumors, but not in normal tissue, in response to tumor-induced hypoxia (Shweiki, et al., *Nature* 359:843-846 (1992); Dvorak et al., *J. Exp. Med.,* 174:1275-1278 (1991); Plate, et al., *Cancer Res.,* 53:5822-5827; Ikea, et al., *J. Biol. Chem.,* 270:19761-19766(1986)). Treatment of tumors with monoclonal antibodies directed against VEGF resulted in a dramatic reduction in tumor mass due to the suppression of tumor angiogeneis (Kim, et al., *Nature,* 382:841-844 (1993)). VEGF appears to play a principle role in many pathological states and processes related to neovascularization. Regulation of VEGF expression in affected tissues could therefore be key in treatment or prevention of VEGF induced neovascularization/angiogenesis.

VEGF exists in a number of different isoforms that are produced by alternative splicing from a single gene containing eight exons (Ferrara, et al., *Endocr. Rev.* 13:18-32 (1992); Tischer, et al., *J. Biol. Chem.,* 806:11947-11954 (1991); Ferrara, et al., *Trends Cardio Med.,* 3:244-250 (1993); Polterak, et al., *J. Biol. Chem.,* 272:7151-7158 (1997)). Human VEGF isoforms consists of monomers of 121, 145, 165, 189, and 206 amino acids, each capable of making an active homodimer (Polterak et al., *J. Biol. Chem.* 272:7151-7158 (1997); Houck, et al., *Mol. Endocrinol.,* 8:1806-1814 (1991)). The $VEGF_{121}$ and $VEGF_{165}$ isoforms are the most abundant. $VEGF_{121}$ is the only VEGF isoform that does not bind to heparin and is totally secreted into the culture medium. $VEGF_{165}$ is functionally different than $VEGF_{121}$ in that it binds to heparin and cell surface heparin sulfate proteoglycans (HSPGs) and is only partially released into the culture medium (Houck, et al., *J. Biol. Chem.,* 247:28031-28037 (1992); Park, et al., *Mol. Biol. Chem.,* 4:1317-1326 (1993)). The remaining isoforms are entirely associated with cell surface and extracellular matrix HSPGs (Houck, et al., *J. Biol. Chem.,* 247:28031-28037 (1992); Park. et al., *Mol. Biol. Chem.,* 4:1317-1326 (1993)).

VEGF receptor tyrosine kinases, KDR Flk-1 and or Flt-1, are mostly expressed by EC (Terman, et al., *Biochem. Biophys. Res. Commun.,* 187:1579-1586 (1992); Shibuya, et al., *Oncogene,* 5:519-524 (1990); De Vries, et al., *Science,* 265:989-991 (1992); Gitay-Goran, et al., *J. Biol. Chem.,* 287:6003-6096 (1992); Jakeman, et al., *J. Clin. Invest.,* 89:244-253 (1992)). It appears that VEGF activities such as mitogenicity, chemotaxis, and induction of morphological changes are mediated by KDR Flk-1 but not Flt-1, even though both receptors undergo phosphorylation upon binding of VEGF (Millauer, et al., *Cell,* 72:835-846 (1993); Waltenberger, et al., *J. Biol. Chem.* 269:26988-26995 ( 1994); Seetharam, et. al., *Oncogene,* 10:135-147 (1995); Yoshida, et al., *Growth Factors,* 7:131-138 (1996)). Recently, Soker et al., identified a new VEGF receptor which is expressed on EC and various tumor-derived cell lines such as breast cancer-derived MDA-MB-231 (231 ) cells (Soker, et al., *J. Biol. Chem.,* 271:5761-5767 (1996)). This receptor requires the VEGF isoform to contain the portion encoded by exon 7. For example, although both $VEGF_{121}$ and $VEGF_{165}R$ bind to KDR/Flk-1 and Flt-1, only $VEGF_{165}$ binds to the new receptor. Thus, this is an isoform-specific receptor and has been named the $VEGF_{165}$ receptor ($VEGF_{165}R$). It will also bind the 189 and 206 isoforms. $VEGF_{165}R$ has a molecular mass of approximately 130 kDa, and it binds $VEGF_{165}$ with a Kd of about $2\times10^{-10}$M, compared with approximately $5\times10^{-12}$M for KDR/Flk-1. In structure-function analysis, it was shown directly that $VEGF_{165}$ binds to $VEGF_{165}R$ via its exon 7-encoded domain which is absent in $VEGF_{124}$ (Soker, et al., *J. Biol. Chem.,* 271:5761-57,67 (1996)). However, the function of the receptor was unclear.

Identifying the alterations in gene expression which are associated with malignant tumors, including those involved in tumor progression and angiogenesis, is clearly a prerequisite not only for a full understanding of cancer, but also to develop new rational therapies against cancer.

At further problem arises, in that the genes characteristic of cancerous cells are very often host genes being abnormally expressed. It is quite often the case that a particular protein marker for a given cancer while expressed in high levels in connection with that cancer is also expressed elsewhere throughout the body, albeit at reduced levels.

The current treatment of angiogenic diseases is inadequate. Agents which prevent continued angiogenesis, e.g. drugs (TNP-470), monoclonal antibodies, antisense nucleic acids and proteins (angiostatin and endostatin) are currently being tested. See, Battegay, *J. Mol. Med.,* 73, 333-346 (1995); Hanahan et al., *Cell,* 86,353-364 (1996); Folkman. *N. Engl. J. Med.,* 333, 1757-1763 (1995). Although preliminary results with the antiangiogenic proteins are promising, there is still a need for identifying genes encoding ligands and receptors involved in angiogenesis for the development of new antiangiogenic therapies.

SUMMARY OF THE INVENTION

We have isolated a cDNA encoding the $VEGF_{165}$ R gene (SEQ ID NO: 1) and have deduced the amino acid sequence of the receptor (SEQ ID NO:2) We have discovered that this novel VEGF receptor is structurally unrelated to Flt-1 or KDR/Flk-1 and is expressed not only, by endothelial cells but by non-endothelial cells, including surprisingly tumor cells.

In ascertaining the function of the $VEGF_{165}R$ we have further discovered that this receptor has been identified as a cell surface mediator of neuronal cell guidance and called neuropilin-1. Kolodkin et al., *Cell* 90:753-762 (1997). We refer to the receptor as $VEGF_{165}$-R/NP-1 or NP-1.

In addition to the expression cloning of $VEGF_{165}R$/NP-1 cDNA we isolated another human cDNA clone whose predicted amino acid sequence was 47% homologous to that of $VEGF_{165}R$ NP-1 and over 90% homologous to rat neuropilin-2 (NP-2) which was recently cloned (Kolodkin, et al., *Cell* 90, 753-762 (1997)).

Our results indicate that $VEGF_{165}R$ NP-1 and NP-2 are expressed by both endothelial and tumor cells. (FIG. 19) We have shown that endothelial cells expressing both KDR and $VEGF_{165}R$ NP-1 respond with increased chemotaxis towards $VEGF_{165}$, not $VEGF_{121}$, when compared to endothelial cells expressing KDR alone. While not wishing to be bound by theory, we believe that $VEGF_{165}R$/NP-1 functions in endothelial cells to mediate cell motility as a co-receptor for KDR.

We have also shown in the Boyden chamber motility assay that $VEGF_{165}$ stimulates 231 breast carcinoma cell motility in a dose-response manner (FIG. 15A). $VEGF_{121}$ had no effect motility of these cells (FIG. 15B). Since tumor cells such as, 231 cells, do not express the VEGF receptors, KDR or Flt-1, while not wishing to be bound by theory, we believe that rumor cells are directly responsive to $VEGF_{165}$ via $VEGF_{165}R$/NP-1.

We have also analyzed two variants of Dunning rat prostate carcinoma cells. AT2.1 cells, which are of low motility and low metastatic potential, and AT3.1 cells, which are highly motile, and metastatic. Cross-linking and Northern blot analysis show that AT3.1 cells express abundant $VEGF_{165}R$/NP-1, capable of binding $VEGF_{165}$, while AT2.1 cells don't express $VEGF_{165}R$/NP-1 (FIG. 18). Immunostaining of tumor sections confirmed the expression of $VEGF_{165}R$/NP-1 in AT3.1, but not AT3.1 tumors (FIG. 17). Additionally, immunostaining showed that in subcutaneous AT3.1 and PC3 tumors, the rumor cells expressing $VEGF_{165}R$/NP-1 were found preferentially at the invading front of the tumor/dermis boundary (FIG. 17). Furthermore, stable clones of AT2.1 cells overexpressing $VEGF_{165}R$/NP-1 had enhanced motility in the Boyden chamber assay. These results indicate that neuropilin expression on tumor cells is associated with the motile, metastatic phenotype and angiogenesis, and thus is an important target for antiangiogenic and anticancer therapy.

The present invention relates to antagonists of neuropilin (NP) receptor function that can be use to inhibit metastasis and angiogenesis. Antagonists of invention can block the receptor preventing ligand binding, disrupt receptor function, or inhibit receptor occurrence. Specific antagonists include, for example, compounds that bind to NP-1 or NP-2 and antibodies that specifically binds the receptor at a region that inhibits receptor function. For example, one can add an effective amount of a compound that binds to NP-1 to disrupt receptor function and thus inhibit metastasis.

We have surprisingly discovered that members of the semaphorin/collapsins family are not only inhibitors of neuronal guidance but also inhibitors of endothelial and tumor cell motility in cells that express neuropilin. Accordingly, preferred antagonists include members of the semaphorin/collapsins family or fragments thereof that bind NP and have VEGF antagonist activity as determined, for example, by the human umbilical vein endothelial cell (HUVEC) proliferation assay using $VEGF_{165}$ as set forth in Soker et al., *J. Biol. Chem.* 272, 31582-31588 (1997). Preferably, the semaphorin/collapsin has at least a 25% reduction in HUVEC proliferation, more preferably a 50% reduction, even more preferably a 75% reduction, most preferably a 95% reduction.

VEGF antagonist activity of the semaphorin collapsin may also be determined by inhibition of binding of labeled $VEGF_{165}$ to $VEGF_{165}R$ as disclosed in Soker et al., *J. Biol. Chem.* 271, 5761-5767 (1996)) or to PAE/NP cells. Preferably, the portion inhibits binding by at least 25%, more preferably 50%, most preferably 75%.

In accordance with the present invention, neuropilin antagonists, or nucleic acids, e.g., DNA or RNA, encoding such antagonists, are useful as inhibitors of VEGF and NP function and can be used to treat diseases, disorders or conditions associated with VEGF and NP expression. The antagonists can be used alone or in combination with other anti-VEGF strategies including, for example, those that antagonize VEGF directly (e.g. anti-VEGF antibodies, soluble VEGF receptor extracellular domains), or antagonize VEGF receptors (e.g. anti-KDR antibodies, KDR kinase inhibitors, dominant-negative VEGF receptors) (Presta L G, et al., Cancer Res. 57: 4593-4599 (1997), Kendall R L, et al., (1996) Biochem. Biophys. Res. Commun. 226: 324-328, Goldman C K. et at., (1998) Proc. Natl. Acad. Sci. USA 95: 8795-8800, Strawn L. M. et al., (1996) Cancer Res. 56: 3540-3545. Zhu Z. et al., (1998). Cancer Res. 58; 3209-3214, Wine L. et al., (1998). Cancer Metastasis Rev. 17: 155-161.)

Diseases, disorders, or conditions, associated with VEGF, include, but are not limited to retinal neovascularization, hemagiomas, solid tumor growth, leukemia, metastasis, psoriasis, neovascular glaucoma, diabetic retinopathy, rheumatoid arthritis, endometriosis, mucular degeneration, osteoarthritis, and retinopathy of prematurity (ROP).

In another embodiment, one can use isolated $VEGF_{165}R$/NP-1 or NP-2 or cells expressing these receptors in assays to discover compounds that bind to or otherwise interact with these receptors in order to discover NP antagonists that can be used to inhibit metastasis and/or angiogenesis.

Other aspects of the invention are disclosed infra.

BRIEF DESCRIPTION OF THE DRAWINGS

FIG. 2A shows COS 7 cells were transfected with a primary plasmid pool (#55 of the 231 cell library) representing approximately $3\times10^3$ clones and one COS 7 cell binding $^{125}I-VEGF_{165}$ in the first round of screening is shown.

FIG. 2B shows several COS 7 cells transfected with a single positive cDNA clone (A2) binding $^{125}I-VEGF_{165}$ after the third round of screening.

FIG. 3 shows the Deduced Amino Acid Sequence of Human $VEGF_{165}R$/NP-1 (SEQ ID NO:3). The deduced 923 amino acid sequence of the open reading frame of $VEGF_{165}R$/NP-1, clone A2 (full insert size of 6.5 kb) is shown. The putative signal peptide sequence (amino acids 1-21) and the putative transmembrane region (amino acids 860-883) are in boxes. The amino acid sequence obtained by N-terminal amino acid sequencing (FIG. 3, amino acids 22-39) is underlined. The arrow indicates where the signal peptide has been cleaved and removed, based on comparison of the N-terminal sequence of purified $VEGF_{165}R$/NP-1 and the cDNA sequence. The sequence of human $VEGF_{165}R$/NP-1 reported here differs from that reported by He et al. (He and Tessier-Lavigne, *Cell* 90, 739-751 (1997)) in that we find Lys-$_{26}$ rather than Glu-$_{26}$, and $Asp_{S55}$ rather than $Glu_{S55}$ $Lys_{26}$ and $Asp_{S55}$ are found, however, in mouse and rat $VEGF_{165}R$/NP-1 (Kwakami et al., *J. Neurobiol.* 29, 1-17 (1995); He and Tessier-Lavigne, *Cell* 90, 739-751 (1997)).

FIG. 4 shows the Comparison of the Deduced Amino Acid Sequence of Human $VEGF_{165}R$/NP-1 (SEQ ID NO:2) and NP-2 (SEQ ID NO:4). The deduced open reading frame amino acid sequences of $VEGF_{165}R$/NP-1 and NP-2 are aligned using the DNASIS program. Amino acids that are identical in both open reading frames are shaded. The overall homology between the two sequences is 43%.

FIG. 7A. Increasing amounts of $^{125}I-VEGF_{165}$ (0.1-50 ng ml) were added to subconfluent cultures of PAE cells transfected with human $VEGF_{165}R$/NP-1 cDNA (PAE/NP-1 cells) in 48 well dishes. Non-specific binding was determined by competition with a 200-fold excess of unlabeled $VEGF_{165}$. After binding, the cells were washed, lysed and the cell-associated radioactivity was determined using a γ counter.

FIG. 7B. The binding data shown in FIG. 7A were analyzed by the method of Scatchard, and a best fit plot was obtained with the LIGAND program (Munson and Rodbard, 1980). PAE/NP-1 cells express approximately $3\times10^5$ $VEGF_{165}$ binding sites per cell and bind $^{125}I\text{-}VEGF_{165}$ with a $K_d$ of $3.2\times10^{-10}$ M.

A single KDR receptor or a KDR-$VEGF_{165}R$/NP-1 pair is shown in top portion. An expanded view showing several receptors is shown in the bottom portion. $VEGF_{165}$ binds to KDR via exon 4 and to $VEGF_{165}R$/NP-1 via exon 7 (Keyt et al. *J. Biol. Chem.* 271, 5638-5646 (1996b); Soker et al., *J. Biol. Chem.* 271, 5761-5767 (1996)). A rectangular $VEGF_{165}$ molecule represents a suboptimal conformation that doesn't bind to KDR efficiently while a rounded $VEGF_{165}$ molecule represents one that fits better into a binding site. In cells expressing KDR alone, $VEGF_{165}$ binds to KDR in a sub-optimal manner. In cells co-expressing KDR and $VEGF_{165}R$/NP-1, the binding efficiency of $VEGF_{165}$ to KDR is enhanced. It may be that the presence of $VEGF_{165}R$/NP-1increases the concentration of $VEGF_{165}$ on the cell surface, thereby presenting more growth factor to KDR. Alternatively, $VEGF_{165}R$/NP-1 may induce a change in $VEGF_{165}$ conformation that allows a better binding to KDR, or both might occur. In the presence of GST-$Ex^-$-8. $VEGF_{165}$ binding to $VEGF_{165}R$/NP-1 is competitively inhibited and its binding to KDR reverts to a sub-optimal manner.

FIG. 12 shows the human NP-2 amino acid sequence (SEQ ID NO:4).

FIGS. 13A to 13C show the human NP-2 DNA sequence (SEQ ID NO:3).

FIGS. 14A to 14F show the nucleotide (SEQ ID NO:1) and amino acid sequences (SEQ ID NO:2) of $VEGF_{165}R$/NP-1.

Figure 15A:
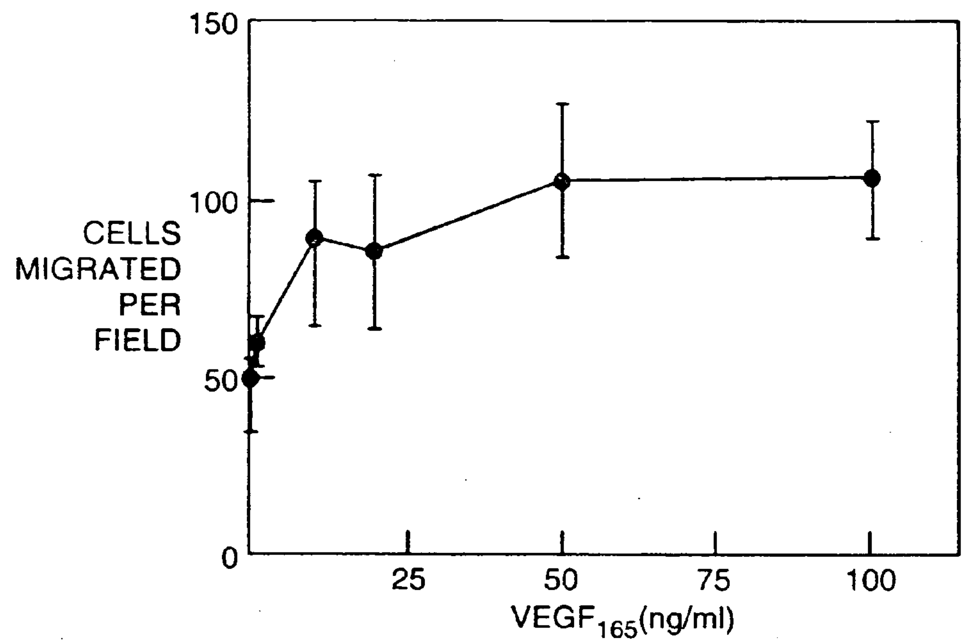
Figure 15B:
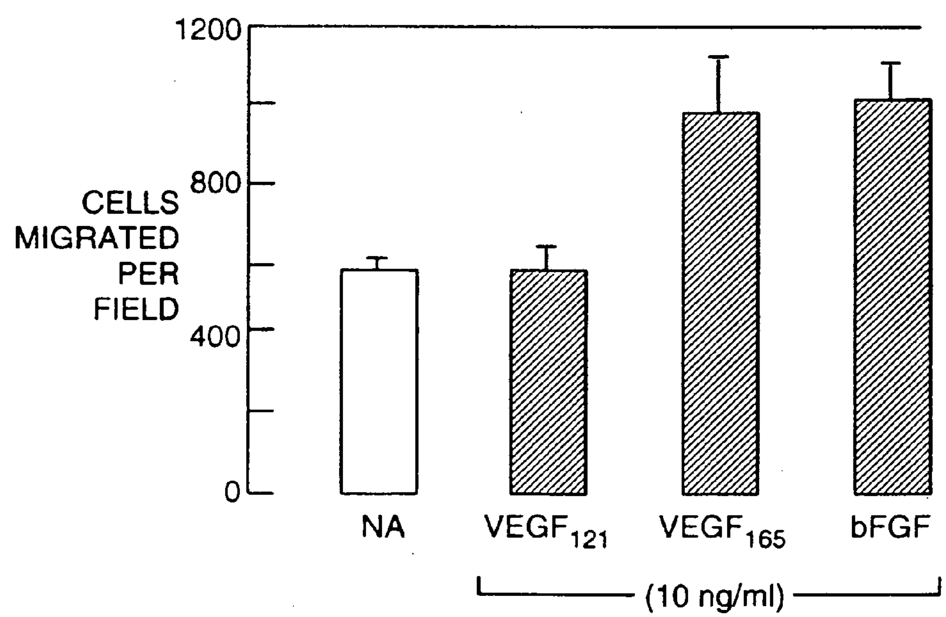

FIGS. 15A and 15B show $VEGF_{165}$ stimulation of MDA MB 231 cell motility. (FIG. 15A) Dose response of $VEGF_{165}$ motility activity. (FIG. 15B) Both $VEGF_{165}$ and bFGF stimulate motility but $VEGF_{125}$ does not.

Figure 16A:
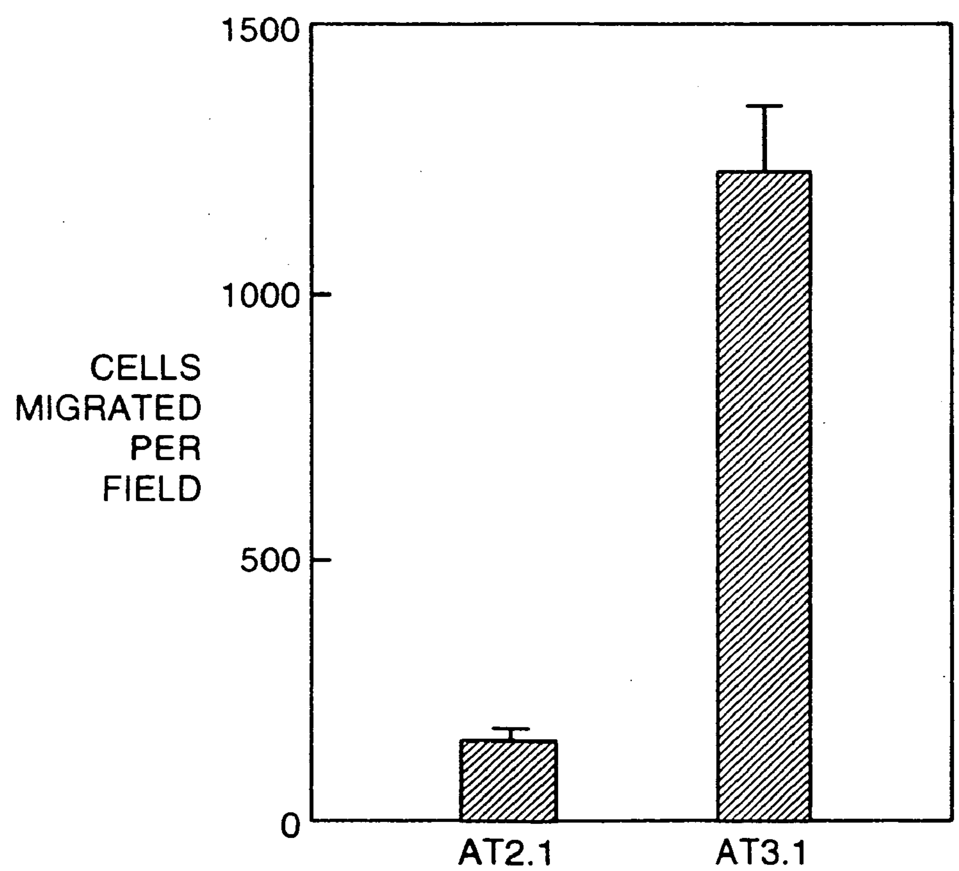
Figures 16B, 16C:
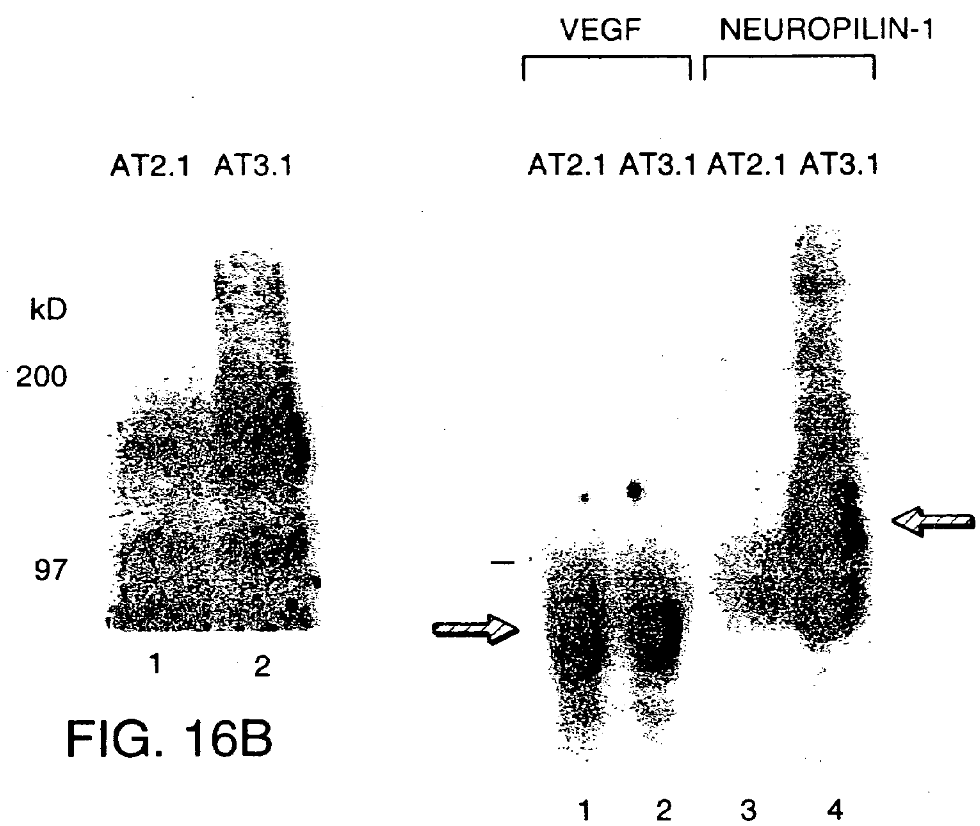

FIGS. 16A, 16B and 16C show motility and neuropilin-1 expression of Dunning rat prostate carcinoma cell lines AT3-1 (high motility, high metastatic potential) and AT2.1 (low motility, low metastatic potential) cells. (FIG. 16A) AT3.1 cells are more motile than AT2.1 cells in a Boyden chamber assay. 125I-$VEGF_{165}$ cross-links neuropilin-1 on AT-3.1 cells but does not cross-link to AT2.1 cells. (FIG. 16C) AT3.1 but not AT2.1 cells express neuropilin-1, while both cell types express VEGF.

Figures 17A, 17B, 17C:
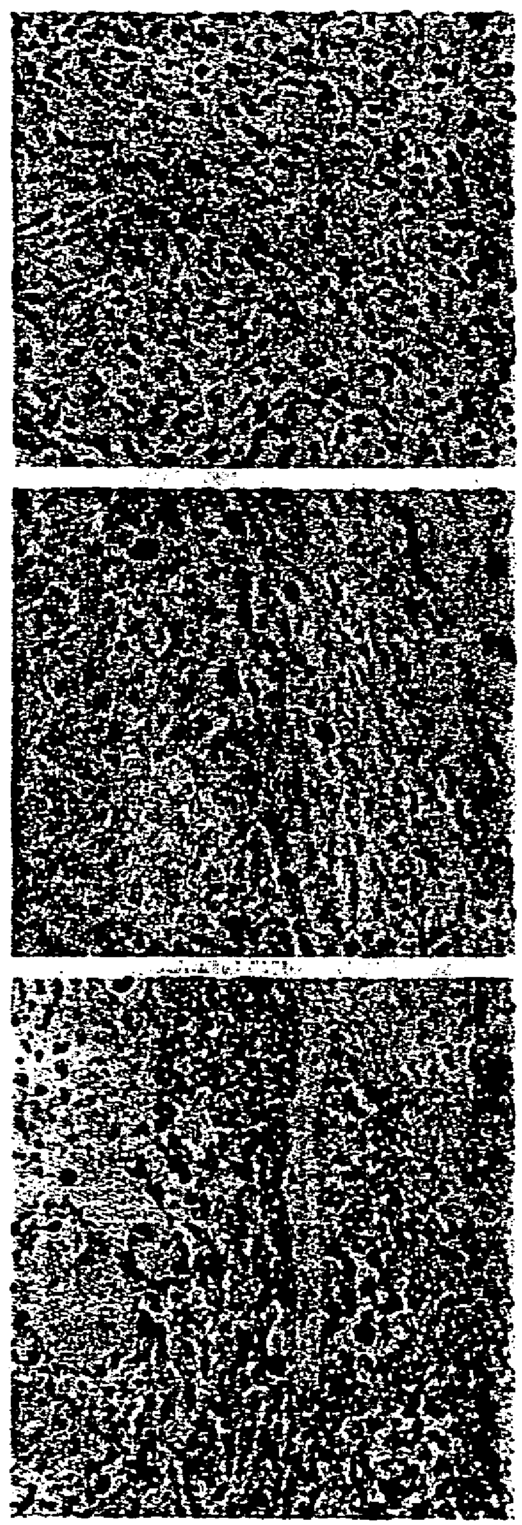

FIGS. 17A, 17B and 17C show immunostaining of (FIG. 17A) a PC3 subcutaneous tumor in a nude mouse. (FIG. 17B) an AT-3.1 tumor in a rat. (FIG. 17C) an AT2.1 tumor in rat with anti-neuropilin-1 antibodies. Neuropilin immunostaining is preferentially associated with PC3 and AT3.1 tumor cells at the tumor dermis boundary. Some of these cells cluster around blood vessels. AT2.1 cells do not express neuropilin-1.

Figure 18A:
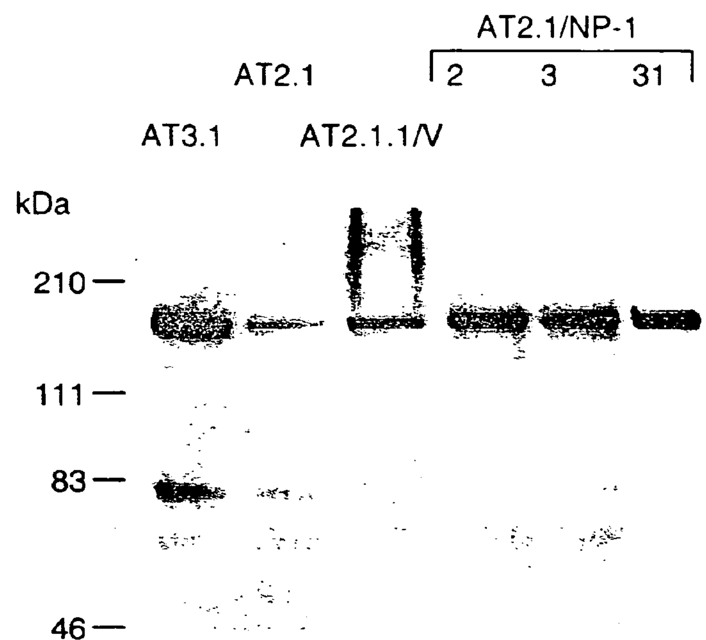
Figure 18B:
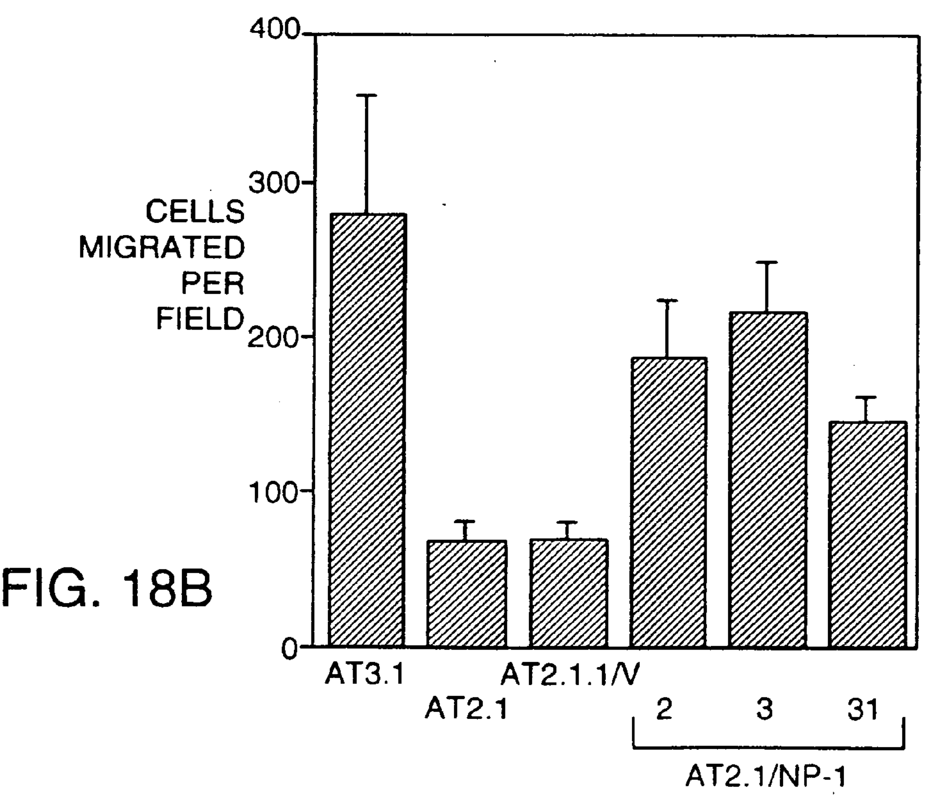

FIGS. 18A and 18B show overexpression of neuropilin-1 in AT2.1 cells. (FIG. 18A) Western blot. (FIG. 18B) motility activity. Three AT2.1 clones (lanes 4,5,6) express higher amounts of neuropilin-1 protein and are more motile compared to parental AT2.1 cells or AT2.1 vector (AT2.1 V) controls and approach AT3.1 cell neuropilin-1 levels and migration activity.

Figure 19:
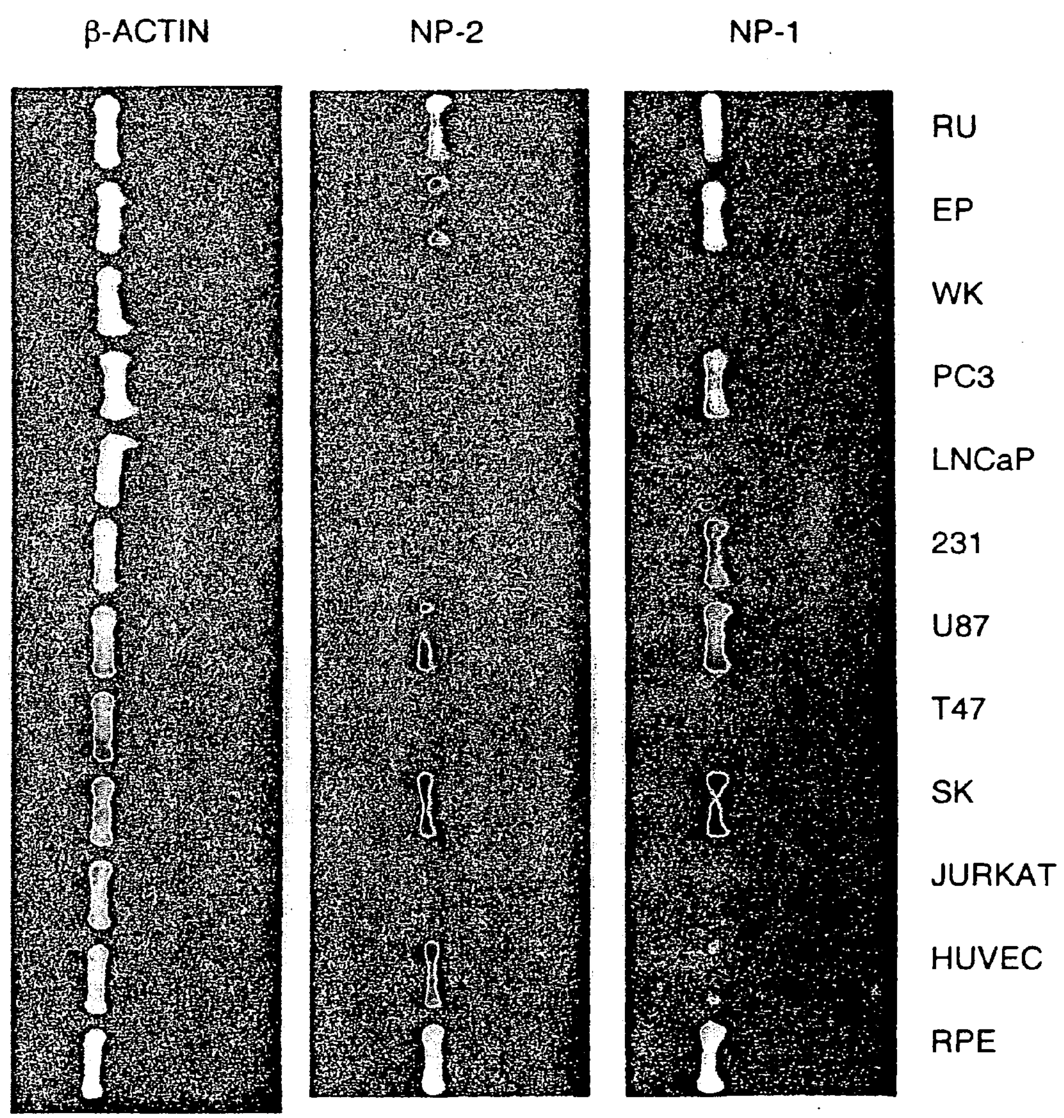

FIG. 19 shows expression of NP-1, NP-2 and β-actin in cancer cell lines and endothelial cells using reverse transcriptase PCR following primers:

Human NP-1
Forward (328-351): 5'TTTCGCAACGATAAATGTGGC-GAT 3' (SEQ ID NO:7)
Reverse (738-719): 5'TATCACTCCACTAGGTGTTG 3' (SEQ ID NO:8)

Human NP-2
Forward (513-532): 5'CCAACCAGAAGATTGTCCTC 3' (SEQ ID NO:9)

Reverse (1181-1162): 5'GTAGGTAGATGAGGCACTGA 3'. (SEQ ID NO:10)

Figure 20:
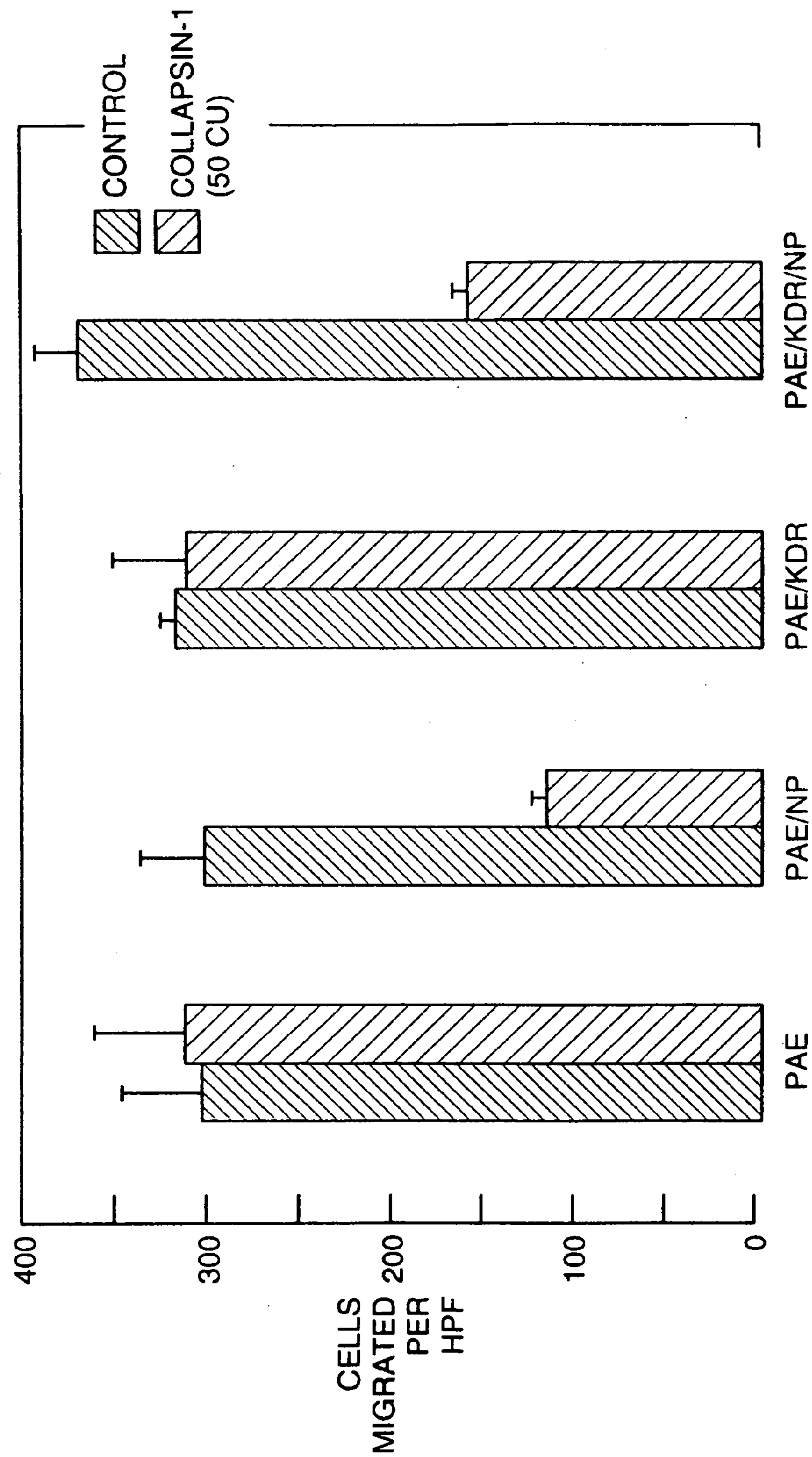

FIG. 20 shows the effects of collapsin-I treatment on PAE cell motility in a Boyden chamber. Collpasin-1 inhibits, by about 65% the basal migration of PAE cells expressing neuropilin-1 but not PAE cell expressing KDR. alone One collapsin unit is about 3 ng/ml.

Figures 21A, 21B:
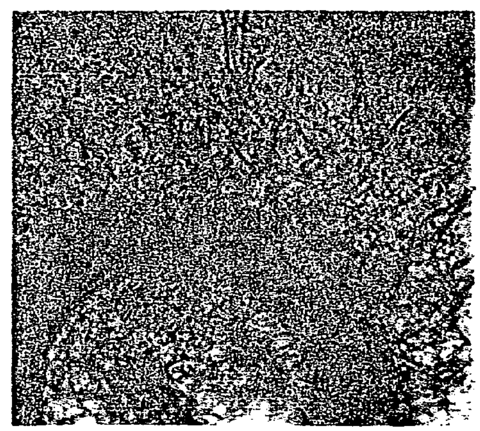

FIGS. 21A and 21B show results of the aortic ring assay. Collapsin was added (FIG. 21A) or not added (FIG. 21B) to a segment of rat aortic ring and the migration of endothelial cells out of the rings and their formation of tubes was monitored after a week in organ culture. Migration and tube formation are inhibited by collapsin-1.

DETAILED DESCRIPTION OF THE INVENTION

We have discovered that there are VEGF receptors (VEGFR) and neuropilins such as $VEGF_{165}R$/NP-1 and NP-2 that are associated with metastatic potential of a malignant cell and angiogenesis. As used herein, "neuropilin" includes not only $VEGF_{165}R$/NP-1 and NP-2 but any neuropilin or VEGFR, where the constituents share at least about 85% homology with either of the above $VEGF_{165}R$/NP-1 and NP-2 can be used. More preferably, such constituent shares at least 90% homology. Still more preferably, each constituent shares at least 95% homology.

Homology is measured by means well known in the art. For example % homology can be determined by any standard algorithm used to compare homologies. These include, but are not limited to BLAST 2.0 such as BLAST 2.0.4. and i.2.0.5. available from the NIH (See the World Wide Web at ncbi.nlm.nkh.gov_BLAST_newblast.html) (Altschul, S. F., et al. Nucleic Acids Res.25:3389-3402 (1997)) and DNASIS (Hitachi Software Engineering America. Ltd.) These programs should preferably be set to an automatic setting such as the standard default setting for homology comparisons. As explained by the NIH, the scoring of gapped results tends to be more biologically meaningful than ungapped results.

For ease of reference, this disclosure will generally talk about $VEGF_{165}R$/NP-1 and NP-2 and/or homologs thereof but all teaching are applicable to the above-described homologs.

In another embodiment a VEGFR can be used as long as it binds to a sequence having at least 90% more preferably 95% homology to exon 7 of $VEGF_{165}$. These VEGF receptors and neuropilins, e.g., $VEGF_{165}R$/NP-1 and NP-2, are associated with both tumor metastases and angiogenesis. We have shown that expression of $VEGF_{165}R$/NP-1 and NP-2 is upregulated in highly metastatic prostate cancer cell lines relative to poorly metastatic or nonmetastatic lines. Thus, expression of $VEGF_{165}R$/NP-1 and NP-2 is associated with a rumors metastatic potential.

In accordance with the present invention, antagonists of neuropilin receptor function can be used inhibit or prevent the metastasis process and or angiogenesis. Antagonists of the invention can block the receptors preventing ligand binding, disrupt receptor function, or inhibit receptor occurrence. Specific antagonists include, for example, compounds that bind to NP-1 or NP-2 and antibodies that specifically binds the receptor at a region that inhibits receptor function. For example, one can add an effective amount of a compound that binds to NP-1 to disrupt receptor function and thus inhibit metastasis.

Preferred antagonists include members of the semaphorin collapsins family. We have surprisingly discovered that members of the semaphorin collapsins family are not only inhibitors of neuronal guidance but also inhibitors of endothelial and tumor cell motility in cells that express neuropilin. Collapsin-1 is a particularly preferred antagonist. Other members of the semaphorin collapsin family can be selected by screening for neuropilin binding.

Semaphorin/collapsins are a family of 100 kDa glycoproteins (Luo, et al. (1993) *Cell* 75: 217-2271 Kolodkin, et al., (1993) *Cell* 75: 1389-1399. Behar, et al., (1996) *Nature* 383: 525-528.) Semaphorins are the mammalian homologue and collapsins are the chick homologue. Semaphorins are expressed primarily in the developing CNS, but are also found in developing bones and heart. The receptors for the semaphorins are neuropilin-1 and neuropilin-2 (He, et al., *Cell* 90, 739-751 (1997), Kolodkin, et al, *Cell* 90, 753-762 (1997)) and there is ligand binding specificity for different semaphorin family members (Chen, et al., *Neuron* 19:547-559 (1997)). The $K_d$ for semaphorin binding is about $3\times10^{-10}$M, similar to that for $VEGF_{165}$ binding to neuropilin-1. Semaphorins mediate neuronal guidance by repelling and collapsing advancing dorsal root ganglion (DRG) growth cones.

Semaphorin/collapsins are know in the art and can be isolated from natural sources or produced using recombinant DNA methods. See, for example, U.S. Pat. No. 5,807,826. Additionally, fragments of the semaphorin/collapsins may be used. For example, a 70 amino acid region within the semaphorin domain specifies the biological activities of three collapsin family members (Koppel, et al., *Neuron* 19: 531-537).

Pure recombinant chick collapsin-1 (semaphorin III) was can be produced by the methods set forth in the following references (Luo, et al. (1993) *Cell* 75: 217-227.); Koppel, et al. *J. Biol. Chem.* 273: 15708-15713. Feiner, et al. (1997) *Neuron* 19: 539-545).

We have shown that when collapsin-1 was added to cultures of porcine endothelial cells (PAE) and PAE neuropilin-1 and or KDR transfectants. $^{125}$I-Collapsin was found to bind to PAE cells expressing neuropilin-1 but not to PAE cells expressing KDR. Furthermore, in a Boyden chamber assay, collapsin-1 inhibited the basal migration of PAE expressing neuropilin-1, by about 60-70%, but had no effect on parental PAE or PAE expressing KDR alone (FIG. 20). Inhibition was dose-dependent and half-maximal inhibition occurred with 50 collapsing units ml (as measured on DRG. 1 CU=3 ng ml). Thus, semaphorin collapsins inhibit the motility of non-neuronal cells as long as neuropilin-1 is expressed.

Antibodies that specifically binds the NP at a region that inhibits receptor function can also be used as antagonists of the invention. Antibodies may be raised against either a peptide of the receptor or the whole molecule. Such a peptide may be presented together with a carrier protein, such as an KLH, to an animal system or, if it is long enough, say 25 amino acid residues, without a carrier.

In accordance with yet another aspect of the present invention, there are provided isolated antibodies or antibody fragments which selectively binds the receptor. The antibody fragments include, for example, Fab, Fab', F(ab')2 or Fv fragments. The antibody may be a single chain antibody, a humanized antibody or a chimeric antibody.

Antibodies, or their equivalents, or other receptor antagonists may also be used in accordance with the present invention for the treatment or prophylaxis of cancers. Administration of a suitable dose of the antibody or the antagonist may serve to block the receptor and this may provide a crucial time window in which to treat the malignant growth.

Prophylaxis may be appropriate even at very early stages of the disease, as it is not known what specific event actually triggers metastasis in any given case. Thus, administration of the antagonists which interfere with receptor activity, may be effected as soon as cancer is diagnosed, and treatment continued for as long as is necessary, preferably until the threat of the disease has been removed. Such treatment may also be used prophylactically in individuals at high risk for development of certain cancers, e.g., prostate or breast.

It will be appreciated that antibodies for use in accordance with the present invention may be monoclonal or polyclonal as appropriate. Antibody equivalents of these may comprise: the Fab' fragments of the antibodies, such as Fab, Fab', F(ab')2 and Fv; idiotopes; or the results of allotope grafting (where the recognition region of an animal antibody is grafted into the appropriate region of a human antibody to avoid an immune response in the patient), for example. Single chain antibodies may also be used. Other suitable modifications and/or agents will be apparent to those skilled in the art.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81.6851 (1985); Takeda, et al., Nature 314,452(1985). Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britian.

The present invention further provides use of neuropilin for intracellular or extracellular targets to affect binding. Intracellular targeting can be accomplished through the use of intracellularly expressed antibodies referred to as intrabodies. Extracellular targeting can be accomplished through the use of receptor specific antibodies.

These methods can be used to inhibit metastasis in malignant cells as we have found that the presence of these receptors is positively correlated with metastasis. One can treat a range of afflictions or diseases associated with expression of the receptor by directly blocking the receptor. This can be accomplished by a range of different approaches. One preferred approach is the use of antibodies that specifically block VEGF binding to the receptor. For example, an antibody to the VEGF binding site. Antibodies to these receptors can be prepared by standard means. For example, one can use single chain antibodies to target these binding sites.

The antibody can be administered by a number of methods. One preferred method is set forth by Marasco and Haseltine in PCT WO94/02610, which is incorporated herein by reference. This method discloses the intracellular delivery of a gene encoding the antibody. One would preferably use a gene encoding a single chain antibody. The antibody would preferably contain a nuclear localization sequence. One preferably uses an SV40 nuclear localization signal. By this method one can intracellularly express an antibody, which can block $VEGF_{165}$R/NP-1 or NP-2 functioning in desired cells.

DNA encoding human $VEGF_{165}$R/NP-1 or NP-2 and recombinant human $VEGF_{165}$R/NP-1 or NP-1 may be produced according to the methods set forth in the Examples.

The receptors are preferably produced by recombinant methods. A wide variety of molecular and biochemical methods are available for generating and expressing the polypeptides of the present invention: see e.g. the procedures disclosed in *Molecular Cloning, A Laboratory Manual* (2nd Ed., Sambrook, Fritsch and Maniatis, Cold Spring Harbor), *Current Protocols in Molecular Biology* (Eds. Aufubel, Brent, Kingston, More, Feidman, Smith and Stuhl. Greene Publ. Assoc., Wiley-Interscience, NY, N.Y. 1992) or other procedures that are otherwise known in the art. For example, the polypeptides of the invention may be obtained by chemical synthesis, expression in bacteria such as *E. coli* and eukaryotes such as yeast, baculovirus, or mammalian cell-based expression systems, etc., depending on the size, nature and quantity of the polypeptide.

The term "isolated" means that the polypeptide is removed from its original environment (e.g., the native VEGF molecule). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and or such polynucleotides or polypeptides could be part of a composition, and still be isolated in that such vector or composition is not part of its natural environment.

Where it is desired to express the receptor or a fragment thereof, any suitable system can be used. The general nature of suitable vectors, expression vectors and constructions therefor will be apparent to those skilled in the art.

Suitable expression vectors may be based on phases or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (*Proc. Natl. Acad. Sci.* USA 74:5463-7 (1977)).

A DNA fragment encoding the receptor or fragment thereof, may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct trading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired polypeptide or protein may be expressed. The extent of expression may be analyzed by SDS polyacrylamide gel electrophoresis-SDS-PAGE (Lemelli, *Nature* 227:680-685 (1970)).

Suitable methods for growing and transforming cultures etc. are usefully illustrated in, for example, Maniatis (Molecular Cloning. A Laboratory Notebook, Maniatis et al. (eds.). Cold Spring Harbor Labs. N.Y. (1989)).

Cultures useful for production of polypeptides or proteins may suitably be cultures of any living cells, and may vary from prokaryotic expression systems up to eukaryotic expression systems. One preferred prokaryotic system is that of *E. coli*, owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line and the baculovirus system.

Other expression systems which may be employed include streptomycetes, for example, and yeasts, such as *Saccharomyces* spp., especially *S. cerevisiae*. Any system may be used as desired, generally depending on what is required by the operator. Suitable systems may also be used to amplify the genetic material, but it is generally convenient to use *E. coli* for this purpose when only proliferation of the DNA is required.

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis and the like. One of skill in the art may select the most appropriate isolation and purification techniques without departing from the scope of this invention.

The present invention also provides binding assays using $VEGF_{165}R$/NP-1 or NP-2 that permit the ready screening for compounds which affect the binding of the receptor and its ligands, e.g., VEGF165. These assays can be used to identify compounds that modulate, preferably inhibit metastasis and or angiogenesis. However, it is also important to know if a compound enhances metastasis so that its use can be avoided. For example, in a direct binding assay the compound of interest can be added before or after the addition of the labeled ligand, e.g.. $VEGF_{165}$ and the effect of the compound on binding or cell motility or angiogenesis can be determined by comparing the degree of binding in that situation against a base line standard with that ligand, not in the presence of the compound. The assay can be adapted depending upon precisely what is being tested.

The preferred technique for identifying molecules which bind to the neuropilin receptor utilizes a receptor attached to a solid phase, such as the well of an assay plate. The binding of the candidate molecules, which are optionally labeled (e.g., radiolabeled), to the immobilized receptor can be measured. Alternatively, competition for binding of a known, labeled receptor ligand, such as $I\text{-}^{125}$ $VEGF_{165}$, can be measured. For screening for antagonists, the receptor can be exposed to a receptor ligand, e.g., $VEGF_{165}$ followed by the putative antagonist, or the ligand and antagonist can be added to the receptor simultaneously and the ability of the antagonist to block receptor activation can be evaluated. For example, VEGF antagonist activity may also be determined by inhibition of binding of labeled $VEGF_{165}$ to $VEGF_{165}R$ as disclosed in the Examples.

The ability of discovered antagonists to influence angiogenesis or metastasis can also be determined using a number of know in vivo and in vitro assays. Such assays are disclosed in Jain et al., *Nature Medicine* 3, 1203-1208 (1997), and the examples.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are one preferred mode of administration.

Neuropilin expression may also be inhibited in vivo by the use of antisense technology. Antisense technology can be used to control gene expression through triple-helix formation or antisense DNA or RNA, both of which methods are based on binding of a polynucleotide to DNA or RNA. An antisense nucleic acid molecule which is complementary to a nucleic acid molecule encoding receptor can be designed based upon the isolated nucleic acid molecules encoding the receptor provided by the invention. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO:1 ($VEGF_{165}R$/NP-1) or SEQ ID NO:3 (NP-2). A nucleic acid is designed which has a sequence complementary to a sequence of the coding or untranslated region of the shown nucleic acid. Alternatively, an antisense nucleic acid can be designed based upon sequences of a $VEGF_{165}R$ gene, which can be identified by screening a genomic DNA library with an isolated nucleic acid of the insertion. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1)1986.

The term "pharmaceutically acceptable" refers to compounds and compositions which may be administered to mammals without undue toxicity. Exemplary pharmaceutically acceptable salts include mineral acid salts such as hydrochlorides, hydrobromides. phosphates, sulfates, and the like; and the salts of organic acids such as acetates, propionates, malonates, benzoates, and the like.

The antagonists of the invention are administered orally, topically, or by parenteral means, including subcutaneous and intramuscular injection, implantation of sustained release depots, intravenous injection, intranasal administration, and the like. Accordingly, antagonists of the invention may be administered as a pharmaceutical composition comprising the antibody or nucleic acid of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen. Carbopol Registered™, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin. Silvadene Registered™ (Marion). Aquaphor Registered™ (Duke Laboratories), and the like. Other topical formulations include aerosols, bandages, and other wound dressings. Alternatively one may incorporate or encapsulate the compounds such as an antagonist in a suitable polymer matrix or membrane, thus providing a sustained-release delivery device suitable for implantation near the site to be treated locally. Other devices include indwelling catheters and devices such as the Alzet Registered™ minipump. Ophthalmic preparations may be formulated using commercially available vehicles such as Sorbi-care Registered™ (Allergan). Neodecadron Registered™ (Merck, Sharp & Dohme). Lacrilube Registered™, and the like, or may employ topical preparations such as that described in U.S. Pat. No. 5,124,155, incorporated herein by reference. Further, one may provide an antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The NP antagonists of the invention can be combined with a therapeutically effective amount of another molecule which negatively regulates angiogenesis which may be, but is not limited to, TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alfa, soluble KDR and FLT-1 receptors and placental proliferin-related protein.

An NP antagonist of the invention may also be combined with chemotherapeutic agents.

The DNA encoding an antagonist, e.g., a collapsin, can be used in the form of gene therapy and delivered to a host by any method known to those of skill in the art to treat disorders associated with VEGF.

The amount of an NP antagonist required to treat any particular disorder will of course vary depending upon the nature and severity of the disorder, the age and condition of the subject, and other factors readily determined by one of ordinary skill in the art.

All references cited above or below are herein incorporated by reference.

The present invention is further illustrated by the following Examples. These Examples are provided to aid in the understanding of the invention and are not construed as a limitation thereof.

EXAMPLE 1

Experimental Procedures

Materials

Cell culture media, lipofectin and lipofectamin reagents for transfection were purchased from Life Technologies. Human recombinant $VEGF_{165}$ and $VEGF_{121}$ were produced in Sf-21 insect cells infected with recombinant baculovirus vectors encoding either human $VEGF_{165}$ or $VEGF_{121}$ as previously described (Cohen et al., *Growth Factors,* 7, 131-138 (1992); Cohen et al., *J. Biol. Chem.,* 270, 11322-11326 (1995)). GST VEGF exons 7+8 fusion protein was prepared in *E. coli* and purified as previously described (Soker et al., *J. Biol. Chem.,* 271, 5761-5767 (1996)). Heparin, hygromycin B and protease inhibitors were purchased from Sigma (St. Louis, Mo.) $^{125}$I-Sodium, $^{32}$P-dCTP, and GeneScreen-Plus hybridization transfer membrane were purchased from DuPont NEN (Boston, Mass.). Disuccinimidyl suberate (DSS) and IODO-BEADS were purchased from Pierce Chemical Co. (Rockford, Ill.). Con A Sepharose was purchased from Pharmacia LKB Biotechnology Inc. (Piscataway, N.J.). RNAzol-B was purchased from TEL-TEST Inc. (Friendswood, Tex.). Silver Stain kit and Trans-Blot PVDF membranes were purchased from Bio-Rad Laboratories (Hercules, Calif.). Multiple tissue northern blot membranes were purchased from Clontech (Palo Alto, Calif.). PolyATract mRNA isolation kits were purchased from Promega (Madison, Wis.). RediPrime DNA labeling kits and molecular weight markers were purchased from Amersham (Arlington Heights, Ill.). Plasmids: pcDNA3.1 was purchased from Invitrogen (Carlsbad, Calif.), and pCPhygro, containing the CMV promoter and encoding hygromycin B phosphorylase, was kindly provided by Dr. Urban Deutsch (Max Plank Institute, Bad Nauheim, Germany). Restriction endonucleases and Ligase were purchased from New England Biolabs, Inc (Beverly, Mass.). NT-B2 photographic emulsion and x-ray film were purchased from the Eastman Kodak company (Rochester, N.Y.).

Cell Culture

Human umbilical vein EC (HUVEC) were obtained from American Type Culture Collection (ATCC) (Rockville, Md.), and grown on gelatin coated dishes in M-199 medium containing 20% fetal calf serum (FCS) and a mixture of glutamine, penicillin and streptomycin (GPS). Basic FGF (2 ng ml) was added to the culture medium every other day. Parental porcine aortic endothelial (PAE) cells and PAE cells expression KDR (PAE/KDR) (Waltenberger et al., *J. Biol. Chem.* 269, 26988-26995 (1994)) were kindly provided by Dr. Lena Claesson-Welsh and were grown in F12 medium containing 10% FCS and GPS. MDA-MB-231 cells and MDA-MB-453 cells were obtained from ATCC, and grown in DMEM containing 10% FCS and GPS. The human melanoma cell lines, RU-mel, EP-mel and WK-mel were kindly provided by Dr. Randolf Byer (Boston University Medical School, Boston, Mass.), and grown in DMEM containing 2% FCS, 8% calf serum and GPS. Human metastatic prostate adenocarcinoma. LNCaP and prostate carcinoma. PC3 cells were kindly provided by Dr. Michael Freeman (Children's Hospital, Boston, Mass.), and grown in RPMI 1640 containing 5% FCS and GPS.

Purification and Protein Sequencing

Approximately $5\times10^8$ MDA-MB-231 cells grown in 150 cm dishes were washed with PBS containing 5 mM EDTA, scraped and centrifuged for 5 min at 500 g. The cell pellet was lysed with 150 ml of 20 mM HEPES, pH 8.0, 0.5% triton X-100 and protease inhibitors including 1 mM AEBSF, 5 μg ml leupeptin and 5 μg/ml aprotinin for 30 min on ice, and the lysate was centrifuged at 30,000×g for 30 min. $MnCl_2$ and $CaCl_2$ were added to the supernatant to obtain a final concentration of 1 mM each. The lysate was absorbed onto a Con A Sepharose column (7 ml) and bound proteins were eluted with 15 ml 20 mM HEPES, pH 8.0, 0.2 M NaCl, 0.1% triton X-100 and 1 M methyl-α-D-mannopyranoside at 0.2 ml min. The elution was repeated twice more at 30 minute intervals. The Con A column eluates were pooled and incubated for 12 h at 4° C. with 0.5 ml of $VEGF_{165}$-Sepharose beads, containing about 150 μg $VEGF_{165}$, prepared as described previously (Wilchek and Miron, *Biochem. Int.* 4, 629-635. (1982)). The $VEGF_{165}$-Sepharose beads were washed with 50 ml of 20 mM HEPES, pH 8.0, 0.2 M NaCl and 0.1% triton X-100 and then with 25 ml of 20 mM HEPES. pH 8.0. The beads were boiled in SDS-PAGE buffer and bound proteins were separated 6% SDS-PAGE. Proteins were transferred to a TransBlot PVDF membrane using a semi-dry electric blotter (Hoeffer Scientific), and the PVDF membrane was stained with 0.1% Coomassie Brilliant Blue in 40% methanol. The two prominent proteins in a 130-140 kDa doublet were cut out separately and N-terminally sequenced using an Applied Biosystems model 477A microsequenator as a service provided by Dr. William Lane of the Harvard Microchemistry facility (Cambridge, Mass.).

Expression Cloning and DNA Sequencing

Complementary DNA (cDNA) was synthesized from 5 μg 231 mRNA. Double-stranded cDNA was ligated to EcoRI adaptors, and size-fractionated on a 5-20% potassium acetate gradient. DNA fragments larger than 2 kb were ligated to an eukaryotic expression plasmid, pcDNA3.1. The plasmid library was transfected into *E. coli* to yield a primary library or approximately $1\times10^2$ individual clones. A portion of the transformed bacteria was divided into 240 pools, each representing approximately $3\times10^3$ individual clones. DNA prepared from each pool was used to transfect COS-7 cells seeded in 12 well dishes, using the Lipofectin reagent according to the manufacturer's instructions. Three days after transfection, the cells were incubated on ice for 2 h with $^{125}I$-$VEGF_{165}$ (10 ng/ml) in the presence of 1 μg ml heparin, washed and fixed with 4% paraformaldehyde in PBS. $^{125}I$-$VEGF_{165}$ binding to individual cells was detected by overlaying the monolayers with photographic emulsion, NT-B2, and developing the emulsion after two days as described (Gearing et al., 1989). Seven positive DNA pools were identified and DNA from one of the positive pools was used to transform *E. coli*. The *E. coli* were sub-divided into 50 separate pools and plated onto 50 LB ampicillin dishes, with each pool representing approximately 100 clones. DNA made from these pools was transfected into COS-7 cells which were screened for $^{125}I$-$VEGF_{165}$ binding as described above. Twenty positive pools were detected at this step, and their corresponding DNAs were used to transform *E. coli*. Each pool was plated onto separate LB ampicillin dishes and DNA was prepared from 96 individual colonies and screened in a 96-well two dimensional grid for $^{125}I$-$VEGF_{165}$ binding to transfected COS-7 cells as described above. Seven single clones were identified as being positive at this step. The seven positive plasmid clones where amplified and their DNA was analyzed by restriction enzyme digestion. Six clones showed an identical digestion pattern of digest and one was different. One clone from each group was submitted for automated DNA sequencing.

Northern Analysis

Total RNA was prepared from cells in culture using RNAzol according to the manufacturer's instructions. Samples of 20 μg RNA were separated on a 1% formaldehyde-agarose gel, and transferred to a GeneScreen-Plus membrane. The membrane was hybridized with a $^{32}P$ labeled fragment of human $VEGF_{165}R$/NP-1 cDNA, corresponding to nucleotides 63-454 in the ORF, at 63° C. for 18 h. The membrane was washed and exposed to an x-ray film for 18 h. A commercially-obtained multiple human adult tissue mRNA blot (Clonetech, 2 μg/lane) was probed for human NP-1 in a similar manner. The multiple tissue blot was stripped by boiling in the presence of 0.5% SDS and re-probed with a $^{32}P$ labeled fragment of KDR cDNA corresponding to nucleotides 2841-3251 of the ORF (Terman et al., *Oncogene* 6, 1677-1683 (1991)).

Transfection of PAE Cells

Parental PAE cells and PAE cells expressing KDR (PAE/KDR) (Waltenberger et al., 1994) were obtained from Dr. Lena Claesson-Welsh. Human NP-1 cDNA was digested with XhoI and XbaI restriction enzymes and subcloned into the corresponding sites of pCPhygro, to yield pCPhyg-NP-1. PAE and PAE/KDR cells were grown in 6 cm dishes and transfected with 5 μg of pCPhyg-NP-1 using Lipofectamine, according to the manufacturer's instructions. Cells were allowed to grow for an additional 48 h and the medium was replaced with fresh medium containing 200 μg/ml hygromycin B. After 2 weeks, isolated colonies ($5$-$10\times10^3$ cell/colony) were transferred to separate wells of a 48 well dish and grown in the presence of 200 μg/ml hygromycin B. Stable PAE cell clones expressing $VEGF_{165}R$/NP-1 (PAE/NP-1) or co-expressing $VEGF_{165}R$/NP-1 and KDR (PAE/KDR/NP-1) were screened for $VEGF_{165}$ receptor expression by binding and cross linking of $^{125}I$-$VEGF_{165}$. For transient transfection. PAE/KDR cells were transfected with $VEGF_{165}R$/NP-1 as described above and after three days $^{125}I$-$VEGF_{165}$ cross-linking analysis was carried out.

Radio-iodination of VEGF, Binding and Cross-linking Experiments.

The radio-iodination of $VEGF_{165}$ and $VEGF_{121}$ using IODO-BEADS was carried out as previously described (Soker et al, *J. Biol. Chem.* 272, 31582-31588 (1997)). The specific activity ranged from 40,000-100,000 cpm/ng protein. Binding and cross-linking experiments using $^{125}I-VEGF_{165}$ and $^{125}I-VEGF_{121}$ were performed as previously described (Gitay-Goren et al., *J. Biol. Chem.* 267, 6093-6098 (1992); Soker et al., *J. Biol. Chem.* 271, 5761-5767 (1996)). VEGF binding was quantitated by measuring the cell-associated radioactivity in a γ-counter (Beckman, Gamma 5500). The counts represent the average of three wells. All experiments were repeated at least three times and similar results where obtained. The results of the binding experiments were analyzed by the method of Scatchard using the LIGAND program (Munson and Rodbard, 1980). $^{125}I-VEGF_{165}$ and $^{125}I-VEGF_{121}$ cross linked complexes were resolved by 6% SDS/PAGE and the gels where exposed to an X-Ray film. X-ray films were subsequently scanned by using an IS-1000 digital imaging system (Alpha Innotech Corporation)

Purification of $VEGF_{165}R$

Figure 1:
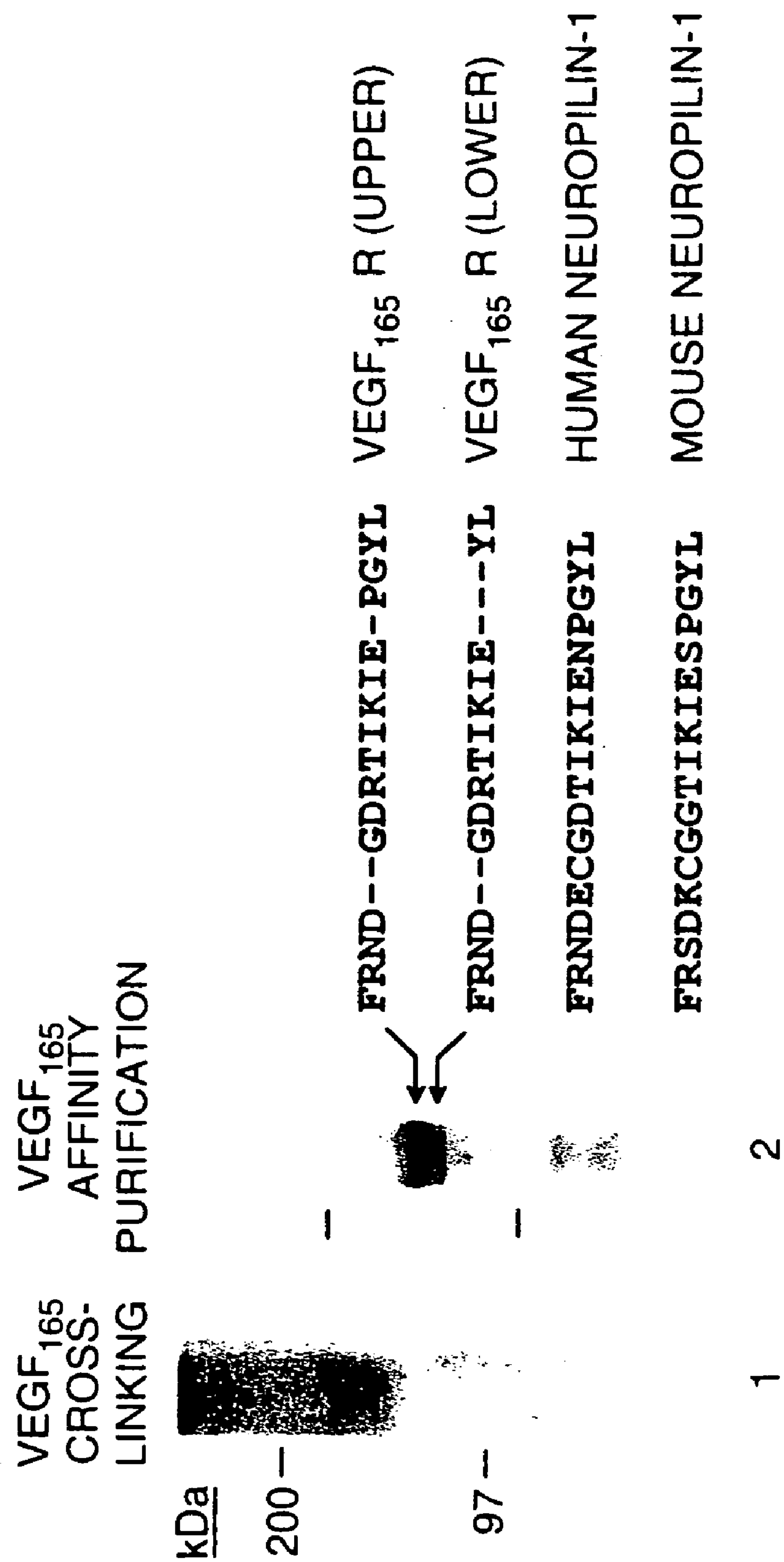
FIG. 1 shows purification of $VEGF_{165}R$ From 231 Cells. $^{125}I-VEGF_{165}$ (5 ng/ml) was bound and cross-linked to receptors on 231 cells and analyzed by SDS PAGE and autoradiography (lane 1). $VEGF_{165}R$ was purified by Con A and $VEGF_{165}$ affinity column chromatography and analyzed by SDS-PAGE and silver stain (lane 2). Two prominent bands were detected (arrows) and N-terminally sequenced separately. Their N-terminal 18 amino acid sequences are shown to the right of the arrows. The published N-terminal sequences of human and mouse neuropilin (Kawakami et al., *J. Neurobiol.,* 29, 1-17 (1995): He and Tessier-Lavigne, *Cell* 90, 739-751 1997) are shown below (SEQ ID NOS: 5 and 6).
Figure 9:
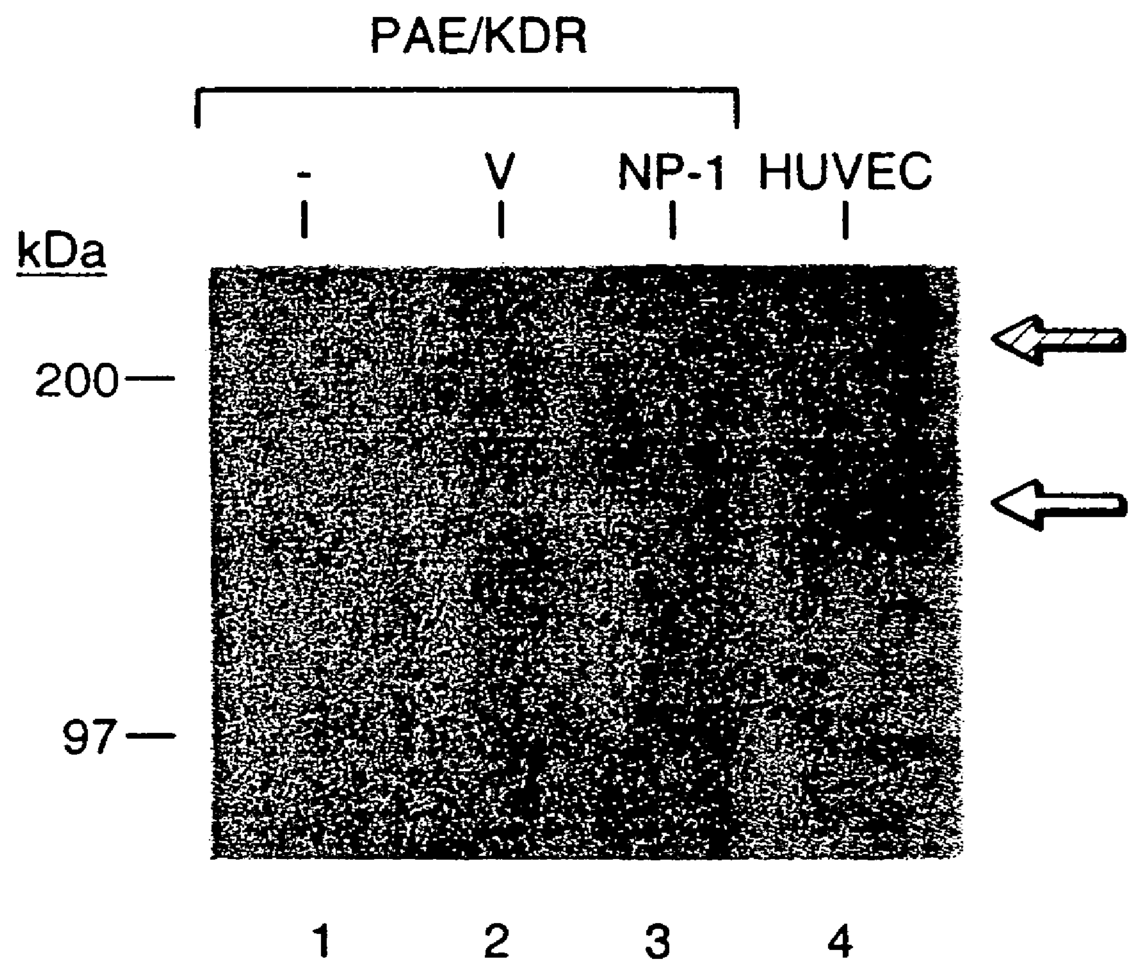
FIG. 9 shows cross linking of $VEGF_{165}$ to PAE KDR Cells Co-expressing $VEGF_{165}R$-NP-1 Transiently. PAE/KDR cells were transfected with pCPhygro or pCPhyg-NP-1 plasmids as described in "Experimental Procedures", and grown for 3 days in 6 cm dishes. $^{125}I\text{-}VEGF_{165}$ (5 ng ml) was bound and cross linked to parental PAE/KDR cells (lane 1), to PAE/KDR cells transfected with pCPhygro vector control (V) (lane 2), to PAE.KDR cells transfected with pCPhyg-$VEGF_{165}R$/NP-1 plasmids ($VEGF_{165}R$/NP-1) (lane 3), and to HUVEC (lane 4).). The binding was carried out in the presence of 1 μg ml heparin. The cells were lysed and proteins were resolved by 6% SDS-PAGE as in FIG. 8. Solid arrows denote radiolabeled complexes containing $^{125}I\text{-}VEGF_{165}$ and KDR. Open arrows denote radiolabeled complexes containing $^{125}I\text{-}VEGF_{165}$ and $VEGF_{165}R$/NP-1.

Cross-linking of $^{125}I-VEGF_{165}$ to cell surface receptors of 231 cells results in formation of a 165-175 kDa labeled complex (Soker et al., *J. Biol. Chem.* 271, 5761-5767 (1996)). These cells have about $1\text{-}2\times10^5$ $VEGF_{165}$ binding sites cell. In contrast to $VEGF_{165}$, $VEGF_{121}$ does not bind to the 231 cells and does not form a ligand-receptor complex (Soker et al., *J. Biol. Chem.* 271, 5761-5767 (1996)). The relatively high $VEGF_{165}R$ number and the lack of any detectable KDR or Flt-1 mRNA in 231 cells (not shown) suggested that these cells would be a useful source for $VEGF_{165}R$ purification. Preliminary characterization indicated that $VEGF_{165}R$ is a glycoprotein and accordingly, a 231 cell lysate prepared from approximately $5\times10^8$ cells was absorbed onto a Con A Sepharose column. Bound proteins, eluted from the Con A column, were incubated with $VEGF_{165}$-Sepharose and the $VEGF_{165}$-affinity purified proteins were analyzed by SDS-PAGE and silver staining (FIG. 9, lane 2). A prominent doublet with a molecular mass of about 130-135 kDa was detected. This size is consistent with the formation of a 165-175 kDa complex of 40-45 kDa $VEGF_{165}$ bound to receptors approximately 130-135 kDa in size (FIG. 9, lane 1). The two bands were excised separately and N-terminal amino acid sequencing was carried out (FIG. 1, right). Both the upper and lower bands had similar N-terminal amino acid sequences which showed high degrees of sequence homology to the predicted amino acid sequences in the N-terminal regions of mouse (Kawakami et al., *J. Neurobiol,* 29, 1-17 (1995)) and human neuroplilin-1 (NP-1) (He and Tessier-Lavigne, *Cell* 90739-751 (1997)).

Expression Cloning of $VEGF_{165}R$ From 231 Cell-derived mRNA

Figure 2A:
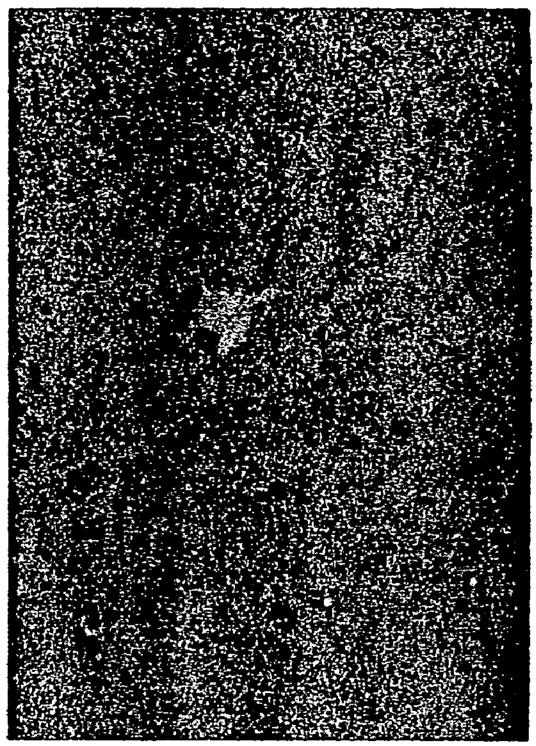
FIGS. 2A and 2B show isolation of $VEGF_{165}R$ cDNA by Expression Cloning. Photomicrographs (dark field illumination) of COS 7 cells binding $^{125}I-VEGF_{165}$. $^{125}I-VEGF_{165}$ was bound to transfected COS 7 cells which were then washed, fixed, and overlayed with photographic emulsion that was developed as described in the example, infra.
Figure 2B:
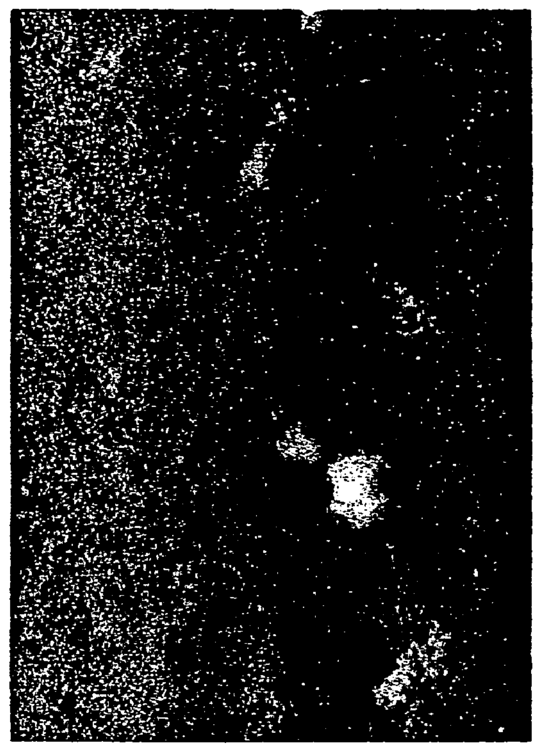

Concomitant with the purification, $VEGF_{165}R$ was cloned by expression cloning (Aruffo and Seed, *Proc. Natl. Acad. Sci.* USA 84, 8573-8577 (1987a); Aruffo and Seed, *EMBO J.,* 6, 3313-3316 (1987b); Gearing et al., *EMBO J.* 8, 3667-3676 (1989)). For expression cloning, 231 cell mRNA was used to prepare a cDNA library of approximately $10^7$ clones in a eukaryotic expression plasmid. *E. coli* transformed with the plasmid library were divided into pools. The DNA prepared from each pool were transfected into COS-7 cells in separate wells and individual cells were screened for the ability to bind $^{125}I-VEGF_{165}$ as detected by autoradiography of monolayers overlayed with photographic emulsion (FIG. 2A). After three rounds of subpooling and screening, seven single positive cDNA clones were obtained. FIG. 2B shows binding of $^{125}I-VEGF_{165}$ to COS-7 cells transfected with one of these single positive clones (clone A2).

Restriction enzyme analysis revealed that six of the seven positive single clones had identical restriction digestion patterns but that one clone had a pattern that was different (not shown). Sequencing of one of these similar cDNA clones, clone A2 (FIG. 3), showed it to be identical to a sequence derived from a human-expressed sequence tag data bank (dbEST). This sequence also showed a high percentage of homology to the sequence of mouse neuropilin. NP-1 (Kawakami et al., *J. Neurobiol.* 29, 1-17 (1995)). After we had cloned human $VEGF_{165}R$, two groups reported the cloning of rat and human receptors for semaphorin III and identified them to be NP-1 (He and Tessier-Lavigne, *Cell* 90, 739-751 (1997); Kolodkin et al., *Cell* 90, 753-762 (1997)). The 231 cell-derived $VEGF_{165}R$ cDNA sequence is virtually identical (see figure legend 3 for exceptions) to the human NP-1 sequence (He and Tessier-Lavigne, *Cell* 90, 739-751 (1997)). Significantly, the predicted amino acid sequence obtained by expression cloning (FIG. 3) confirmed the identification of $VEGF_{165}R$ as NP-1 that was determined by N-terminal sequencing (FIG. 1), and we have therefore named this VEGF receptor, $VEGF_{165}R$/NP-1.

The human $VEGF_{165}R$/NP-1 cDNA sequence predicts an open reading frame (ORF) of 923 amino acids with two hydrophobic regions representing putative signal peptide and transmembrane domains (FIG. 3). Overall, the sequence predicts ectodomain, transmembrane and cytoplasmic domains consistent with the structure of a cell surface receptor. The N-terminal sequence obtained via protein purification as shown in FIG. 1 is downstream of a 21 amino acid putative hydrophobic signal peptide domain, thereby indicating directly where the signal peptide domain is cleaved and removed. The short cytoplasmic tail of 40 amino acids is consistent with results demonstrating that soluble $VEGF_{165}R$/NP-1 released by partial trypsin digestion of 231 cells is similar in size to intact $VEGF_{165}R$/NP-1 (not shown).

Sequence analysis of the one clone obtained by expression cloning that had a different restriction enzyme profile predicted an open reading frame of 931 amino acids with about 47% homology to $VEGF_{165}R$/NP-1 (FIG. 4). This human cDNA has a 93% sequence homology with rat neuropilin-2 (NP-2) and is identical to the recently cloned human NP-2 (Chen et al., *Neuron,* 19, 547-559 (1997)).

Expression of $VEGF_{165}R$/NP-1 in Adult Cell Lines and Tissues

Figure 5:
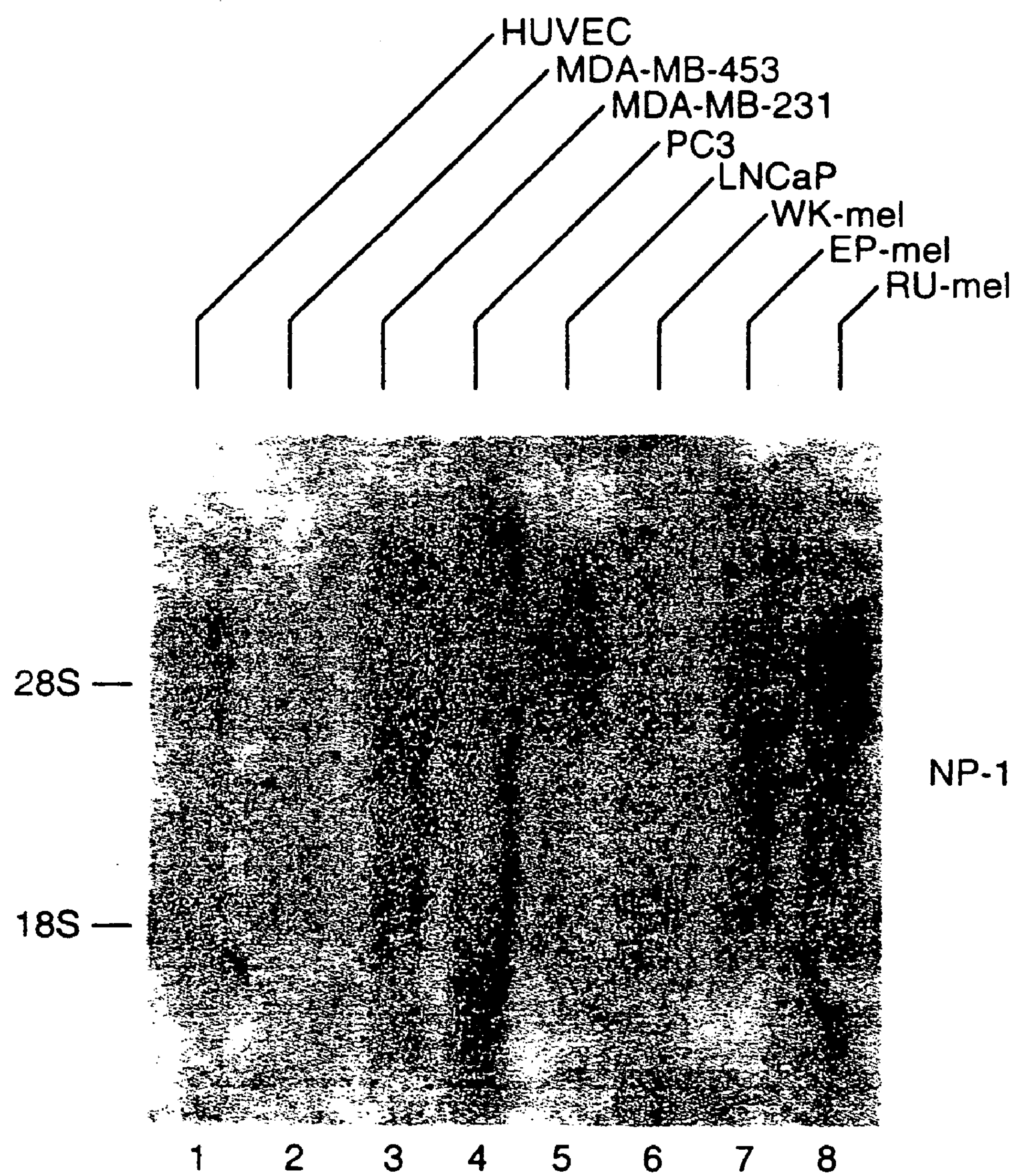
FIG. 5 shows a Northern Blot Analysis of $VEGF_{165}R$/NP-1 Expression in Human EC and Tumor-Derived Cell Lines. Total RNA samples prepared from HUVEC (lane 1) and tumor-derived breast carcinoma, prostate carcinoma and melanoma cell lines as indicated (lanes 2-8) were resolved on a 1% agarose gel and blotted onto a GeneScreen nylon membrane. The membrane was probed with $^{32}P$-labeled $VEGF_{165}R$/NP-1 cDNA, and exposed to X-ray film. Equal RNA loading was demonstrated by ethydium bromide staining of the gel prior to blotting. A major species of $VEGF_{165}R$/NP-1 mRNA of approximately 7 kb was detected in several of the cell lines.

Reports of NP-1 gene expression have been limited so far to the nervous system of the developing embryo (Takagi et al., *Dev. Biol.* 122, 90-100 (1987); Kawakami et al., *J. Neurobiol.* 29, 1-17 (1995); Takagi et al., *Dev. Biol.* 170, 207-222 (1995)). Cell surface $VEGF_{165}R$/NP-1, however, is associated with non-neuronal adult cell types such as EC and a variety of tumor-derived cells (Soker et al., *J. Biol. Chem.* 271, 5761-5767 (1996)). Northern blot analysis was carried out to determine whether cells that crossed-linked $^{125}I-VEGF_{165}$ also synthesized $VEGF_{165}R$/NP-1 mRNA. (FIG. 5). $VEGF_{165}R$/NP-1 mRNA levels were highest in 231 and PC3 cells. $VEGF_{165}R$/NP-1 mRNA was detected to a lesser degree in HUVEC, LNCaP, EP-mel and RU-mel cells. There was little if any expression in MDA-MB-453 and WK-mel cells. The $VEGF_{165}R$/NP-1 gene expression patterns were consistent with our previous results showing that HUVEC, 231, PC3, LNCaP, EP-mel and RU-mel cells bind $^{125}I$-

$VEGF_{165}$ to cell surface $VEGF_{165}$R/NP-1 but that MDA-MB-453 and WK-mel cells do not (Soker et al., *J. Biol. Chem.* 271, 5761-5767 (1996)).

Figure 6:
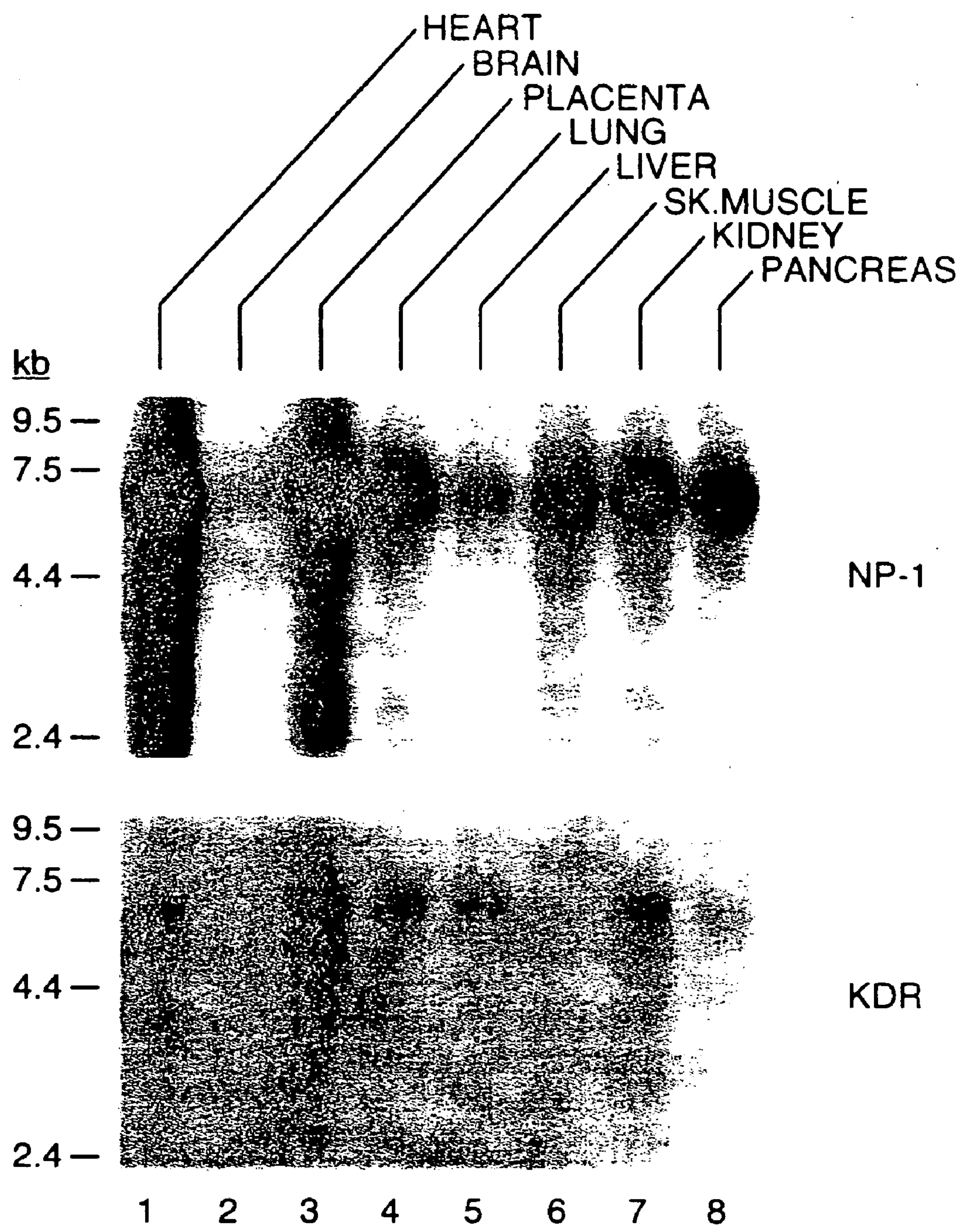
FIG. 6 shows a Northern Blot Analysis of $VEGF_{165}R$/NP-1 and KDR mRNA in Adult Human Tissues. A pre-made Northern blot membrane containing multiple samples of human mRNA (Clonetech) was probed with $^{32}P$-labeled $VEGF_{165}R$/NP-1 cDNA (top) as described in FIG. 5, and then stripped and reprobed with $^{32}P$-labeled KDR cDNA (bottom).

$VEGF_{165}$R/NP-1 gene expression was analyzed also by Northern blot in a variety of adult tissues in comparison to KDR gene expression (FIG. 6). $VEGF_{165}$R/NP-1 mRNA levels were relatively highly in adult heart and placenta and relatively moderate in lung, liver, skeletal muscle, kidney and pancreas. A relatively low level of $VEGF_{165}$R/NP-1 mRNA was detected in adult brain. Interestingly, previous analysis of NP-1 gene expression in mouse and chicken brain suggested that this gene was expressed primarily during embryonic development and was greatly diminished after birth (Kawakami et al., *J Neurobiol.* 29, 1-17 (1995); Takagi et al., *Dev. Biol.* 170, 207-222 (1995)). The tissue distribution of KDR mRNA was similar to that of $VEGF_{165}$R/NP-1 with the exception that it was not expressed highly in the heart. These results indicate that $VEGF_{165}$R/NP-1 is expressed widely in adult non-neuronal tissue, including tissues in which angiogenesis occurs such as heart and placenta.

Characterization of $VEGF_{165}$ Binding to $VEGF_{165}$R/NP-1

Figure 7A:
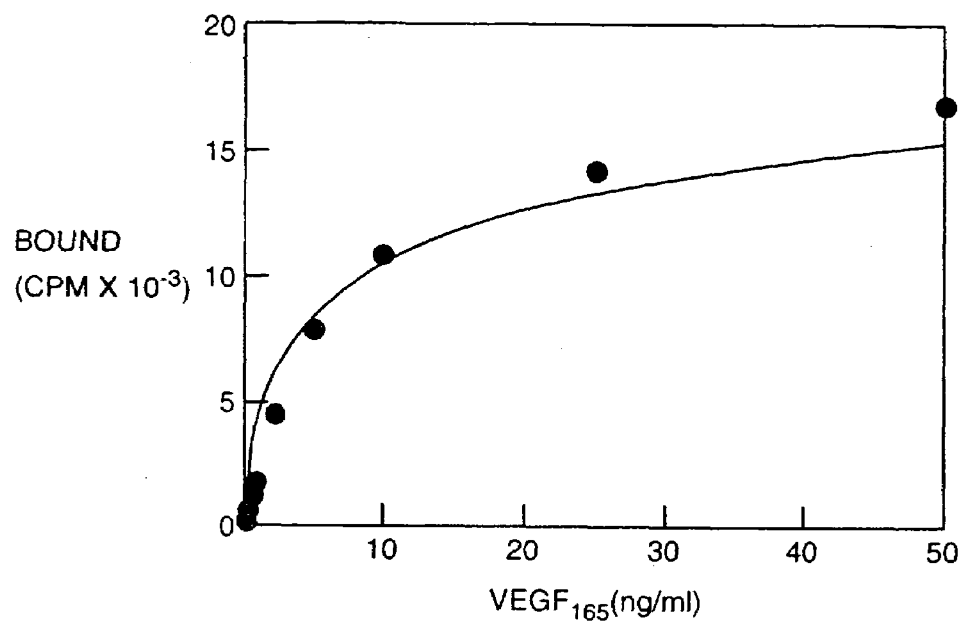
FIGS. 7A and 7B show a Scatchard Analysis of $VEGF_{165}$ binding to $VEGF_{165}R$/NP-1.
Figure 7B:
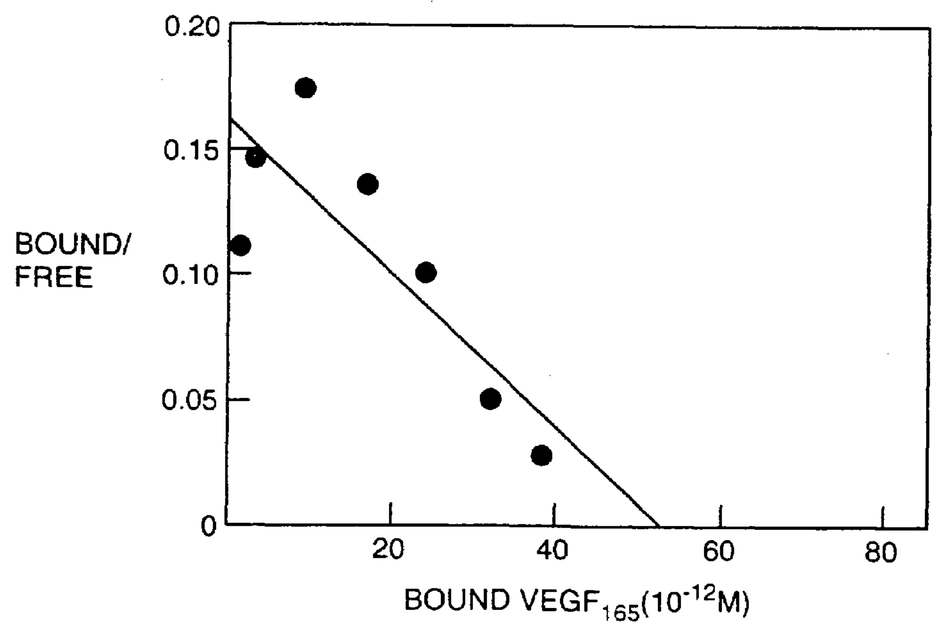

In order to characterize the binding properties of $VEGF_{165}$R/NP-1 porcine aortic endothelial (PAE) cells were transfected with the cDNA of $VEGF_{165}$R/NP-1. The PAE cells were chosen for these expression studies because they express neither KDR, Flt-1 (Waltenberger et al., *J. Biol. Chem.* 269, 26988-26995 (1994)) nor $VEGF_{165}$R. Stable cell lines synthesizing $VEGF_{165}$R/NP-1 (PAE/NP-1) were established and $^{125}$I-$VEGF_{165}$ binding experiments were carried out (FIG. 7). $^{125}$I-$VEGF_{165}$ binding to PAE/NP-1 cells increased in a dose-dependent manner and reached saturation at approximately 30 ng ml demonstrating that $VEGF_{165}$R/NP-1 is a specific $VEGF_{165}$ receptor (FIG. 7A). Scatchard analysis of $VEGF_{165}$ binding revealed a single class of $VEGF_{165}$ binding sites with a $K_d$ of approximately $3.2\times10^{-10}$M and approximately $3\times10^5$ $^{125}$I-$VEGF_{165}$ binding sites per cell (FIG. 7B). Similar $K_d$ values were obtained for several independently-generated PAE/NP-1 clones, although the receptor number varied from clone to clone (not shown). The $K_d$ of $3\times10^{-10}$M for the PAE/NP-1 cell lines is consistent with the 2-2.8×10M $K_d$ values obtained for $VEGF_{165}$R/NP-1 expressed naturally by HUVEC and 231 cells (Gitay-Goren et al., *J. Biol. Chem.* 267, 6093-6098 (1992); Soker et al., *J. Biol. Chem.* 271, 5761-5767 (1996)). The binding of $^{125}$I-$VEGF_{165}$ to PAE/NP-1 cells was enhanced by 1 μg ml heparin (not shown), consistent with previous studies showing that heparin enhances $^{125}$I-$VEGF_{165}$ binding to $VEGF_{165}$R/NP-1 on HUVEC and 231 cells (Gitay-Goren et al., *J. Biol. Chem.* 267, 6093-6098 (1992); Soker et al., *J. Biol. Chem.* 271, 5761-5767 (1996)).

Isoform-specific Binding of VEGF to Cells Expressing $VEGF_{165}$R/NP-1

Figure 8:
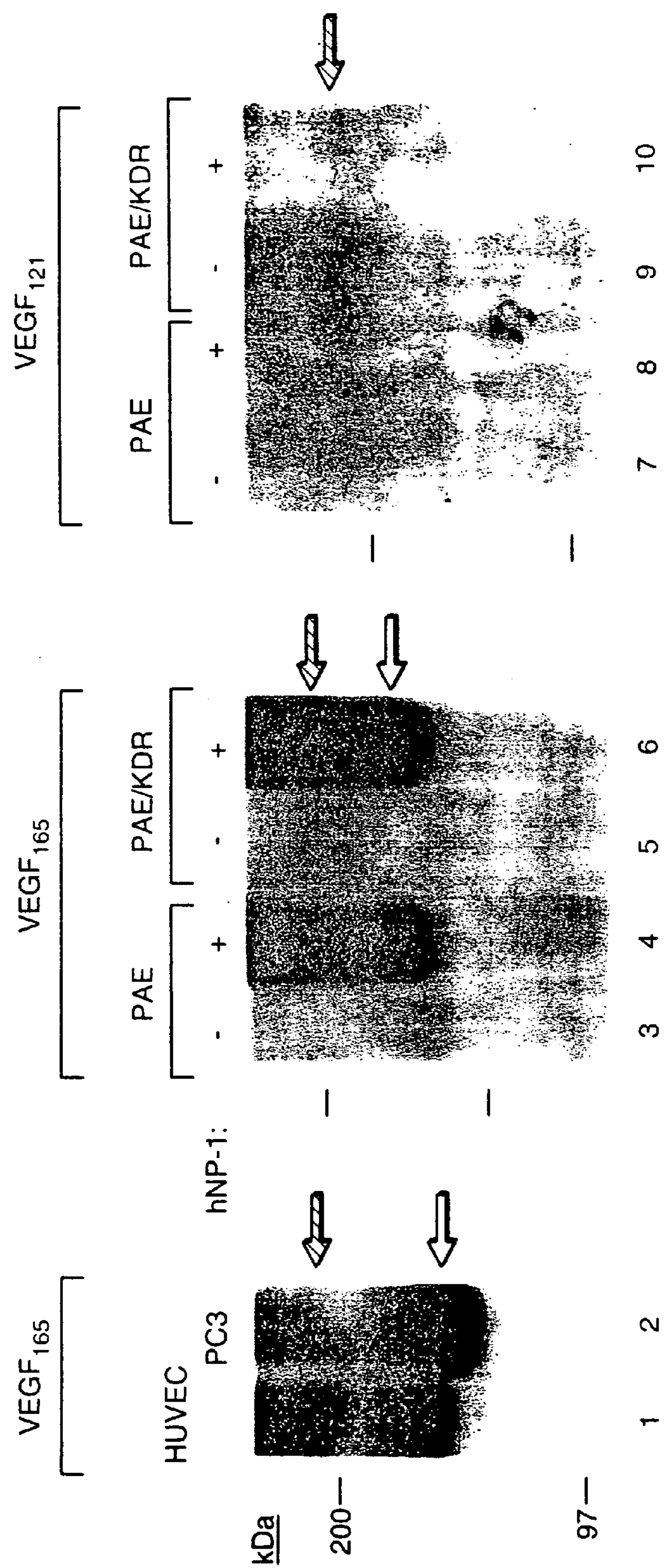
FIG. 8 shows cross-linking of $VEGF_{165}$ and $VEGF_{121}$ to PAE cells Expressing $VEGF_{165}R$/NP-1 and/or KDR. $^{125}I\text{-}VEGF_{165}$ (5 ng/ml) (lanes 1-6) or $^{125}I\text{-}VEGF_{121}$ (10 ng/ml) (lanes 7-10) were bound to subconfluent cultures of HUVEC (lane 1), PC3 (lane 2), PAE (lanes 3 and 7), a clone of PAE cells transfected with human $VEGF_{165}R$/NP-1 cDNA (PAE/NP-1) (lanes 4 and 8), a clone of PAE cells transfected with KDR (PAE/KDR) (lanes 5 and 9), and a clone of PAE/KDR cells transfected with human $VEGF_{165}R$/NP-1 cDNA (PAE/KDR/NP-1) (lanes 6 and 10). The binding was carried out in the presence of 1 μg ml heparin. At the end of a 2 hour incubation, each $^{125}$I-VEGF isoform was chemically cross-linked to the cell surface. The cells were lysed and proteins were resolved by 6% SDS-PAGE. The polacrylamide gel was dried and exposed to X-ray film. Solid arrows denote radiolabeled complexes containing $^{125}$I-VEGF and KDR, open arrows denote radiolabeled complexes containing $^{125}$I-VEGF and $VEGF_{165}R$/NP-1.

$VEGF_{165}$, but not $VEGF_{121}$, binds to $VEGF_{165}$R/NP-1 on HUVEC and 231 cells (Gitay-Goren et al., *J. Biol. Chem.* 271, 5519-5523 (1992); Soker et al., *J. Biol. Chem.* 271, 5761-5767 (1996)). To ascertain whether cells transfected with $VEGF_{165}$R/NP-1 had the same binding specificity. PAE/NP-1 cells were incubated with $^{125}$I-$VEGF_{165}$ or $^{125}$I-$VEGF_{121}$ followed by cross-linking (FIG. 8). $^{125}$I-$VEGF_{165}$ did not bind to parental PAE cells (FIG. 8, lane 3) but did bind to PAE/NP-1 cells via $VEGF_{165}$R/NP-1 (FIG. 8, lane 4). The radiolabeled complexes formed with $VEGF_{165}$R/NP-1 where similar in size to those formed in HUVEC (FIG. 8, lane 1) and PC3 cells (FIG. 8, lane 2). On the other hand, $^{125}$I-$VEGF_{121}$, did not bind to either parental PAE (FIG. 8, lane 7) or to PAE/NP-1 cells (FIG. 8, lane 8). These results demonstrate that the VEGF isoform-specific binding that occurs with cells expressing endogenous $VEGF_{165}$R/NP-1 such as HUVEC, 231 and PC-3 cells, can be replicated in cells transfected with $VEGF_{165}$R/NP-1 cDNA and support the finding that $VEGF_{165}$R and NP-1 are identical.

Co-expression of $VEGF_{165}$R/NP-1 and KDR Modulates $VEGF_{165}$ Binding to KDR To determine whether expression of $VEGF_{165}$R/NP-1 had any effect on $VEGF_{165}$ interactions with KDR. PAE cells that were previously transfected with KDR cDNA to produce stable clones of PAE KDR cells (Waltenberger et al., *J. Biol. Chem.* 269, 26988-26995 (1994)), were transfected with $VEGF_{165}$R/NP-1 cDNA and stable clones expressing both receptors (PAE KDR/NP-1) were obtained. These cells bound $^{125}$I-$VEGF_{165}$ to KDR (FIG. 8, lane 6, upper complex) and to $VEGF_{165}$R/NP-1 (FIG. 8, lane 6, lower complex) to yield a cross-linking profile similar to HUVEC (FIG. 8, lane 1). On the other hand, the PAE/KDR/NP-1 cells bound $^{125}$I-$VEGF_{121}$ to form a complex only with KDR (FIG. 8, lanes 9 and 10), consistent with the inability of $VEGF_{121}$ to bind $VEGF_{165}$R/NP-1.

It appeared that in cells co-expressing KDR and $VEGF_{165}$R/NP-1 (FIG. 8, lane 6), the degree of $^{125}$I-$VEGF_{165}$-KDR 240 kDa complex formation was enhanced compared to the parental PAE/KDR cells (FIG. 8, lane 5). These results were reproducible and the degree of $^{125}$I-$VEGF_{165}$-KDR 240 kDa complex formation in different clones was correlated positively with the levels of $VEGF_{165}$R/NP-1 expressed (not shown). However, it could not be ruled out definitively that these differential KDR binding results were possibly due to clonal selection post-transfection. Therefore, parental PAE/KDR cells where transfected with $VEGF_{165}$R/NP-1 cDNA and $^{125}$I-$VEGF_{165}$ was bound and cross-linked to the cells three days later in order to avoid any diversity of KDR expression among individual clones (FIG. 9). A labeled 240 kDa complex containing KDR was formed in parental PAE KDR cells (FIG. 9, lane 1) and in PAE/KDR cells transfected with the expression vector (FIG. 9, lane 2). However, when $^{125}$I-$VEGF_{165}$ was cross-linked to PAE/KDR cells transiently expressing $VEGF_{165}$R/NP-1, a more intensely labeled 240 kDa complex, about 4 times greater, was observed (FIG. 9, lane 3), compared to parental PAE/KDR cells (FIG. 9, lane 1) and PAE/KDR cells transfected with expression vector (FIG. 9, lane 2). These results suggest that co-expression of KDR and $VEGF_{165}$R/NP-1 genes in the same cell enhances the ability of $VEGF_{165}$ to bind to KDR.

Figure 10:
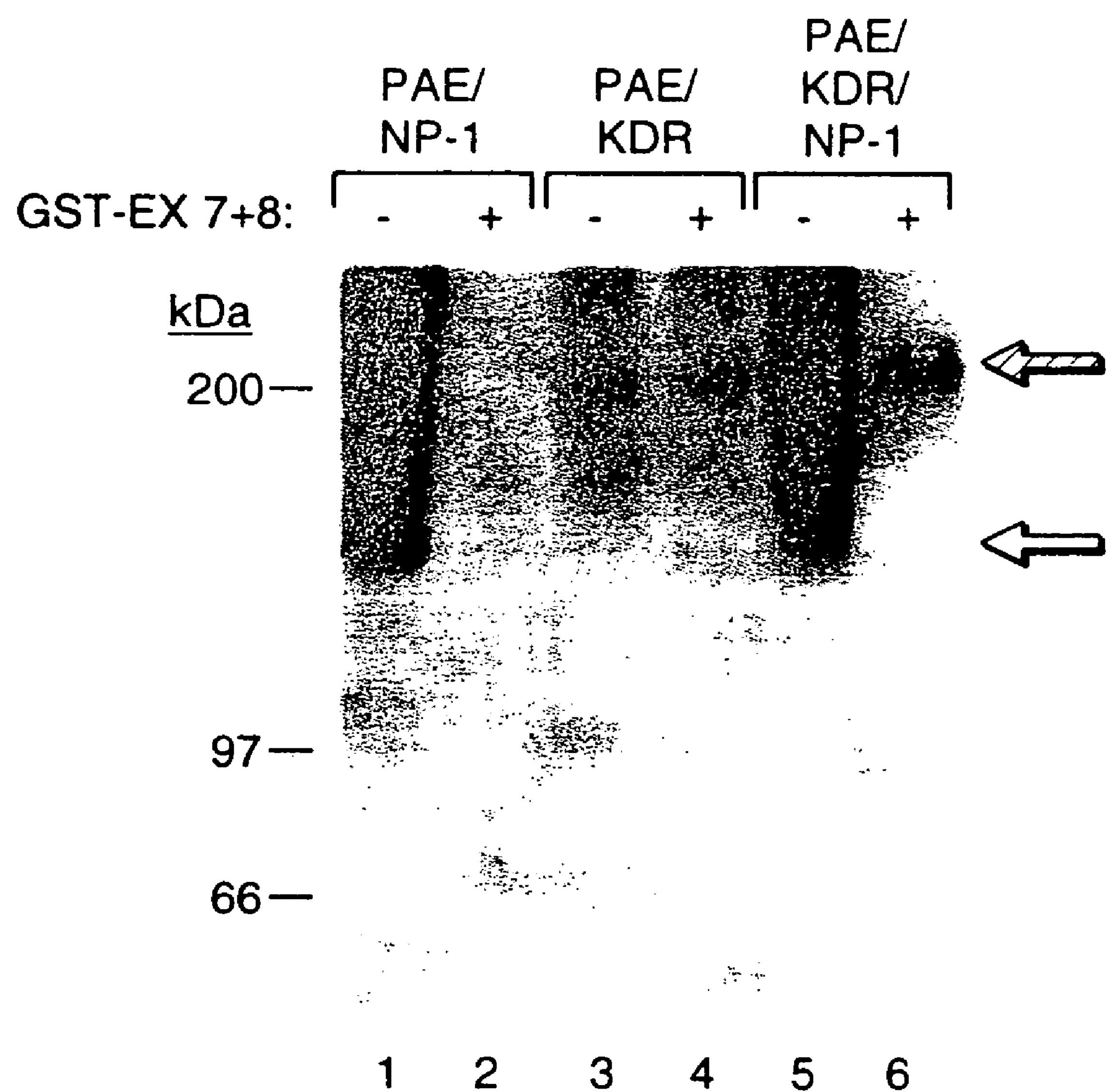
FIG. 10 shows inhibition of $^{125}I\text{-}VEGF_{165}$ binding to $VEGF_{165}R$/NP-1 interferes with its binding to KDR. $^{125}I\text{-}VEGF_{165}$ (5 ng ml) was bound to subconfluent cultures of PAE transfected with human $VEGF_{165}R$/NP-1 cDNA (PAE/NP-1) (lanes 1 and 2), PAE/KDR cells (lanes 3 and 4 and PAE/KDR cells transfected with human $VEGF_{165}R$/NP-1 cDNA (PAE KDR/NP-1) (lanes 5 and 16) in 35 mm dishes. The binding was carried out in the presence (lanes 2, 4, and 6) or the absence (lanes 1, 3, and 5)) of 25 μg/ml GST-Ex 7-8. Heparin (1 μg/ml) was added to each dish. At the end of a 2 hour incubation. $^{125}I\text{-}VEGF_{165}$ as chemically cross-linked to the cell surface. The cells were lysed and proteins were resolved by 6% SDS-PAGE as in FIG. 9. Solid arrows denote radiolabeled complexes containing $^{125}I\text{-}VEGF_{165}$ and KDR, open arrows denote radiolabeled complexes containing $^{125}I\text{-}VEGF_{165}$ and $VEGF_{165}R$/NP-1.

A GST-VEGF Exon 7+8 Fusion Protein Inhibits $VEGF_{165}$ Binding to $VEGF_{165}$R/NP-1 and KDR We have shown that $^{125}$I-$VEGF_{165}$ binds to $VEGF_{165}$R/NP-1 through its exon 7-encoded domain (Soker et al., *J. Biol. Chem.* 271, 5761-5767 (1996)). In addition, a GST fusion protein containing the peptide encoded by VEGF exon 7-8 (GST-Ex 7+8), inhibits completely the binding of $^{125}$I-$VEGF_{165}$ to $VEGF_{165}$R/NP-1 associated with 231 cells and HUVEC (Soker et al., *J. Biol. Chem.* 271, 5761-5767 (1996); Soker et al., *J. Biol. Chem.* 272, 31582-31588 (1997)). When, added to PAE/NP-1 cells, the fusion protein completely inhibited binding to $VEGF_{165}$R/NP-1 (FIG. 10, lane 2 compared to lane 1). On the other hand, it did not inhibit $^{125}$I-$VEGF_{165}$ binding at all to KDR (FIG. 10, lane 4 compared to lane 3). Thus, these results demonstrate that GST-Ex 7+8 binds directly to $VEGF_{165}$R/NP-1 but does not bind to KDR. The effects of GST-Ex 7+8 are different, however, in cells co-expressing both $VEGF_{165}$R/NP-1 and KDR (PAE/KDR/NP-1). Consistent with the results in FIGS. 8 and 9, the degree of $^{125}$I-VEGF$_{165}$ binding to KDR in PAE/KDR/NP-1 cells (FIG. 10, lane 5) was greater than to the parental PAE/KDR cells (FIG. 10, lane 3). Interestingly, in PAE/KDR/NP-1 cells, GST-Ex 7+8 inhibited not only $^{125}$I-VEGF$_{165}$ binding to VEGF$_{165}$R/NP-1 completely as expected, but it also inhibited binding to KDR substantially which was unexpected (FIG. 10, lane 6 compared to lane 5). In the presence of GST-Ex 7+8, binding of $^{125}$I-VEGF$_{165}$ to KDR in these cells was reduced to the levels seen in parental PAE/KDR cells not expressing VEGF$_{165}$R/NP-1 (FIG. 10, lane 6 compared to lanes 3 and 4). Since the fusion protein does not bind directly to KDR, these results suggest that inhibiting the binding of $^{125}$I-VEGF$_{165}$ to VEGF$_{165}$R/NP-1 directly, inhibits its binding to KDR indirectly. Taken together, the results in FIGS. 8, 9 and 10 suggest that interactions of VEGF$_{165}$ with VEGF$_{165}$R/NP-1 enhance VEGF interactions with KDR.

Neuropilin-1 is an Isoform-specific VEGF$_{165}$ Receptor

Recently, we described a novel 130-135 kDa VEGF cell surface receptor that binds VEGF$_{165}$ but not VEGF$_{121}$ and that we named, accordingly, VEGF$_{165}$R (Soker et al., *J. Biol. Chem.* 271, 5761-5767 (1996)). We have now purified VEGF$_{165}$R, expression cloned its cDNA, and shown it to be identical to human neuropilin-1 (NP-1) (He and Tessier-Lavigne, *Cell* 90 739-751 (1997)). The evidence that VEGF$_{165}$R is identical to NP-1 and that NP-1 serves as a receptor for VEGF$_{165}$ is as follows: i) purification of VEGF$_{165}$R protein from human MDA-MB-231 (231) cells using VEGF affinity, yielded a 130-140 kDa doublet upon SDS-PAGE and silver stain. N-terminal sequencing of both proteins yielded the same N-terminal sequence of 18 amino acids that demonstrated a high degree of homology to mouse NP-1 (Kawakami et al., *J. Neurobiol.* 29, 1-17 (1995)): ii) After we purified VEGF$_{165}$R from human 231 cells, the cloning of human NP-1 was reported (He and Tessier-Lavigne, *Cell* 90, 739-751 (1997)) and the N-terminal sequence of human VEGF$_{165}$R was found to be identical to a sequence in the N-terminal region of human NP-1: iii) Expression cloning using a 231 cell cDNA library resulted in isolation of several cDNA clones and their sequences were identical to the human NP-1 cDNA sequence (He and Tessier-Lavigne, *Cell* 90, 739-751 (1997)). The combination of purification and expression cloning has the advantage over previous studies where only expression cloning was used (He and Tessier-Lavigne, *Cell* 90, 739-751 (1997); Kolodkin et al., *Cell* 90, 753-762 (1997)), in allowing unambiguous identification of the NP-1 protein N-terminus; iv) Northern blot analysis of NP-1 gene expression was consistent with previous $^{125}$I-VEGF$_{165}$ cross-linking experiments (Soker et al., *J. Biol. Chem.* 271, 5761-5767 (1996)). Cells that bound VEGF$_{165}$ to VEGF$_{165}$R synthesized relatively abundant NP-1 mRNA while cells that showed very little if any VEGF$_{165}$ binding, did not synthesize much if any NP-1 mRNA; v) when NP-1 was expressed in PAE cells, the transfected, but not the parental cells, were able to bind VEGF$_{165}$ but not VEGF$_{121}$, consistent with the isoform specificity of binding previously shown for HUVEC and 231 cells (Soker et al., *J. Biol. Chem.* 271, 5761-5767 (1996)). Furthermore, the $K_d$ of $^{125}$I-VEGF$_{165}$ binding of to PAE expressing NP-1 was about $3\times10^{-10}$M, consistent with previous $K_d$ binding values of 2-2.8$\times10^{-10}$M for 231 cells and HUVEC (Soker et al., *J. Biol. Chem.* 271, 5761-5767 (1996)): and vi) The binding of VEGF$_{165}$ to cells expressing NP-1 post-transfection was more efficient in the presence of heparin as was the binding of this ligand to HUVEC and 231 cells (Gitay-Goren et al., *J. Biol. Chem.* 267, 6093-6098 (1992); Soker et al., *J. Biol. Chem.* 271, 5761-5761 (1996)). Taken together, these results show not only that VEGF$_{165}$R is identical to NP-1 but that it is a functional receptor that binds VEGF$_{165}$ in an isoform-specific manner. Accordingly, we have named this VEGF receptor VEGF$_{165}$R/NP-1.

In addition to the expression cloning of VEGF$_{165}$R/NP-1 cDNA, another human cDNA clone was isolated whose predicted amino acid sequence was 47% homologous to that of VEGF$_{165}$R/NP-1 and over 90% homologous to rat neuropilin-2 (NP-2) which was recently cloned (Kolodkin et al., *Cell* 90, 753-762 (1997)). NP-2 binds members of the collapsin semaphorin family selectively (Chen et al., *Neuron* 19, 547-559 (1997)).

The discovery that NP-1 serves as a receptor for VEGF$_{165}$ was a surprise since NP-1 had previously been shown to be associated solely with the nervous system during embryonic development (Kawakami et al., *J. Neurobiol.* 29, 1-17 (1995); Takagi et al., *Dev. Biol.* 170, 207-222 (1995)) and more recently as a receptor for members of the collapsin semaphorin family (He and Tessier-Lavigne, *Cell* 90739-751 (1997); Kolodkin et al., *Cell* 90, 753-762 (1997)). NP-1 is a 130-140 kDa transmembrane glycoprotein first identified in the developing Xenopus optic system (Takagi et al., *Dev. Biol.* 122, 90-100 (198); Takagi et al., *Neuron* 7, 295-307 (1991)). NP-1 expression in the nervous system is highly regulated spatially and temporally during development and in particular is associated with those developmental stages when axons are actively growing to form neuronal connections (Fujisawa et al., *Dev. Neurosci.* 17, 343-349 (1995); Kawakami et al., *J. Neurobiol.* 29, 1-17 (1995): Takagi et al., *Dev. Biol.* 170, 207-222 (1995)). The NP-1 protein is associated with neuronal axons but not the stomata (Kawakami et al., *J. Neurobiol.* 29, 1-17 (1995)). Functionally, neuropilin has been shown to promote neurite outgrowth of optic nerve fibers in vitro (Hirata et al., *Neurosci. Res.* 17, 159-169 (1993)) and to promote cell adhesiveness (Tagaki et al., *Dev. Biol.* 170, 207-222 (1995)). Targeted disruption of NP-1 results in severe abnormalities in the trajectory of efferent fibers of the peripheral nervous system (Kitsukawa et al., *Neuron* 19, 995-1005 (1997)). Based on the these studies, it has been suggested that NP-1 is a neuronal cell recognition molecule that plays a role in axon growth and guidance (Kawakami et al., *J. Neurobiol.* 29, 1-17 (1995); He and Tessier-Lavigne, *Cell* 90, 739-751 (1997): Kitsukawa et al., *Neuron* 19, 995-1005 1997; Kolodkin et al., *Cell* 90, 753-762 (1997)).

Our results are the first to show that VEGF$_{165}$R/NP-1 is also expressed in adult tissues, in contrast to the earlier studies that have shown that NP-1 expression in Xenopus, chicken and mouse is limited to the developmental and early post-natal stages (Fujisawa et al., *Dev. Neurosci.* 17, 343-349 (1995): Kawakami et al., *J. Neurobiol.* 29, 1-17 (1995): Takagi et al., *Dev. Biol.* 170, 207-222 (1995)). For example, in mice, NP-1 is expressed in the developing nervous system starting in the dorsal root ganglia at day 9 and ceases at day 15 (Kawakami et al., *J. Neurobiol.* 29, 1-17 (1995). Our Northern blot analysis of human adult tissue demonstrates relatively high levels of VEGF$_{165}$R/NP-1 mRNA transcripts in heart, placenta, lung, liver, skeletal muscle, kidney and pancreas. Interestingly, there is very little relative expression in adult brain, consistent with the mouse nervous system expression studies (Kawakami et al., *J. Neurobiol.* 29, 1-17 (1995)). VEGF$_{165}$R/NP-1 is also expressed in a number of cultured non-neuronal cell lines including EC and a variety of tumor-derived cells. A possible function of $VEGF_{165}R$/NP-1 in these cells is to mediate angiogenesis as will be discussed below.

In addition, NP-1 has been identified as a receptor for the collapsin/semaphorin family by expression cloning of a cDNA library obtained from rat E14 spinal cord and dorsal root ganglion (DRG) tissue (He and Tessier-Lavigne, *Cell* 90, 739-751 (1997); Kolodkin et al., *Cell* 90, 753-762 (1997)). The collapsin semaphorins (collapsin-D-I/Sema III Sem D) comprise a large family of transmembrane and secreted glycoproteins that function in repulsive growth cone and axon guidance (Kolodkin et al., *Cell* 75, 1389-1399 (1993)). The repulsive effect of sema III for DRG cells was blocked by anti-NP-1 antibodies (He and Tessier-Lavigne, *Cell* 90, 739-751 (1997); Kolodkin et al., *Cell* 90, 753-762 (1997)). The $K_d$ of sema III binding to NP-1, $0.15\text{-}3.25\times10^{-10}$ M (He and Tessier-Lavigne, *Cell* 90, 739-751 (1997); Kolodkin et al., *Cell* 90, 753-762 (1997)) is similar to that of $VEGF_{165}$ binding $VEGF_{165}$NP-1, which is about $3\times10^{-10}$ M. These results indicate that two structurally different ligands with markedly different biological activities. VEGF-induced stimulation of EC migration and proliferation on one hand, and sema III-induced chemorepulsion of neuronal cells, on the other hand, bind to the same receptor and with similar affinity. An interesting question is whether the two ligands bind to the same site on $VEGF_{165}R$/NP-1 or to different sites. $VEGF_{165}R$/NP-1 has five discrete domains in its ectodomain, and it has been suggested that this diversity of protein modules in NP-1 is consistent with the possibility of multiple binding ligands for NP-1 (Takagi et al., *Neuron* 7, 295-307 (1991); Feiner et al., *Neuron* 19 539-545 (1997); He and Tessier-Lavigne, *Cell* 90 739-751(1997). Preliminary analysis does not indicate any large degree of sequence homology between sema III and VEGF exon 7 which is responsible for VEGF binding to $VEGF_{165}R$/NP-1 (Soker et al., *J. Biol. Chem.* 271, 5761-5767 (1996)). However there may be some 3-dimensional structural similarities between the two ligands. Since both neurons and blood vessels display branching and directional migration, the question also arises as to whether $VEGF_{165}$ displays any neuronal guidance activity and whether sema III has any EC growth factor activity. These possibilities have not been examined yet. However, it may be that VEGF requires two receptors. KDR and NP-1 for optimal EC growth factor activity (Soker et al., *J. Biol. Chem.* 272, 31582-31588 (1997)) and that sema III requires NP-1 and an as yet undetermined high affinity receptor for optimal chemorepulsive activity (Feiner et al., *Neuron* 19, 539-545 (1997;) He and Tessier-Lavigne, *Cell* 90; 739-751 (1997); Kitsukawa et al., *Neuron* 19, 995-1005 (1997)), so that the presence of NP-1 alone might not be sufficient for these ligands to display novel biological activities. Future studies will determine whether there are any connections between the mechanisms that regulate neurogenesis and angiogenesis.

Figure 11C:
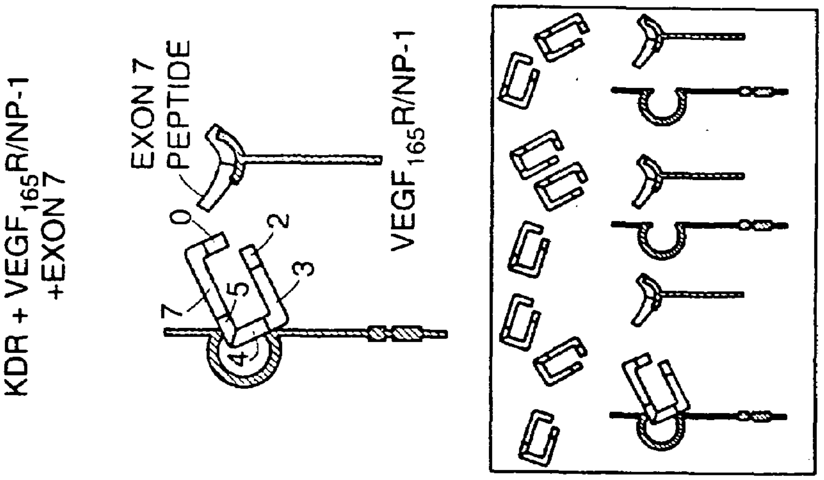
FIGS. 11A-C show a model for $VEGF_{165}R$/NP-1 modulation of $VEGF_{165}$ Binding to KDR. 11A.Cells expressing KDR alone. 11B.Cells co-expressing KDR and $VEGF_{165}R$/NP-1. 11C.Cells co-expressing KDR and $VEGF_{165}R$/NP-1 in the presence of GST-Ex 7+8 fusion protein.
Figure 11B:
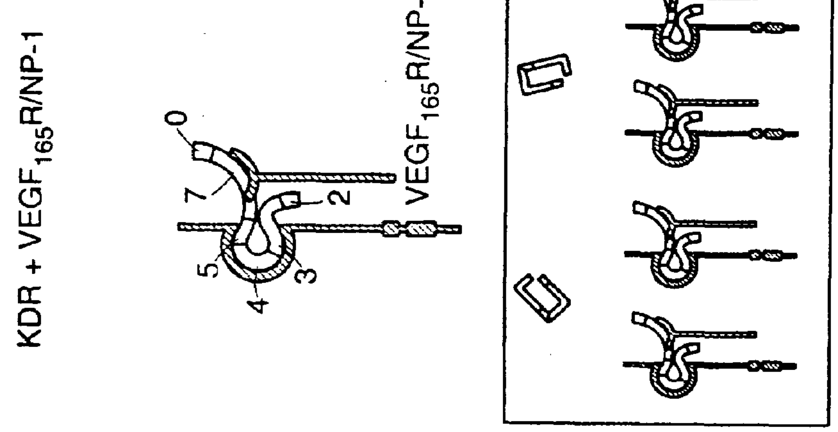
Figure 11A:
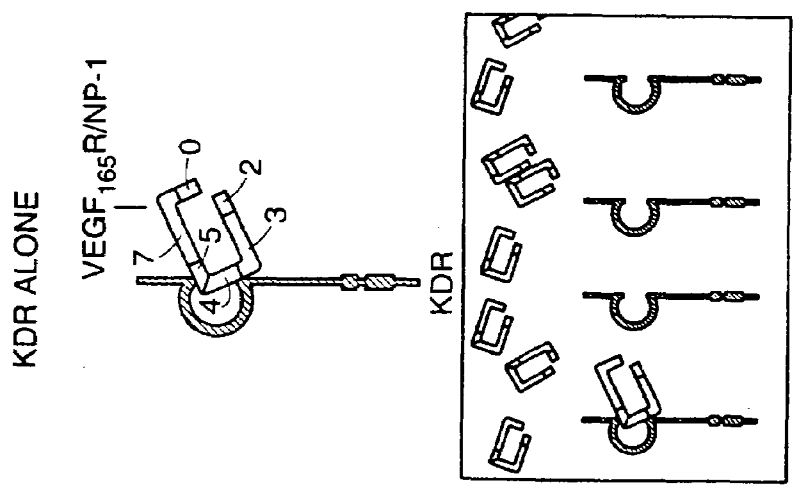

$VEGF_{165}R$/NP-1 Role Angiogenesis $VEGF_{165}R$/NP-1 modulates the binding of $VEGF_{165}$ to KDR, a high affinity RTK that is an important regulator of angiogenesis as evidenced by KDR knock out experiments in mice (Shalaby et al., *Nature* 376, 62-66 (1995). The affinity of KDR for $VEGF_{165}$ is about 50 times greater than for $VEGF_{165}R$/NP-1 (Gitay-Goren et al., *J. Biol. Chem.* 287, 6003-6096 (1992); Waltenberger et al., *J. Biol. Chem.* 269, 26988-26955 (1994)). When $VEGF_{165}R$/NP-1 and KDR are co-expressed, the binding of $^{125}$I-$VEGF_{165}$ to KDR is enhanced by about 4-fold compared to cells expressing KDR alone. The enhanced binding can be demonstrated in stable clones co-expressing $VEGF_{165}R$/NP-1 and KDR (PAE KDR/NP-1 cells), and also in PAE KDR cells transfected transiently with $VEGF_{165}R$/NP-1 cDNA where clonal selection does not take place. Conversely, when the binding of $^{125}$I-$VEGF_{165}$ to $VEGF_{165}R$/NP-1 in PAE KDR/NP-1 cells is inhibited completely by a GST fusion protein containing VEGF exons 7-8 (GST-Ex 7+8), the binding to KDR is inhibited substantially, down to the levels observed in cells expressing KDR alone. The fusion protein binds to $VEGF_{165}R$/NP-1 directly but is incapable of binding to KDR directly (Soker et al., *J. Bid. Chem.* 272, 31582-31588 (1997)). Although, not wishing to be bound by theory, we believe that $VEGF_{165}$ binds to $VEGF_{165}R$/NP-1 via the exon 7-encoded domain and facilitates $VEGF_{165}$ binding to KDR via the exon 4-encoded domain (FIG. 11). $VEGF_{165}R$/NP-1, with its relatively high receptor cell number, about $0.2\text{-}2\times10^5$ (Gitay-Goren et al., *J. Bid. Chem.* 287, 6003-6096 (1992); Soker et al., *J. Bid. Chem.* 271, 5761-5767 (1996)), appears to serve to concentrate $VEGF_{165}$ on the cell surface, thereby providing greater access of $VEGF_{165}$ to KDR. Alternatively, binding to $VEGF_{165}R$/NP-1, $VEGF_{165}$ undergoes a conformational change that enhances its binding to KDR. The end result would be elevated KDR signaling and increased VEGF activity. Although we can demonstrate enhanced binding to KDR, to date we have not been able to demonstrate enhanced VEGF mitogenicity for PAE/KDR/NP-1 cells compared to PAE KDR cells. One reason is that these cell lines do not proliferate readily in response to VEGF as do HUVEC (Waltenberger et al., *J. Biol. Chem.* 269, 26988-26995 (1994). Nevertheless, we have shown that $VEGF_{165}$, which binds to both KDR and $VEGF_{165}R$/NP-1, is a better mitogen for HUVEC than is $VEGF_{121}$, which binds only to KDR (Keyt et al., *J. Biol. Chem.* 271, 5638-5646 (1996b); Soker et al., *J. Biol. Chem.* 272, 31582-31588 (1997). Furthermore, inhibiting $VEGF_{165}$ binding to $VEGF_{165}R$/NP-1 on HUVEC by GST-EX 7-8, inhibits binding to KDR and also inhibits $VEGF_{165}$-induced HUVEC proliferation, down to the level induced by $VEGF_{121}$ (Soker et al., *J. Biol. Chem.* 272, 31582-31588 (1997)). Taken together, these results suggest a role for $VEGF_{165}R$/NP-1 in mediating $VEGF_{165}$, but not $VEGF_{121}$ mitogenic activity. The concept that dual receptors regulate growth factor binding and activity has been previously demonstrated for TGF-β, bFGF and NGF (Lopez-Casillas et al., *Cell* 67, 785-795 (1991); Yayon et al., *Cell* 64, 841-848 (1991); Barbacid, *Curr. Opin. Cell Biol.* 7, 148-155 (1995)).

Another connection between $VEGF_{165}R$/NP-1 and angiogenesis comes from studies in which NP-1 was overexpressed ectopically in transgenic mice (Kitsuskawa et al., *Develop.* 121, 4309-4318 (1995)). NP-1 overexpression resulted in embryonic lethality and the mice died in utero no later than on embryonic day 15.5 and those that survived the best had lower levels of NP-1 expression. Mice overexpressing NP-1 displayed morphologic abnormalities in a limited number of non-neural tissues such as blood vessels, the heart and the limbs. NP-1 was expressed in both the EC and in the mesenchymal cells surrounding the EC. The embryos possessed excess and abnormal capillaries and blood vessels compared to normal counterparts and in some cases dilated blood vessels as well. Some of the chimeric mice showed hemorrhaging, mainly in the head and neck. These results are consistent with the possibility that ectopic overexpression of $VEGF_{165}R$/NP-1 results in inappropriate $VEGF_{165}$ activity thereby mediating enhanced and/or aberrant angiogenesis. Another piece of evidence for a link between NP-1 and angiogenesis comes from a recent report showing that in mice targeted for disruption of the NP-1 gene, the embryos have severe abnormalities in the peripheral nervous system but that their death in utero at days 10.5-12.5 is most probably due to anomalies in the cardiovascular system (Kitsukawa et al., *Neuron* 19, 995-1005 (1997)).

$VEGF_{165}$R/NP-1 is Associated with Tumor-derived Cells

The greatest degree of $VEGF_{165}$R/NP-1 expression that we have detected so far occurs in tumor-derived cells such as 231 breast carcinoma cells and PC3 prostate carcinoma cells, far more than occurs in HUVEC. The tumor cells express abundant levels of $VEGF_{165}$R/NP-1 mRNA and about 200,000 $VEGF_{165}$ receptors/cell (Soker et al., *J. Biol. Chem.* 271, 5761-5767 (1996)). On the other hand, these tumor cells do not express KDR or Flt-1 so that $VEGF_{165}$R/NP-1 is the only VEGF receptor associated with these cells. The tumor cells are therefore useful for testing whether $VEGF_{165}$R/NP-1 is a functional receptor for $VEGF_{165}$ in the absence of a KDR background. To date, we have not been able to show that $VEGF_{165}$R/NP-1 mediates a $VEGF_{165}$ signal in tumor-derived cells as measured by receptor tyrosine phopshorylation. Nevertheless, $VEGF_{165}$ might have an effect on tumor cells by inducing some, as yet undetermined activity such as enhanced survival, differentiation, or motility. A recent report has demonstrated that glaucoma cells express a 190 kDa protein that binds $VEGF_{165}$ but not $VEGF_{165}$ efficiently (Omura et al., *J. Biol. Chem.* 272, 23317-23322 (1997)). No stimulation of tyrosine phosphorylation could be demonstrated upon binding of $VEGF_{165}$ to this receptor. Whether the 190 kDa isoform-specific receptor is related to $VEGF_{165}$R/NP-1 is not known presently.

$VEGF_{165}$R/NP-1 may have a storage and sequestration function for $VEGF_{165}$. One might envision that $VEGF_{165}$ is produced by a tumor cell and binds to $VEGF_{165}$R/NP-1 on that cell via the exon 7-encoded domain (Soker et al., *J. Biol. Chem.* 271, 5761-5767 (1996)). The stored $VEGF_{165}$ could be then released to stimulate tumor angiogenesis in a paracrine manner. Alternatively, $VEGF_{165}$R/NP-1 may mediate a juxtacrine effect in which $VEGF_{165}$ is bound to $VEGF_{165}$R/NP-1 on a tumor cell via the exon 7-encoded domain and is also bound to KDR on a neighboring EC via the exon 4-encoded domain (Keyt et al., *J. Biol. Chem.* 271, 5638-5646 (1996b)). Such a mechanism could result in a more efficient way for tumor cells to attract EC, thereby enhancing tumor angiogenesis.

In summary, we have demonstrated by independent purification and expression cloning methods that the VEGF isoform specific receptor, $VEGF_{165}$R, is identical to NP-1, a cell surface protein previously identified as playing a role in embryonic development of the nervous system and as being a receptor for the collapsins semaphorins. Furthermore, binding to $VEGF_{165}$R/NP-1 enhances the binding of $VEGF_{165}$ to KDR on EC and rumor cells.

Experimental Rationale

We have discovered that tumor cell neuropilin-1 mediates tumor cell motility and thereby metastasis. In a Boyden chamber motility assay, $VEGF_{165}$ (50 ng/ml) stimulates 231 breast carcinoma cell motility in a dose-response manner, with a maximal 2-fold stimulation (FIG. 15A). On the other hand, $VEGF_{121}$ has no effect on motility of these cells (FIG. 15B). Since 231 cells do not express KDR or Flt-1, these results suggest that tumor cells are directly responsive to $VEGF_{165}$ and that $VEGF_{165}$ might signal tumor cells via neuropilin-1. Possible candidates for mediating $VEGF_{165}$ induced motility of carcinoma cells are PI3-kinase (PI3-K) (Carpenter, et al. ( 1996) *Curr. Opin. Cell Biol.* 8: 153-158). Since 231 cells do not express KDR or Flt-1, these results suggest that tumor cells are directly responsive to $VEGF_{165}$ and that $VEGF_{165}$ might signal tumor cells via neuropilin-1.

The other type of evidence is that neuropilin-1 expression might be associated with tumor cell motility. We have analyzed two variants of Dunning rat prostate carcinoma cells. AT2.1 cells, which are of low motility and low metastatic potential, and AT3.1 cells, which are highly motile, and metastatic. Cross-linking and Northern blot analysis show that AT3.1 cells express abundant neuropilin-1, capable of binding $VEGF_{165}$, while AT2.1 cells don't express neuropilin-1 (FIG. 16). Immunostaining of tumor sections confirms the expression of neuropilin-1 in AT3.1, but not AT2.1 tumors (FIG. 17). Furthermore, the immunostaining shows that in subcutaneous AT3.1 and PC3 tumors, the tumor cells expressing neuropilin-1 are found preferentially at the invading front of the tumor/dermis boundary (FIG. 17). To determine more directly whether neuropilin-1 expression is correlated with enhanced motility, neuropilin-1 was overexpressed in AT2.1 cells (FIG. 18). Three stable clones of AT2.1 cells overexpressing neuropilin-1 had enhanced motility in the Boyden chamber assay. These results indicate that expression of neuropilin-1 in AT2.1 cells enhances their motility. Taken together, it appears that neuropilin-1 expression on tumor cells is associated with the motile, metastatic phenotype.

EXAMPLE 2

Experimental Procedures

1. Collapsin semaphorins. Expression plasmids for expressing and purifying His-tagged collapsin-1 from transfected 293T cells can be produced according to the methods of (Koppel, et al. (1998) J. Biol. Chem. 273: 15708-15713, Feiner, et al. (1997) *Neuron* 19: 539-545.). Expression vectors for expressing sema E and sema IV alkaline phosphate (AP) conjugates in cells are disclosed in (He Z, Tessier-Lavigne M. (1997). Neuropilin is a receptor for the axonal chemorepellent semaphorin III. Cell 90: 739-751.). Migration was measured in a Boyden chamber Falk, et al., *J. Immunol.* 118:239-247 (1980) with increasing concentration of recombinant chick collapsin-1 in the bottom cell and PAE cell transfectants in the upper well.

Aortic Ring Assay. 200 gram rats were sacrificed and the aorta is dissected between the aortic arch and kidney artery and the adipofibrotic tissue around the aorta was removed. Aortic rings were sliced at 1 mm intervals and embedded in type I collagen gels. Each ring was cultured in one well of a 48-well plate with serum-free endothelial cell medium (GIBCO). The number of microvessels were counted in each ring using a phase microscope (Miao, et al. (1997). *J. Clin. Invest.* 99: 1565-1575).

We established several endothelial cell lines by transfection of parental porcine aortic endothelial cells (PAE), which normally do not express VEGF receptors (Soker, et al. (1998) *Cell* 92: 735-745). The cell lines included PAE cells expressing neuropilin-1 alone (PAE/NP1). PAE cells expressing KDR alone (PAE/KDR) and PAE cells expressing both neuropilin-1 and KDR (PAE/NP1/KDR). Collapsin-1 was obtained from Dr. Jon Raper, University of Pennsylvania (Luo, et al. (1993) *Cell* 75: 217-227.).

Binding studies demonstrated that $^{125}$I-collapsin-1 could bind to PAE/NP1 cells and PAE/NP1 KDR cells but not at all to PAE or PAE KDR cells.

In a Boyden chamber assay, collapsin-1 at 50-100 collapsin units/ml (CU) inhibited the basal migration of PAE/NP and PAE/NP1/KDR cells by 70% but had no inhibitory effect, whatsoever, on basal PAE or PAE/KDR cell migration (FIG. 20). This effect is fairly potent since 1 CU represents about 3 ng ml protein. The collapsin-1 inhibitory effect was inhibited by anti-neuropilin-1 antibodies. These results indicate that collapsins can inhibit the migration of non-neuronal endothelial cells as long as they express neuropilin-1.

Collapsin-1 inhibited the migration of PAE/NP and PAE/NP KDR cells in the presence of $VEGF_{165}$, to the same degree, the baseline being higher. We have also found that addition of collapsin in a rat aortic ring assay (a model for angiogenesis in vitro) inhibits the migration of endothelial cells out of the ring, and endothelial tube formation (FIG. 21).

The references cited throughout the specification are incorporated herein by reference.

The present invention has been described with reference to specific embodiments. However, this application is intended to cover those changes and substitutions which may be made by those skilled in the art without departing from the spirit and the scope of the appended claims.

What is claimed:

1. A method of inhibiting angiogenesis in a subject in need thereof comprising, administering to said subject an antibody, or fragment thereof, that specifically binds an extracellular domain of a neuropilin receptor having the amino acid sequence of SEQ ID NO: 2 and inhibits VEGF from binding to the receptor.

2. The method of claim 1, wherein the antibody is a monoclonal antibody.

3. The method of claim 1, wherein the antibody is a polyclonal antibody.

4. The method of claim 1, wherein the fragment is an Fab, Fab', F(ab')2 or Fv fragment.

5. The method of claim 1, wherein the antibody is a humanized antibody.

* * * * *

SEQUENCE LISTING

```
<160> NUMBER OF SEQ ID NOS: 11

<210> SEQ ID NO 1
<211> LENGTH: 5653
<212> TYPE: DNA
<213> ORGANISM: human

<400> SEQUENCE: 1

aagggagagg aagccggagc taaatgacag gatgcaggcg acttgagaca caaaaagaga     60

agcgttcctc tcggatccag gcattgcctc gctgctttct tttctccaag acgggctgag    120

gattgtacag ctctaggcgg agttggggct cttcggatcg cttagattct cctctttgct    180

gcatttcccc ccacgtcctc gttctcccgc gtctgcctgc ggacccggag aagggagaat    240

ggagaggggg ctgccgctcc tctgcgccgt gctcgccctc gtcctcgccc cggccggcgc    300

ttttcgcaac gataaatgtg gcgatactat aaaaattgaa agccccgggt accttacatc    360

tcctggttat cctcattctt atcacccaag tgaaaaatgc gaatggctga ttcaggctcc    420

ggacccatac cagagaatta tgatcaactt caaccctcac ttcgatttgg aggacagaga    480

ctgcaagtat gactacgtgg aagtgttcga tggagaaaat gaaaatggac attttagggg    540

aaagttctgt ggaaagatag cccctcctcc tgttgtgtct tcagggccat ttctttttat    600

caaatttgtc tctgactacg aaacacatgg tgcaggattt tccatacgtt atgaaatttt    660

caagagaggt cctgaatgtt cccagaacta cacaacacct agtggagtga taaagtcccc    720

cggattccct gaaaaatatc ccaacagcct tgaatgcact tatattgtct ttgcgccaaa    780

gatgtcagag attatcctgg aatttgaaag ctttgacctg gagcctgact caaatcctcc    840

agggggggatg ttctgtcgct acgaccggct agaaatctgg gatggattcc ctgatgttgg    900

ccctcacatt gggcgttact gtggacagaa aacaccaggt cgaatccgat cctcatcggg    960

cattctctcc atggtttttt acaccgacag cgcgatagca aaagaaggtt tctcagcaaa   1020

ctacagtgtc ttgcagagca gtgtctcaga agatttcaaa tgtatggaag ctctgggcat   1080

ggaatcagga gaaattcatt ctgaccagat cacagcttct tcccagtata gcaccaactg   1140

gtctgcagag cgctcccgcc tgaactaccc tgagaatggg tggactcccg gagaggattc   1200

ctaccgagag tggatacagg tagacttggg ccttctgcgc tttgtcacgg ctgtcgggac   1260

acagggcgcc atttcaaaag aaaccaagaa gaaatattat gtcaagactt acaagatcga   1320

cgttagctcc aacggggaag actggatcac cataaaagaa ggaaacaaac ctgttctctt   1380

tcagggaaac accaacccca cagatgttgt ggttgcagta ttccccaaac cactgataac   1440

tcgatttgtc cgaatcaagc ctgcaacttg ggaaactggc atatctatga gatttgaagt   1500

atacggttgc aagataacag attatccttg ctctggaatg ttgggtatgg tgtctggact   1560
```

-continued

```
tatttctgac tcccagatca catcatccaa ccaaggggac agaaactgga tgcctgaaaa   1620
catccgcctg gtaaccagtc gctctggctg ggcacttcca cccgcacctc attcctacat   1680
caatgagtgg ctccaaatag acctggggga ggagaagatc gtgaggggca tcatcattca   1740
gggtgggaag caccgagaga acaaggtgtt catgaggaag ttcaagatcg ggtacagcaa   1800
caacggctcg gactggaaga tgatcatgga tgacagcaaa cgcaaggcga agtcttttga   1860
gggcaacaac aactatgata cacctgagct gcggactttt ccagctctct ccacgcgatt   1920
catcaggatc taccccgaga gagccactca tggcggactg gggctcagaa tggagctgct   1980
gggctgtgaa gtggaagccc ctacagctgg accgaccact cccaacggga acttggtgga   2040
tgaatgtgat gacgaccagg ccaactgcca cagtggaaca ggtgatgact tccagctcac   2100
aggtggcacc actgtgctgg ccacagaaaa gcccacggtc atagacagca ccatacaatc   2160
agagtttcca acatatggtt ttaactgtga atttggctgg ggctctcaca agaccttctg   2220
ccactgggaa catgacaatc acgtgcagct caagtggagt gtgttgacca gcaagacggg   2280
acccattcag gatcacacag gagatggcaa cttcatctat tcccaagctg acgaaaatca   2340
gaagggcaaa gtggctcgcc tggtgagccc tgtggtttat tcccagaact ctgcccactg   2400
catgaccttc tggtatcaca tgtctgggtc ccacgtcggc acactcaggg tcaaactgcg   2460
ctaccagaag ccagaggagt acgatcagct ggtctggatg gccattggac accaaggtga   2520
ccactggaag gaagggcgtg tcttgctcca caagtctctg aaactttatc aggtgatttt   2580
cgagggcgaa atcggaaaag gaaaccttgg tgggattgct gtggatgaca ttagtattaa   2640
caaccacatt tcacaagaag attgtgcaaa accagcagac ctggataaaa agaacccaga   2700
aattaaaatt gatgaaacag ggagcacgcc aggatacgaa ggtgaaggag aaggtgacaa   2760
gaacatctcc aggaagccag gcaatgtgtt gaagacctta gatcccatcc tcatcaccat   2820
catagccatg agtgccctgg gggtcctcct gggggctgtc tgtggggtcg tgctgtactg   2880
tgcctgttgg cataatggga tgtcagaaag aaacttgtct gccctggaga actataactt   2940
tgaacttgtg gatggtgtga agttgaaaaa agacaaactg aatacacaga gtacttattc   3000
ggaggcatga aggcagacag agatgaaaag acagtcaaag gacggaagtg gaaggacggg   3060
agtgagctgg ggagctgttg atctttcact atacaggctg ggaagtgtgt tgatgaccac   3120
tgagccaggc ttttctcagg agcttcaatg agtatggccg acagacatgg acaaggagct   3180
gtgttcacca tcggactcat gtgcagtcag ctttttttcct gttggtttca tttgaataat   3240
cagatgctgg tgttgagacc aagtatgatt gacataatca ttcatttcga cccctcctgc   3300
ccctctctct ctctctcctc tcccctttgt ggattctttt tggaaactga gcgaaatcca   3360
agatgctggc accaagcgta ttccgtgtgg ccctttggat ggacatgcta cctgaaaccc   3420
agtgcccaga atatactaga atcaccgcat ttcagtggac tcctgaagtt gtacttgtgt   3480
ataattgccc gcgtcgtgca taggcaaaga aggattaggc tgttttcttt ttaaagtact   3540
gtagcctcag tactggtgta gtgtgtcagc tctgtttacg aagcaatact gtccagtttt   3600
cttgctgttt ttccggtgtt gtactaaacc tcgtgcttgt gaactccata cagaaaacgg   3660
tgccatccct gaacacggct ggccactggg tatactgctg acaaccgcaa caacaaaaac   3720
acaaatcctt ggcactggct agtctatgtc ctctcaagtg cctttttgtt tgtactggtt   3780
cattgtgtta cattaacgac ccactctgct tcttgctggt gaaagccctg ctctttaatc   3840
aaactctggt ggcccactga ctaagaagaa agtttatttt cgtgtgagat gccagcccct   3900
ccgggcaggc aagggctctg aagatttggc aacgtggctt aattgttctg ctttttctgt   3960
```

-continued

```
agttcaattt catgtttctt gacccttttg tataaagcta caatattctc tcttattgtt   4020

ctttcatatg gaatgtattt tcaaatgtaa actctcttct ctttctctct cctatctctc   4080

tgtctttttt ctctcttaga attggaggat ttgccattgt ccaggaaaga aacttgcagc   4140

tttaacctgc tgggaatggc aaacgatttt actagacttt atgtttaaaa ataaataaat   4200

aagggaaatt cctaactttg ccctccaaag tctaactttg gttttcttgt taactggtta   4260

aagtgacagt atcttttttc cttatctatt ctattcaaaa tgacctttga tagaaatgtt   4320

ggcatttagt agaaatagtg ataagttgag gaaagaaata atacaaattg gctttcaagt   4380

gagacccaaa ggaagaactg gataaaatct tccaaatcca aaagcatgag atttttctat   4440

ccaaatatgc aaaaatgacc caagagaact ttcttatttt gctactgagt cacacaaggg   4500

aagtggaagg aagaacagtt aatttaagaa tgaaactata aatcctgatg cctgggggtc   4560

aagtatttta agataagagg gggaaaaaca cataaagtca aacaaatgtt ttaaaaattc   4620

ataacagcaa ccttgaaaaa atagacttaa atgaatgctt ctagaaactt ccagcggctc   4680

acaaagaata agcctgcctt agggctggca acatctaagc ctctaacagc acagggaagc   4740

aaatatctta ccaggcagcc tatgaattaa cccaaagaag ctttggttgg ttttggtgga   4800

tttttatcat gccatgttgg acatgagatt ttttagatct tccttcccca cattgctaga   4860

cgtctcactc aaagacattt gttgggagtc acatttgcat catagacgag acagtccatt   4920

catcttagtt aaattggatt gagaatgcct tttgtttcca ggaaaatatt gatcaccatg   4980

aaagaagaat agtttttttgt ccccagagac attcatttag ttgatataat cctaccagaa   5040

ggaaagcact aagaaacact cgtttgttgt ttttaaaggc aacagactta aagttgtcct   5100

cagccaagga aaaatgatac tgcaacttta aaatttaaag tatcttgcac tgataaatat   5160

atttaaaaat tatatgttta taaagttatt aatttgtaaa ggcagtgtta caaaatgttc   5220

agtttatatt gttttagatt gttttgtaat ttttaaaggt gtaaaataac atataaatat   5280

atttaaaaat tatatgttta taaagttatt aatttgtaaa ggcagtgtta caaaatgttc   5340

agtttatatt gttttagatt gttttgtaat ttttaaaggt gtaaaataac atatttttc   5400

tttatggaaa tctataaaac tttctgtagt aaaatgtttt cattttactg gtatattatt   5460

gcttcatgtt ttgtaccatc ataagatttt gtgcagattt tttttacaga aattattatt   5520

ttctatgaca atatgacact tgtaaattgt tgtttcaaaa tgaacagcga agccttaact   5580

ttaaatgaca tttgtattct cagacactga gtagcataaa aaccacatga actgaactgt   5640

aacttaaatt ctt                                                      5653
```

<210> SEQ ID NO 2
<211> LENGTH: 923
<212> TYPE: PRT
<213> ORGANISM: human

<400> SEQUENCE: 2

```
Met Glu Arg Gly Leu Pro Leu Leu Cys Ala Val Leu Ala Leu Val Leu
 1               5                  10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60
```

-continued

```
Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
    450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
```

-continued

```
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910
```

-continued

Lys Leu Asn Thr Gln Ser Thr Tyr Ser Glu Ala
915 920

<210> SEQ ID NO 3
<211> LENGTH: 3404
<212> TYPE: DNA
<213> ORGANISM: human

<400> SEQUENCE: 3
gaattcggca cgaggggaaa ataaaagaga gaaaaacaca aagatttaaa caagaaacct 60
acgaacccag ctctggaaag agccaccttc tccaaaatgg atatgtttcc tctcacctgg 120
gttttcttag ccctctactt ttcaagacac caagtgagag gccaaccaga cccaccgtgc 180
ggaggtcgtt tgaattccaa agatgctggc tatatcacct ctcccggtta cccccaggac 240
tacccctccc accagaactg cgagtggatt gtttacgccc ccgaacccaa ccagaagatt 300
gtcctcaact tcaaccctca ctttgaaatc gagaagcacg actgcaagta tgactttatc 360
gagattcggg atggggacag tgaatccgca gacctcctgg gcaaacactg tgggaacatc 420
gccccgccca ccatcatctc ctcgggctcc atgctctaca tcaagttcac ctccgactac 480
gcccggcagg gggcaggctt ctctctgcgc tacgagatct tcaagacagg ctctgaagat 540
tgctcaaaaa acttcacaag ccccaacggg accatcgaat ctcctgggtt tcctgagaag 600
tatccacaca acttggactg cacctttacc atcctggcca aacccaagat ggagatcatc 660
ctgcagttcc tgatctttga cctggagcat gaccctttgc aggtgggaga gggggactgc 720
aagtacgatt ggctggacat ctgggatggc attccacatg ttggccccct gattggcaag 780
tactgtggga ccaaaacacc ctctgaactt cgttcatcga cggggatcct ctccctgacc 840
tttcacacgg acatggcggt ggccaaggat ggcttctctg cgcgttacta cctggtccac 900
caagagccac tagagaactt tcagtgcaat gttcctctgg gcatggagtc tggccggatt 960
gctaatgaac agatcagtgc ctcatctacc tactctgatg ggaggtggac ccctcaacaa 1020
agccggctcc atggtgatga caatggctgg acccccaact tggattccaa caaggagtat 1080
ctccaggtgg acctgcgctt tttaaccatg ctcacggcca tcgcaacaca gggagcgatt 1140
tccagggaaa cacagaatgg ctactacgtc aaatcctaca agctggaagt cagcactaat 1200
ggagaggact ggatggtgta ccggcatggc aaaaaccaca aggtatttca agccaacaac 1260
gatgcaactg aggtggttct gaacaagctc cacgctccac tgctgacaag gtttgttaga 1320
atccgccctc agacctggca ctcaggtatc gccctccggc tggagctctt cggctgccgg 1380
gtcacagatg ctccctgctc caacatgctg ggcatgctct caggcctcat tgcagactcc 1440
cagatctccg cctcttccac ccaggaatac ctctggagcc ccagtgcagc ccgcctggtc 1500
agcagccgct cgggctggtt ccctcgaatc cctcaggccc agcccggtga ggagtggctt 1560
caggtagatc tgggaacacc caagacagtg aaaggtgtca tcatccaggg agcccgcgga 1620
ggagacagta tcactgctgt ggaagccaga gcatttgtgc gcaagttcaa agtctcctac 1680
agcctaaacg gcaaggactg ggaatacatt caggacccca ggacccagca gccaaagctg 1740
ttcgaaggga acatgcacta tgacacccct gacatccgaa ggtttgaccc cattccggca 1800
cagtatgtgc gggtataccc ggagaggtgg tcgccggcgg ggattgggat gcggctggag 1860
gtgctgggct gtgactggac agactccaag cccacggtag agacgctggg acccactgtg 1920
aagagcgaag agacaaccac cccctacccc accgaagagg aggccacaga gtgtggggag 1980
aactgcagct ttgaggatga caaagatttg cagctccctt cgggattcaa ttgcaacttc 2040

```
gatttcctcg aggagccctg tggttggatg tatgaccatg ccaagtggct ccggaccacc   2100

tgggccagca gctccagccc aaacgaccgg acgtttccag atgacaggaa tttcttgcgg   2160

ctgcagagtg acagccagag agagggccag tatgcccggc tcatcagccc ccctgtccac   2220

ctgccccgaa gcccggtgtg catggagttc cagtaccagg ccacgggcgg ccgcggggtg   2280

gcgctgcagg tggtgcggga agccagccag gagagcaagt tgctgtgggt catccgtgag   2340

gaccagggcg gcgagtggaa gcacgggcgg atcatcctgc ccagctacga catggagtac   2400

cagattgtgt tcgagggagt gatagggaaa ggacgttccg gagagattgc cattgatgac   2460

attcggataa gcactgatgt cccactggag aactgcatgg aacccatctc ggcttttgca   2520

ggtgagaatt ttaaagtgga catcccagaa atacatgaga gagaaggata tgaagatgaa   2580

attgatgatg aatacgaggt ggactggagc aattcttctt ctgcaacctc agggtctggc   2640

gccccctcga ccgacaaaga aaagagctgg ctgtacaccc tggatcccat cctcatcacc   2700

atcatcgcca tgagctcact gggcgtcctc ctgggggcca cctgtgcagg cctcctgctc   2760

tactgcacct gttcctactc gggcctgagc tcccgaagct gcaccacact ggagaactac   2820

aacttcgagc tctacgatgg ccttaagcac aaggtcaaga tgaaccacca aaagtgctgc   2880

tccgaggcat gacggattgc acctgaatcc tatctgacgt ttcattccag caagaggggc   2940

tggggaagat tacatttttt tttcctttgg aaactgaatg ccataatctc gatcaaaccg   3000

atccagaata ccgaaggtat ggacaggaca gaaaagcgag tcgcaggagg aagggagatg   3060

cagccgcaca ggggatgatt accctcctag gaccgcggtg gctaagtcat tgcaggaacg   3120

gggctgtgtt ctctgctggg acaaaacagg agctcatctc tttggggtca cagttctatt   3180

ttgtttgtga gtttgtatta ttattattat tattattatt atattttatt tctttggtct   3240

gtgagcaact caaagaggca gaagaggaga atgacttttc cagaatagaa gtggagcagt   3300

gatcattatt ctccgctttc tctttctaat caacacttga aaagcaaagt gtcttttcag   3360

cctttccatc tttacaaata aaactcaaaa aagctgtcca gctt                    3404
```

<210> SEQ ID NO 4
<211> LENGTH: 931
<212> TYPE: PRT
<213> ORGANISM: human

<400> SEQUENCE: 4

```
Met Asp Met Phe Pro Leu Thr Trp Val Phe Leu Ala Leu Tyr Phe Ser
1               5                   10                  15

Arg His Gln Val Arg Gly Gln Pro Asp Pro Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125
```

-continued

```
Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Pro Lys Leu Phe Glu Gly Asn Met His Tyr Asp Thr Pro Asp Ile
```

-continued

```
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605

Lys Ser Glu Glu Thr Thr Thr Pro Tyr Pro Thr Glu Glu Glu Ala Thr
    610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
        675                 680                 685

Leu Gln Ser Asp Ser Gln Arg Glu Gly Gln Tyr Ala Arg Leu Ile Ser
    690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Gly Glu Asn Phe Lys Val Asp Ile
                805                 810                 815

Pro Glu Ile His Glu Arg Glu Gly Tyr Glu Asp Glu Ile Asp Asp Glu
            820                 825                 830

Tyr Glu Val Asp Trp Ser Asn Ser Ser Ser Ala Thr Ser Gly Ser Gly
        835                 840                 845

Ala Pro Ser Thr Asp Lys Glu Lys Ser Trp Leu Tyr Thr Leu Asp Pro
    850                 855                 860

Ile Leu Ile Thr Ile Ile Ala Met Ser Ser Leu Gly Val Leu Leu Gly
865                 870                 875                 880

Ala Thr Cys Ala Gly Leu Leu Leu Tyr Cys Thr Cys Ser Tyr Ser Gly
                885                 890                 895

Leu Ser Ser Arg Ser Cys Thr Thr Leu Glu Asn Tyr Asn Phe Glu Leu
            900                 905                 910

Tyr Asp Gly Leu Lys His Lys Val Lys Met Asn His Gln Lys Cys Cys
        915                 920                 925

Ser Glu Ala
    930

<210> SEQ ID NO 5
<211> LENGTH: 18
<212> TYPE: PRT
<213> ORGANISM: human
```

-continued

<400> SEQUENCE: 5

```
Phe Arg Asn Asp Glu Cys Gly Asp Thr Ile Lys Ile Glu Asn Pro Gly
 1               5                  10                  15

Tyr Leu
```

<210> SEQ ID NO 6
<211> LENGTH: 18
<212> TYPE: PRT
<213> ORGANISM: human

<400> SEQUENCE: 6

```
Phe Arg Ser Asp Lys Cys Gly Gly Thr Ile Lys Ile Glu Ser Pro Gly
 1               5                  10                  15

Tyr Leu
```

<210> SEQ ID NO 7
<211> LENGTH: 24
<212> TYPE: DNA
<213> ORGANISM: human

<400> SEQUENCE: 7

```
tttcgcaacg ataaatgtgg cgat                                             24
```

<210> SEQ ID NO 8
<211> LENGTH: 20
<212> TYPE: DNA
<213> ORGANISM: human

<400> SEQUENCE: 8

```
tatcactcca ctaggtgttg                                                  20
```

<210> SEQ ID NO 9
<211> LENGTH: 20
<212> TYPE: DNA
<213> ORGANISM: human

<400> SEQUENCE: 9

```
ccaaccagaa gattgtcctc                                                  20
```

<210> SEQ ID NO 10
<211> LENGTH: 20
<212> TYPE: DNA
<213> ORGANISM: human

<400> SEQUENCE: 10

```
gtaggtagat gaggcactga                                                  20
```

<210> SEQ ID NO 11
<211> LENGTH: 44
<212> TYPE: PRT
<213> ORGANISM: human

<400> SEQUENCE: 11

```
Pro Cys Gly Pro Cys Ser Glu Arg Arg Lys His Leu Phe Val Gln Asp
 1               5                  10                  15

Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys Arg
        35                  40
```